US012202865B2

(12) United States Patent
Singh et al.

(10) Patent No.: US 12,202,865 B2
(45) Date of Patent: Jan. 21, 2025

(54) MULTIVALENT MALARIA TRANSMISSION-BLOCKING VACCINES

(71) Applicant: Statens Serum Institut, Copenhagen S (DK)

(72) Inventors: Susheel Kumar Singh, Vanlose (DK); Michael Theisen, Holte (DK)

( * ) Notice: Subject to any disclaimer, the term of this patent is extended or adjusted under 35 U.S.C. 154(b) by 656 days.

(21) Appl. No.: 17/601,056

(22) PCT Filed: Mar. 30, 2020

(86) PCT No.: PCT/EP2020/058906
§ 371 (c)(1),
(2) Date: Oct. 2, 2021

(87) PCT Pub. No.: WO2021/197564
PCT Pub. Date: Oct. 7, 2021

(65) Prior Publication Data

US 2022/0194996 A1 Jun. 23, 2022

(30) Foreign Application Priority Data

Apr. 4, 2019 (EP) .................................... 19167453

(51) Int. Cl.

| | |
|---|---|
| ***A61K 39/02*** | (2006.01) |
| ***A61K 39/002*** | (2006.01) |
| ***A61P 33/06*** | (2006.01) |
| ***A61P 37/04*** | (2006.01) |
| ***C07K 1/10*** | (2006.01) |
| ***C07K 14/445*** | (2006.01) |
| *A61K 39/00* | (2006.01) |

(52) U.S. Cl.
CPC ............ *C07K 14/445* (2013.01); *A61P 33/06* (2018.01); *A61P 37/04* (2018.01); *C07K 1/10* (2013.01); *A61K 39/00* (2013.01); *A61K 2039/5258* (2013.01)

(58) Field of Classification Search
None
See application file for complete search history.

(56) References Cited

FOREIGN PATENT DOCUMENTS

| | | |
|---|---|---|
| WO | 2013/050034 A1 | 11/2013 |
| WO | 2014/174054 A1 | 10/2014 |

OTHER PUBLICATIONS

Devos et al., (Proteins: Structure, Function and Genetics, 2000, vol. 41: 98-107).*
Whisstock et al., (Quarterly Reviews of Biophysics 2003, vol. 36 (3): 307-340,).*
Witowski et al., (Biochemistry 38:11643-11650, 1999).*
Kisselev L., (Structure, 2002, vol. 10: 8-9).*
Mikayama et al. (Nov. 1993. Proc.Natl.Acad.Sci. USA, vol. 90 : 10056-10060).*
Rudinger et al. (Jun. 1976. Peptide Hormones. Biol. Council. pp. 5-7).*
Acquah, et al., Antibody responses to two new Lactococcus lactis-produced recombinant Pfs48/45 and Pfs230 proteins increase with age in malaria patients living in the Central Region of Ghana, Malaria Journal, Aug. 1, 2017, 1-11, 16:306.
Singh, et al., Pfs230 and Pfs48/45 Fusion Proteins Elicit Strong Transmission-Blocking Antibody Responses Against Plasmodium falciparum, Front. Immunol., Jun. 5, 2019, 1-12, 10(1256).
Theisen, et al., A multi-stage malaria vaccine candidate targeting both transmission and asexual parasite life-cycle stages, Vaccine, May 1, 2014 (online Mar. 21, 2014), 2623-2630, 32.
Tachibana, et al., Identification of domains within Pfs230 that elicit transmission blocking antibody responses, Vaccine, Mar. 22, 2019 (online Feb. 26, 2019), 1799-1806, 37.
Stone, et al., Unravelling the immune signature of Plasmodium falciparum transmission-reducing immunity, Nature Communications, Feb. 8, 2018, 1-14.

* cited by examiner

*Primary Examiner* — Jennifer E Graser
(74) *Attorney, Agent, or Firm* — Howson & Howson, LLP; Kathleen D. Rigaut; Richard F. Kane

(57) ABSTRACT

The present invention relates to a method for recombinant production of a fusion protein comprising multiple malaria antigens for inducing immune responses comprising a combination of antibodies. In particular, the fusion proteins of the present invention comprise fragments of both Pfs230 and Pfs48/45 to lower the required threshold of functional antibodies and to reduce the risk of escape mutations. Thus, the fusion proteins of the present invention are suitable for use in a multivalent malaria vaccine.

18 Claims, 12 Drawing Sheets

Specification includes a Sequence Listing.

Pro-6C-VLP Pro+I-6C-VLP

Coomassie mAb45.1 mAb 15C5 (Anti-domain I)

SEQUENCE LISTING

```
<160> NUMBER OF SEQ ID NOS: 71

<210> SEQ ID NO 1
<211> LENGTH: 148
<212> TYPE: PRT
<213> ORGANISM: Plasmodium falciparum
<220> FEATURE:
<221> NAME/KEY: Pfs230 Pro domain protein sequence
<222> LOCATION: (1)..(1)

<400> SEQUENCE: 1

Glu Tyr Val Asp Glu Lys Glu Arg Gln Gly Glu Ile Tyr Pro Phe Gly
1               5                   10                  15

Asp Glu Glu Glu Lys Asp Glu Gly Gly Glu Ser Phe Thr Tyr Glu Lys
            20                  25                  30

Ser Glu Val Asp Lys Thr Asp Leu Phe Lys Phe Ile Glu Gly Gly Glu
        35                  40                  45

Gly Asp Asp Val Tyr Lys Val Asp Gly Ser Lys Val Leu Leu Asp Asp
    50                  55                  60

Asp Thr Ile Ser Arg Val Ser Lys Lys His Thr Ala Arg Asp Gly Glu
65                  70                  75                  80

Tyr Gly Glu Tyr Gly Glu Ala Val Glu Asp Gly Glu Asn Val Ile Lys
```

-continued

```
                85                  90                  95

Ile Ile Arg Ser Val Leu Gln Ser Gly Ala Leu Pro Ser Val Gly Val
            100                 105                 110

Asp Glu Leu Asp Lys Ile Asp Leu Ser Tyr Glu Thr Thr Glu Ser Gly
        115                 120                 125

Asp Thr Ala Val Ser Glu Asp Ser Tyr Asp Lys Tyr Ala Ser Asn Asn
    130                 135                 140

Thr Asn Lys Glu
145


<210> SEQ ID NO 2
<211> LENGTH: 444
<212> TYPE: DNA
<213> ORGANISM: Plasmodium falciparum
<220> FEATURE:
<221> NAME/KEY: Pfs230 Pro domain nucleic acid sequence
<222> LOCATION: (1)..(1)

<400> SEQUENCE: 2

gaatatgtcg acgaaaaaga acgtcaaggt gaaatttatc cattcggcga cgaagaagaa      60

aaagatgaag gtggtgaaag ctttacttat gaaaaatctg aagttgataa aactgatttg     120

tttaaattca tcgaaggcgg tgaaggtgac gacgtttata aagttgatgg aagcaaagtt     180

cttcttgacg acgatacaat tagccgtgtc tcaaaaaaac atacagctcg tgatggtgaa     240

tacggtgaat atggggaagc agttgaagat ggggaaaacg tcattaaaat catccgttca     300

gttcttcaat caggtgcttt accatcagtt ggtgttgatg aacttgacaa aattgattta     360

agttatgaaa caacagaatc aggggacaca gctgtttctg aagattcata tgataaatat     420

gcttcaaata atacaaataa agaa                                            444


<210> SEQ ID NO 3
<211> LENGTH: 146
<212> TYPE: PRT
<213> ORGANISM: Plasmodium falciparum
<220> FEATURE:
<221> NAME/KEY: Pfs230 domain I protein sequence
<222> LOCATION: (1)..(1)

<400> SEQUENCE: 3

Tyr Val Cys Asp Phe Thr Asp Gln Leu Lys Pro Thr Glu Ser Gly Pro
1               5                   10                  15

Lys Val Lys Lys Cys Glu Val Lys Val Asn Glu Pro Leu Ile Lys Val
            20                  25                  30

Lys Ile Ile Cys Pro Leu Lys Gly Ser Val Glu Lys Leu Tyr Asp Asn
        35                  40                  45

Ile Glu Tyr Val Pro Lys Lys Ser Pro Tyr Val Val Leu Thr Lys Glu
    50                  55                  60

Glu Thr Lys Leu Lys Glu Lys Leu Leu Ser Lys Leu Ile Tyr Gly Leu
65                  70                  75                  80

Leu Ile Ser Pro Thr Val Asn Glu Lys Glu Asn Asn Phe Lys Glu Gly
                85                  90                  95

Val Ile Glu Phe Thr Leu Pro Pro Val Val His Lys Ala Thr Val Phe
            100                 105                 110

Tyr Phe Ile Cys Asp Asn Ser Lys Thr Glu Asp Asp Asn Lys Lys Gly
        115                 120                 125

Asn Arg Gly Ile Val Glu Val Tyr Val Glu Pro Tyr Gly Asn Lys Ile
    130                 135                 140
```

Asn Gly
145

<210> SEQ ID NO 4
<211> LENGTH: 438
<212> TYPE: DNA
<213> ORGANISM: Plasmodium falciparum
<220> FEATURE:
<221> NAME/KEY: Pfs230 domain I nucleic acid sequence
<222> LOCATION: (1)..(1)

<400> SEQUENCE: 4
tacgtttgtg attttacaga tcaattaaaa ccaacagaaa gtggtcctaa agtaaaaaaa 60
tgtgaagtaa aagttaatga gccattaata aaagtaaaaa taatatgtcc attaaaaggt 120
tctgtagaaa aattatatga taatatagaa tatgtaccta aaaaaagccc atatgttgtt 180
ttaacaaaag aggaaactaa actaaaggaa aaacttctct cgaaacttat ttatggttta 240
ttaatatctc cgacggttaa cgaaaaggag aataatttta aagaaggtgt tattgaattt 300
actcttcccc ctgtggtaca caaggcaaca gtgttttatt ttatatgtga taattcaaaa 360
acagaagatg ataacaaaaa aggaaataga gggattgtag aagtgtatgt agaaccatat 420
ggtaataaaa ttaatgga 438

<210> SEQ ID NO 5
<211> LENGTH: 182
<212> TYPE: PRT
<213> ORGANISM: Plasmodium falciparum
<220> FEATURE:
<221> NAME/KEY: Pfs230 domain II protein sequence
<222> LOCATION: (1)..(1)

<400> SEQUENCE: 5

Cys Ala Phe Leu Asp Glu Asp Glu Glu Glu Glu Lys Tyr Gly Asn Gln
1 5 10 15

Ile Glu Glu Asp Glu His Asn Glu Lys Ile Lys Met Lys Thr Phe Phe
20 25 30

Thr Gln Asn Ile Tyr Lys Lys Asn Asn Ile Tyr Pro Cys Tyr Met Lys
35 40 45

Leu Tyr Ser Gly Asp Ile Gly Gly Ile Leu Phe Pro Lys Asn Ile Lys
50 55 60

Ser Thr Thr Cys Phe Glu Glu Met Ile Pro Tyr Asn Lys Glu Ile Lys
65 70 75 80

Trp Asn Lys Glu Asn Lys Ser Leu Gly Asn Leu Val Asn Asn Ser Val
85 90 95

Val Tyr Asn Lys Glu Met Asn Ala Lys Tyr Phe Asn Val Gln Tyr Val
100 105 110

His Ile Pro Thr Ser Tyr Lys Asp Thr Leu Asn Leu Phe Cys Ser Ile
115 120 125

Ile Leu Lys Glu Glu Glu Ser Asn Leu Ile Ser Thr Ser Tyr Leu Val
130 135 140

Tyr Val Ser Ile Asn Glu Glu Leu Asn Phe Ser Leu Phe Asp Phe Tyr
145 150 155 160

Glu Ser Phe Val Pro Ile Lys Lys Thr Ile Gln Val Ala Gln Lys Asn
165 170 175

Val Asn Asn Lys Glu His
180

<210> SEQ ID NO 6

<211> LENGTH: 546
<212> TYPE: DNA
<213> ORGANISM: Plasmodium falciparum
<220> FEATURE:
<221> NAME/KEY: Pfs230 domain II nucleic acid sequence
<222> LOCATION: (1)..(1)

<400> SEQUENCE: 6
tgtgctttct tggatgaaga tgaagaagaa gaaaaatatg gtaatcaaat tgaagaagat 60
gaacataatg agaagataaa aatgaaaaca ttctttaccc agaatatata taaaaaaaat 120
aatatatatc catgttatat gaaattatat agcggagata taggtggtat tctatttcct 180
aagaatataa aatcaacaac gtgttttgaa gagatgatac cttataataa agaaataaaa 240
tggaataaag aaaataaaag tttaggtaac ttagttaata attctgtagt atataataaa 300
gagatgaatg caaaatattt taatgttcag tatgttcaca ttcctacaag ttataaagat 360
acattaaatt tattttgtag tattatatta aaagaagagg aaagtaattt aatttctact 420
tcttatttag tatatgtaag tattaatgaa gaattaaatt tttcactttt cgatttttat 480
gaatcatttg tacctataaa aaaaaccata caagtagctc aaaagaatgt aaataataaa 540
gaacat 546

<210> SEQ ID NO 7
<211> LENGTH: 214
<212> TYPE: PRT
<213> ORGANISM: Plasmodium falciparum
<220> FEATURE:
<221> NAME/KEY: Pfs230 domain III protein sequence
<222> LOCATION: (1)..(1)

<400> SEQUENCE: 7

Asp Tyr Thr Cys Asp Phe Thr Asp Lys Leu Asp Lys Thr Val Pro Ser
1 5 10 15

Thr Ala Asn Gly Lys Lys Leu Phe Ile Cys Arg Lys His Leu Lys Glu
20 25 30

Phe Asp Thr Phe Thr Leu Lys Cys Asn Val Asn Lys Thr Gln Tyr Pro
35 40 45

Asn Ile Glu Ile Phe Pro Lys Thr Leu Lys Asp Lys Lys Glu Val Leu
50 55 60

Lys Leu Asp Leu Asp Ile Gln Tyr Gln Met Phe Ser Lys Phe Phe Lys
65 70 75 80

Phe Asn Thr Gln Asn Ala Lys Tyr Leu Asn Leu Tyr Pro Tyr Tyr Leu
85 90 95

Ile Phe Pro Phe Asn His Ile Gly Lys Lys Glu Leu Lys Asn Asn Pro
100 105 110

Thr Tyr Lys Asn His Lys Asp Val Lys Tyr Phe Glu Gln Ser Ser Val
115 120 125

Leu Ser Pro Leu Ser Ser Ala Asp Ser Leu Gly Lys Leu Leu Asn Phe
130 135 140

Leu Asp Thr Gln Glu Thr Val Cys Leu Thr Glu Lys Ile Arg Tyr Leu
145 150 155 160

Asn Leu Ser Ile Asn Glu Leu Gly Ser Asp Asn Asn Thr Phe Ser Val
165 170 175

Thr Phe Gln Val Pro Pro Tyr Ile Asp Ile Lys Glu Pro Phe Tyr Phe
180 185 190

Met Phe Gly Cys Asn Asn Asn Lys Gly Glu Gly Asn Ile Gly Ile Val
195 200 205

```
Glu Leu Leu Ile Ser Lys
    210


<210> SEQ ID NO 8
<211> LENGTH: 645
<212> TYPE: DNA
<213> ORGANISM: Plasmodium falciparum
<220> FEATURE:
<221> NAME/KEY: Pfs230 domain III nucleic acid sequence
<222> LOCATION: (1)..(1)

<400> SEQUENCE: 8

gattatacat gtgattttac cgataaatta gataaaacgg ttccttctac tgctaatggg      60

aagaaattat ttatatgtag aaagcattta aaagaatttg atacatttac cttaaaatgt     120

aatgttaata aaacacaata tccaaatatc gagatatttc ctaaaacatt aaaagataaa     180

aaggaagtat taaaattaga tcttgatata caatatcaaa tgtttagtaa attttttaaa     240

ttcaatacac agaatgcaaa gtatttaaat ttatatccat attatttaat ttttccattt     300

aatcatatag gaaaaaaaga attaaaaaat aatcctacat ataaaaatca taaagatgtg     360

aaatattttg agcaatcatc tgtattatct cccttatctt ccgcagacag tttagggaaa     420

ttattaaatt ttttagatac tcaagagacg gtatgtctta cggaaaagat aagatattta     480

aatttaagta tcaatgagtt aggatctgat aataatacat tttctgtaac atttcaggtt     540

ccaccatata tagatattaa ggaacctttt tattttatgt ttggttgtaa taataataaa     600

ggtgaaggga atatcggaat tgttgaatta ttaatatcta agcaa                     645


<210> SEQ ID NO 9
<211> LENGTH: 296
<212> TYPE: PRT
<213> ORGANISM: Plasmodium falciparum
<220> FEATURE:
<221> NAME/KEY: Pfs230 Pro+I protein sequence
<222> LOCATION: (1)..(1)

<400> SEQUENCE: 9

Glu Tyr Val Asp Glu Lys Glu Arg Gln Gly Glu Ile Tyr Pro Phe Gly
1               5                   10                  15

Asp Glu Glu Glu Lys Asp Glu Gly Gly Glu Ser Phe Thr Tyr Glu Lys
            20                  25                  30

Ser Glu Val Asp Lys Thr Asp Leu Phe Lys Phe Ile Glu Gly Gly Glu
        35                  40                  45

Gly Asp Asp Val Tyr Lys Val Asp Gly Ser Lys Val Leu Leu Asp Asp
    50                  55                  60

Asp Thr Ile Ser Arg Val Ser Lys Lys His Thr Ala Arg Asp Gly Glu
65                  70                  75                  80

Tyr Gly Glu Tyr Gly Glu Ala Val Glu Asp Gly Glu Asn Val Ile Lys
                85                  90                  95

Ile Ile Arg Ser Val Leu Gln Ser Gly Ala Leu Pro Ser Val Gly Val
            100                 105                 110

Asp Glu Leu Asp Lys Ile Asp Leu Ser Tyr Glu Thr Thr Glu Ser Gly
        115                 120                 125

Asp Thr Ala Val Ser Glu Asp Ser Tyr Asp Lys Tyr Ala Ser Asn Asn
    130                 135                 140

Thr Asn Lys Glu Arg Ser Tyr Val Cys Asp Phe Thr Asp Gln Leu Lys
145                 150                 155                 160

Pro Thr Glu Ser Gly Pro Lys Val Lys Lys Cys Glu Val Lys Val Asn
                165                 170                 175
```

```
Glu Pro Leu Ile Lys Val Lys Ile Ile Cys Pro Leu Lys Gly Ser Val
            180                 185                 190

Glu Lys Leu Tyr Asp Asn Ile Glu Tyr Val Pro Lys Lys Ser Pro Tyr
        195                 200                 205

Val Val Leu Thr Lys Glu Glu Thr Lys Leu Lys Glu Lys Leu Leu Ser
    210                 215                 220

Lys Leu Ile Tyr Gly Leu Leu Ile Ser Pro Thr Val Asn Glu Lys Glu
225                 230                 235                 240

Asn Asn Phe Lys Glu Gly Val Ile Glu Phe Thr Leu Pro Pro Val Val
                245                 250                 255

His Lys Ala Thr Val Phe Tyr Phe Ile Cys Asp Asn Ser Lys Thr Glu
            260                 265                 270

Asp Asp Asn Lys Lys Gly Asn Arg Gly Ile Val Glu Val Tyr Val Glu
        275                 280                 285

Pro Tyr Gly Asn Lys Ile Asn Gly
    290                 295


<210> SEQ ID NO 10
<211> LENGTH: 888
<212> TYPE: DNA
<213> ORGANISM: Plasmodium falciparum
<220> FEATURE:
<221> NAME/KEY: Pfs230 Pro+I nucleic acid sequence
<222> LOCATION: (1)..(1)

<400> SEQUENCE: 10

gaatatgtcg acgaaaaaga acgtcaaggt gaaatttatc cattcggcga cgaagaagaa      60

aaagatgaag gtggtgaaag ctttacttat gaaaaatctg aagttgataa aactgatttg     120

tttaaattca tcgaaggcgg tgaaggtgac gacgtttata aagttgatgg aagcaaagtt     180

cttcttgacg acgatacaat tagccgtgtc tcaaaaaaac atacagctcg tgatggtgaa     240

tacggtgaat atggggaagc agttgaagat ggggaaaacg tcattaaaat catccgttca     300

gttcttcaat caggtgcttt accatcagtt ggtgttgatg aacttgacaa aattgattta     360

agttatgaaa caacagaatc aggggacaca gctgtttctg aagattcata tgataaatat     420

gcttcaaata atacaaataa agaaaagatcc tacgtttgtg attttacaga tcaattaaaa    480

ccaacagaaa gtggtcctaa agtaaaaaaa tgtgaagtaa aagttaatga gccattaata     540

aaagtaaaaa taatatgtcc attaaaaggt tctgtagaaa aattatatga taatatagaa     600

tatgtaccta aaaaaagccc atatgttgtt ttaacaaaag aggaaactaa actaaaggaa     660

aaacttctct cgaaacttat ttatggttta ttaatatctc cgacggttaa cgaaaaggag     720

aataatttta aagaaggtgt tattgaattt actcttcccc ctgtggtaca caaggcaaca     780

gtgttttatt ttatatgtga taattcaaaa acagaagatg ataacaaaaa aggaaataga     840

gggattgtag aagtgtatgt agaaccatat ggtaataaaa ttaatgga                  888


<210> SEQ ID NO 11
<211> LENGTH: 138
<212> TYPE: PRT
<213> ORGANISM: Plasmodium falciparum
<220> FEATURE:
<221> NAME/KEY: Pfs48/45 6C domain protein sequence
<222> LOCATION: (1)..(1)

<400> SEQUENCE: 11

Glu Lys Lys Val Ile His Gly Cys Asn Phe Ser Ser Asn Val Ser Ser
1               5                   10                  15
```

```
Lys His Thr Phe Thr Asp Ser Leu Asp Ile Ser Leu Val Asp Asp Ser
            20                  25                  30

Ala His Ile Ser Cys Asn Val His Leu Ser Glu Pro Lys Tyr Asn His
        35                  40                  45

Leu Val Gly Leu Asn Cys Pro Gly Asp Ile Ile Pro Asp Cys Phe Phe
    50                  55                  60

Gln Val Tyr Gln Pro Glu Ser Glu Glu Leu Glu Pro Ser Asn Ile Val
65                  70                  75                  80

Tyr Leu Asp Ser Gln Ile Asn Ile Gly Asp Ile Glu Tyr Tyr Glu Asp
                85                  90                  95

Ala Glu Gly Asp Asp Lys Ile Lys Leu Phe Gly Ile Val Gly Ser Ile
            100                 105                 110

Pro Lys Thr Thr Ser Phe Thr Cys Ile Cys Lys Lys Asp Lys Lys Ser
        115                 120                 125

Ala Tyr Met Thr Val Thr Ile Asp Ser Ala
    130                 135


<210> SEQ ID NO 12
<211> LENGTH: 414
<212> TYPE: DNA
<213> ORGANISM: Plasmodium falciparum
<220> FEATURE:
<221> NAME/KEY: Pfs48/45 6C domain nucleic acid sequence
<222> LOCATION: (1)..(1)

<400> SEQUENCE: 12

gaaaaaaaag tcatacacgg atgtaacttc tcttcaaatg ttagttctaa acatactttt      60

acagatagtt tagatatttc tttagttgat gatagtgcac atatttcatg taacgtacat     120

ttgtctgaac caaaatataa tcatttggta ggtttaaatt gtcctggtga tattatacca     180

gattgctttt ttcaagtata tcaacctgaa tcagaagaac ttgaaccatc caacattgtt     240

tatttagatt cacaaataaa tataggagat attgaatatt atgaagatgc tgaaggagat     300

gataaaatta aattatttgg tatagttgga agtataccaa aaacgacatc ttttacttgt     360

atatgtaaga aggataaaaa aagtgcttat atgacagtta ctatagattc agca           414


<210> SEQ ID NO 13
<211> LENGTH: 270
<212> TYPE: PRT
<213> ORGANISM: Plasmodium falciparum
<220> FEATURE:
<221> NAME/KEY: Pfs48/45 10C domain protein sequence
<222> LOCATION: (1)..(1)

<400> SEQUENCE: 13

Asp Asn Thr Glu Lys Val Ile Ser Ser Ile Glu Gly Arg Ser Ala Met
1               5                   10                  15

Val His Val Arg Val Leu Lys Tyr Pro His Asn Ile Leu Phe Thr Asn
            20                  25                  30

Leu Thr Asn Asp Leu Phe Thr Tyr Leu Pro Lys Thr Tyr Asn Glu Ser
        35                  40                  45

Asn Phe Val Ser Asn Val Leu Glu Val Glu Leu Asn Asp Gly Glu Leu
    50                  55                  60

Phe Val Leu Ala Cys Glu Leu Ile Asn Lys Lys Cys Phe Gln Glu Gly
65                  70                  75                  80

Lys Glu Lys Ala Leu Tyr Lys Ser Asn Lys Ile Ile Tyr His Lys Asn
                85                  90                  95
```

-continued

```
Leu Thr Ile Phe Lys Ala Pro Phe Tyr Val Thr Ser Lys Asp Val Asn
            100                 105                 110

Thr Glu Cys Thr Cys Lys Phe Lys Asn Asn Asn Tyr Lys Ile Val Leu
        115                 120                 125

Lys Pro Lys Tyr Glu Lys Lys Val Ile His Gly Cys Asn Phe Ser Ser
    130                 135                 140

Asn Val Ser Ser Lys His Thr Phe Thr Asp Ser Leu Asp Ile Ser Leu
145                 150                 155                 160

Val Asp Asp Ser Ala His Ile Ser Cys Asn Val His Leu Ser Glu Pro
                165                 170                 175

Lys Tyr Asn His Leu Val Gly Leu Asn Cys Pro Gly Asp Ile Ile Pro
            180                 185                 190

Asp Cys Phe Phe Gln Val Tyr Gln Pro Glu Ser Glu Glu Leu Glu Pro
        195                 200                 205

Ser Asn Ile Val Tyr Leu Asp Ser Gln Ile Asn Ile Gly Asp Ile Glu
    210                 215                 220

Tyr Tyr Glu Asp Ala Glu Gly Asp Asp Lys Ile Lys Leu Phe Gly Ile
225                 230                 235                 240

Val Gly Ser Ile Pro Lys Thr Thr Ser Phe Thr Cys Ile Cys Lys Lys
                245                 250                 255

Asp Lys Lys Ser Ala Tyr Met Thr Val Thr Ile Asp Ser Ala
            260                 265                 270


<210> SEQ ID NO 14
<211> LENGTH: 810
<212> TYPE: DNA
<213> ORGANISM: Plasmodium falciparum
<220> FEATURE:
<221> NAME/KEY: Pfs 48/45 10C domain nucleic acid sequence
<222> LOCATION: (1)..(1)

<400> SEQUENCE: 14

gataatactg aaaaggttat atcaagtata gaagggagaa gtgctatggt acatgtacgt      60

gtattaaaat atccacataa tattttattt actaatttaa caaatgatct tttacatat      120

ttgccgaaaa catataatga atctaatttt gtaagtaatg tattagaagt agaattgaat     180

gatggagaat tatttgtttt agcttgtgaa ctaattaata aaaaatgttt tcaagaagga     240

aaagaaaaag ccttatataa aagtaataaa ataatttatc ataaaaactt aactatcttt     300

aaagctccat tttatgttac atcaaaagat gttaatacag aatgtacatg caaatttaaa     360

aataataatt ataaaatagt tttaaaacca aaatatgaaa aaaaagtcat acacggatgt     420

aacttctctt caaatgttag ttctaaacat acttttacag atagtttaga tatttcttta     480

gttgatgata gtgcacatat ttcatgtaac gtacatttgt ctgaaccaaa atataatcat     540

ttggtaggtt taaattgtcc tggtgatatt ataccagatt gcttttttca agtatatcaa     600

cctgaatcag aagaacttga accatccaac attgtttatt tagattcaca aataaatata     660

ggagatattg aatattatga agatgctgaa ggagatgata aaattaaatt atttggtata     720

gttggaagta taccaaaaac gacatctttt acttgtatat gtaagaagga taaaaaaagt     780

gcttatatga cagttactat agattcagca                                      810


<210> SEQ ID NO 15
<211> LENGTH: 288
<212> TYPE: PRT
<213> ORGANISM: Plasmodium falciparum
<220> FEATURE:
<221> NAME/KEY: Pfs230-Pfs48/45 Pro-6C protein sequence
```

<222> LOCATION: (1)..(1)

<400> SEQUENCE: 15

```
Glu Tyr Val Asp Glu Lys Glu Arg Gln Gly Glu Ile Tyr Pro Phe Gly
1               5                   10                  15

Asp Glu Glu Glu Lys Asp Glu Gly Gly Glu Ser Phe Thr Tyr Glu Lys
            20                  25                  30

Ser Glu Val Asp Lys Thr Asp Leu Phe Lys Phe Ile Glu Gly Gly Glu
        35                  40                  45

Gly Asp Asp Val Tyr Lys Val Asp Gly Ser Lys Val Leu Leu Asp Asp
    50                  55                  60

Asp Thr Ile Ser Arg Val Ser Lys Lys His Thr Ala Arg Asp Gly Glu
65                  70                  75                  80

Tyr Gly Glu Tyr Gly Glu Ala Val Glu Asp Gly Glu Asn Val Ile Lys
                85                  90                  95

Ile Ile Arg Ser Val Leu Gln Ser Gly Ala Leu Pro Ser Val Gly Val
            100                 105                 110

Asp Glu Leu Asp Lys Ile Asp Leu Ser Tyr Glu Thr Thr Glu Ser Gly
        115                 120                 125

Asp Thr Ala Val Ser Glu Asp Ser Tyr Asp Lys Tyr Ala Ser Asn Asn
    130                 135                 140

Thr Asn Lys Glu Arg Ser Glu Lys Lys Val Ile His Gly Cys Asn Phe
145                 150                 155                 160

Ser Ser Asn Val Ser Ser Lys His Thr Phe Thr Asp Ser Leu Asp Ile
                165                 170                 175

Ser Leu Val Asp Asp Ser Ala His Ile Ser Cys Asn Val His Leu Ser
            180                 185                 190

Glu Pro Lys Tyr Asn His Leu Val Gly Leu Asn Cys Pro Gly Asp Ile
        195                 200                 205

Ile Pro Asp Cys Phe Phe Gln Val Tyr Gln Pro Glu Ser Glu Glu Leu
    210                 215                 220

Glu Pro Ser Asn Ile Val Tyr Leu Asp Ser Gln Ile Asn Ile Gly Asp
225                 230                 235                 240

Ile Glu Tyr Tyr Glu Asp Ala Glu Gly Asp Asp Lys Ile Lys Leu Phe
                245                 250                 255

Gly Ile Val Gly Ser Ile Pro Lys Thr Thr Ser Phe Thr Cys Ile Cys
            260                 265                 270

Lys Lys Asp Lys Lys Ser Ala Tyr Met Thr Val Thr Ile Asp Ser Ala
        275                 280                 285
```

<210> SEQ ID NO 16
<211> LENGTH: 864
<212> TYPE: DNA
<213> ORGANISM: Plasmodium falciparum
<220> FEATURE:
<221> NAME/KEY: Pfs230-Pfs48/45 Pro-6C nucleic acid sequence
<222> LOCATION: (1)..(1)

<400> SEQUENCE: 16

```
gaatatgtcg acgaaaaaga acgtcaaggt gaaatttatc cattcggcga cgaagaagaa      60

aaagatgaag gtggtgaaag ctttacttat gaaaaatctg aagttgataa aactgatttg     120

tttaaattca tcgaaggcgg tgaaggtgac gacgtttata aagttgatgg aagcaaagtt     180

cttcttgacg acgatacaat tagccgtgtc tcaaaaaaac atacagctcg tgatggtgaa     240

tacggtgaat atggggaagc agttgaagat ggggaaaacg tcattaaaat catccgttca     300
```

-continued

```
gttcttcaat caggtgcttt accatcagtt ggtgttgatg aacttgacaa aattgattta    360

agttatgaaa caacagaatc aggggacaca gctgtttctg aagattcata tgataaatat    420

gcttcaaata atacaaataa agaaagatcc gaaaaaaaag tcatacacgg atgtaacttc    480

tcttcaaatg ttagttctaa acatactttt acagatagtt tagatatttc tttagttgat    540

gatagtgcac atatttcatg taacgtacat ttgtctgaac caaaatataa tcatttggta    600

ggtttaaatt gtcctggtga tattatacca gattgctttt ttcaagtata tcaacctgaa    660

tcagaagaac ttgaaccatc caacattgtt tatttagatt cacaaataaa tataggagat    720

attgaatatt atgaagatgc tgaaggagat gataaaatta aattatttgg tatagttgga    780

agtataccaa aaacgacatc ttttacttgt atatgtaaga aggataaaaa aagtgcttat    840

atgacagtta ctatagattc agca                                           864
```

<210> SEQ ID NO 17
<211> LENGTH: 436
<212> TYPE: PRT
<213> ORGANISM: Plasmodium falciparum
<220> FEATURE:
<221> NAME/KEY: Pfs230-Pfs48/45 Pro+I-6C protein sequence
<222> LOCATION: (1)..(1)

<400> SEQUENCE: 17

```
Glu Tyr Val Asp Glu Lys Glu Arg Gln Gly Glu Ile Tyr Pro Phe Gly
1               5                   10                  15

Asp Glu Glu Glu Lys Asp Glu Gly Gly Glu Ser Phe Thr Tyr Glu Lys
            20                  25                  30

Ser Glu Val Asp Lys Thr Asp Leu Phe Lys Phe Ile Glu Gly Gly Glu
        35                  40                  45

Gly Asp Asp Val Tyr Lys Val Asp Gly Ser Lys Val Leu Leu Asp Asp
    50                  55                  60

Asp Thr Ile Ser Arg Val Ser Lys Lys His Thr Ala Arg Asp Gly Glu
65                  70                  75                  80

Tyr Gly Glu Tyr Gly Glu Ala Val Glu Asp Gly Glu Asn Val Ile Lys
                85                  90                  95

Ile Ile Arg Ser Val Leu Gln Ser Gly Ala Leu Pro Ser Val Gly Val
            100                 105                 110

Asp Glu Leu Asp Lys Ile Asp Leu Ser Tyr Glu Thr Thr Glu Ser Gly
        115                 120                 125

Asp Thr Ala Val Ser Glu Asp Ser Tyr Asp Lys Tyr Ala Ser Asn Asn
    130                 135                 140

Thr Asn Lys Glu Arg Ser Tyr Val Cys Asp Phe Thr Asp Gln Leu Lys
145                 150                 155                 160

Pro Thr Glu Ser Gly Pro Lys Val Lys Lys Cys Glu Val Lys Val Asn
                165                 170                 175

Glu Pro Leu Ile Lys Val Lys Ile Ile Cys Pro Leu Lys Gly Ser Val
            180                 185                 190

Glu Lys Leu Tyr Asp Asn Ile Glu Tyr Val Pro Lys Lys Ser Pro Tyr
        195                 200                 205

Val Val Leu Thr Lys Glu Glu Thr Lys Leu Lys Glu Lys Leu Leu Ser
    210                 215                 220

Lys Leu Ile Tyr Gly Leu Leu Ile Ser Pro Thr Val Asn Glu Lys Glu
225                 230                 235                 240

Asn Asn Phe Lys Glu Gly Val Ile Glu Phe Thr Leu Pro Pro Val Val
                245                 250                 255
```

```
His Lys Ala Thr Val Phe Tyr Phe Ile Cys Asp Asn Ser Lys Thr Glu
            260                 265                 270

Asp Asp Asn Lys Lys Gly Asn Arg Gly Ile Val Glu Val Tyr Val Glu
        275                 280                 285

Pro Tyr Gly Asn Lys Ile Asn Gly Arg Ser Glu Lys Lys Val Ile His
    290                 295                 300

Gly Cys Asn Phe Ser Ser Asn Val Ser Ser Lys His Thr Phe Thr Asp
305                 310                 315                 320

Ser Leu Asp Ile Ser Leu Val Asp Asp Ser Ala His Ile Ser Cys Asn
                325                 330                 335

Val His Leu Ser Glu Pro Lys Tyr Asn His Leu Val Gly Leu Asn Cys
            340                 345                 350

Pro Gly Asp Ile Ile Pro Asp Cys Phe Phe Gln Val Tyr Gln Pro Glu
        355                 360                 365

Ser Glu Glu Leu Glu Pro Ser Asn Ile Val Tyr Leu Asp Ser Gln Ile
    370                 375                 380

Asn Ile Gly Asp Ile Glu Tyr Tyr Glu Asp Ala Glu Gly Asp Asp Lys
385                 390                 395                 400

Ile Lys Leu Phe Gly Ile Val Gly Ser Ile Pro Lys Thr Thr Ser Phe
                405                 410                 415

Thr Cys Ile Cys Lys Lys Asp Lys Lys Ser Ala Tyr Met Thr Val Thr
            420                 425                 430

Ile Asp Ser Ala
        435
```

<210> SEQ ID NO 18
<211> LENGTH: 1308
<212> TYPE: DNA
<213> ORGANISM: Plasmodium falciparum
<220> FEATURE:
<221> NAME/KEY: Pfs230-Pfs48/45 Pro+I-6C nucleic acid sequence
<222> LOCATION: (1)..(1)

<400> SEQUENCE: 18

```
gaatatgtcg acgaaaaaga acgtcaaggt gaaatttatc cattcggcga cgaagaagaa      60

aaagatgaag gtggtgaaag ctttacttat gaaaaatctg aagttgataa aactgatttg     120

tttaaattca tcgaaggcgg tgaaggtgac gacgtttata aagttgatgg aagcaaagtt     180

cttcttgacg acgatacaat tagccgtgtc tcaaaaaaac atacagctcg tgatggtgaa     240

tacggtgaat atggggaagc agttgaagat ggggaaaacg tcattaaaat catccgttca     300

gttcttcaat caggtgcttt accatcagtt ggtgttgatg aacttgacaa aattgattta     360

agttatgaaa caacagaatc aggggacaca gctgtttctg aagattcata tgataaatat     420

gcttcaaata atacaaataa agaaagatcc tacgtttgtg attttacaga tcaattaaaa     480

ccaacagaaa gtggtcctaa agtaaaaaaa tgtgaagtaa aagttaatga gccattaata     540

aaagtaaaaa taatatgtcc attaaaaggt tctgtagaaa aattatatga taatatagaa     600

tatgtaccta aaaaaagccc atatgttgtt ttaacaaaag aggaaactaa actaaaggaa     660

aaacttctct cgaaacttat ttatggttta ttaatatctc cgacggttaa cgaaaaggag     720

aataatttta aagaaggtgt tattgaattt actcttcccc ctgtggtaca caaggcaaca     780

gtgttttatt ttatatgtga taattcaaaa acagaagatg ataacaaaaa aggaaataga     840

gggattgtag aagtgtatgt agaaccatat ggtaataaaa ttaatggaag atccgaaaaa     900

aaagtcatac acggatgtaa cttctcttca aatgttagtt ctaaacatac ttttacagat     960
```

agtttagata tttctttagt tgatgatagt gcacatattt catgtaacgt acatttgtct 1020
gaaccaaaat ataatcattt ggtaggttta aattgtcctg gtgatattat accagattgc 1080
ttttttcaag tatatcaacc tgaatcagaa gaacttgaac catccaacat tgtttattta 1140
gattcacaaa taaatatagg agatattgaa tattatgaag atgctgaagg agatgataaa 1200
attaaattat ttggtatagt tggaagtata ccaaaaacga catcttttac ttgtatatgt 1260
aagaaggata aaaaaagtgc ttatatgaca gttactatag attcagca 1308

<210> SEQ ID NO 19
<211> LENGTH: 119
<212> TYPE: PRT
<213> ORGANISM: Artificial sequence
<220> FEATURE:
<223> OTHER INFORMATION: SpyCatcher protein sequence
<220> FEATURE:
<221> NAME/KEY: SpyCatcher protein sequence
<222> LOCATION: (1)..(1)

<400> SEQUENCE: 19

Gly Ala Met Val Asp Thr Leu Ser Gly Leu Ser Ser Glu Gln Gly Gln
1 5 10 15

Ser Gly Asp Met Thr Ile Glu Glu Asp Ser Ala Thr His Ile Lys Phe
20 25 30

Ser Lys Arg Asp Glu Asp Gly Lys Glu Leu Ala Gly Ala Thr Met Glu
35 40 45

Leu Arg Asp Ser Ser Gly Lys Thr Ile Ser Thr Trp Ile Ser Asp Gly
50 55 60

Gln Val Lys Asp Phe Tyr Leu Tyr Pro Gly Lys Tyr Thr Phe Val Glu
65 70 75 80

Thr Ala Ala Pro Asp Gly Tyr Glu Val Ala Thr Ala Ile Thr Phe Thr
85 90 95

Val Asn Glu Gln Gly Gln Val Thr Val Asn Gly Lys Ala Thr Lys Gly
100 105 110

Asp Ala His Ile Gly Gly Ser
115

<210> SEQ ID NO 20
<211> LENGTH: 357
<212> TYPE: DNA
<213> ORGANISM: Artificial sequence
<220> FEATURE:
<223> OTHER INFORMATION: SpyCatcher nucleic acid sequence
<220> FEATURE:
<221> NAME/KEY: SpyCatcher nucleic acid sequence
<222> LOCATION: (1)..(1)

<400> SEQUENCE: 20
ggtgcaatgg ttgataccct gagcggtctg agcagcgaac agggtcagag cggtgatatg 60
accattgaag aagatagcgc aacccacatc aaattcagca aacgtgatga agatggtaaa 120
gaactggcag gcgcaacaat ggaactgcgt gatagcagcg gtaaaaccat tagcacctgg 180
attagtgatg gtcaggtgaa agatttttat ctgtaccctg gcaaatacac ctttgttgaa 240
accgcagcac cggatggtta tgaagttgca accgcaatta cctttaccgt taatgaacag 300
ggccaggtta ccgtgaatgg taaagcaacc aaaggtgatg cacatattgg tggtagc 357

<210> SEQ ID NO 21
<211> LENGTH: 474
<212> TYPE: PRT
<213> ORGANISM: Plasmodium falciparum
<220> FEATURE:
<221> NAME/KEY: GLURP protein sequence
<222> LOCATION: (1)..(1)

<400> SEQUENCE: 21

```
Thr Ser Glu Asn Arg Asn Lys Arg Ile Gly Gly Pro Lys Leu Arg Gly
1               5                   10                  15

Asn Val Thr Ser Asn Ile Lys Phe Pro Ser Asp Asn Lys Gly Lys Ile
            20                  25                  30

Ile Arg Gly Ser Asn Asp Lys Leu Asn Lys Asn Ser Glu Asp Val Leu
        35                  40                  45

Glu Gln Ser Glu Lys Ser Leu Val Ser Glu Asn Val Pro Ser Gly Leu
    50                  55                  60

Asp Ile Asp Asp Ile Pro Lys Glu Ser Ile Phe Ile Gln Glu Asp Gln
65                  70                  75                  80

Glu Gly Gln Thr His Ser Glu Leu Asn Pro Glu Thr Ser Glu His Ser
                85                  90                  95

Lys Asp Leu Asn Asn Asn Gly Ser Lys Asn Glu Ser Ser Asp Ile Ile
            100                 105                 110

Ser Glu Asn Asn Lys Ser Asn Lys Val Gln Asn His Phe Glu Ser Leu
        115                 120                 125

Ser Asp Leu Glu Leu Leu Glu Asn Ser Ser Gln Asp Asn Leu Asp Lys
    130                 135                 140

Asp Thr Ile Ser Thr Glu Pro Phe Pro Asn Gln Lys His Lys Asp Leu
145                 150                 155                 160

Gln Gln Asp Leu Asn Asp Glu Pro Leu Glu Pro Phe Pro Thr Gln Ile
                165                 170                 175

His Lys Asp Tyr Lys Glu Lys Asn Leu Ile Asn Glu Glu Asp Ser Glu
            180                 185                 190

Pro Phe Pro Arg Gln Lys His Lys Lys Val Asp Asn His Asn Glu Glu
        195                 200                 205

Lys Asn Val Phe His Glu Asn Gly Ser Ala Asn Gly Asn Gln Gly Ser
    210                 215                 220

Leu Lys Leu Lys Ser Phe Asp Glu His Leu Lys Asp Glu Lys Ile Glu
225                 230                 235                 240

Asn Glu Pro Leu Val His Glu Asn Leu Ser Ile Pro Asn Asp Pro Ile
                245                 250                 255

Glu Gln Ile Leu Asn Gln Pro Glu Gln Glu Thr Asn Ile Gln Glu Gln
            260                 265                 270

Leu Tyr Asn Glu Lys Gln Asn Val Glu Glu Lys Gln Asn Ser Gln Ile
        275                 280                 285

Pro Ser Leu Asp Leu Lys Glu Pro Thr Asn Glu Asp Ile Leu Pro Asn
    290                 295                 300

His Asn Pro Leu Glu Asn Ile Lys Gln Ser Glu Ser Glu Ile Asn His
305                 310                 315                 320

Val Gln Asp His Ala Leu Pro Lys Glu Asn Ile Ile Asp Lys Leu Asp
                325                 330                 335

Asn Gln Lys Glu His Ile Asp Gln Ser Gln His Asn Ile Asn Val Leu
            340                 345                 350

Gln Glu Asn Asn Ile Asn Asn His Gln Leu Glu Pro Gln Glu Lys Pro
        355                 360                 365

Asn Ile Glu Ser Phe Glu Pro Lys Asn Ile Asp Ser Glu Ile Ile Leu
    370                 375                 380

Pro Glu Asn Val Glu Thr Glu Glu Ile Ile Asp Asp Val Pro Ser Pro
```

-continued

```
385                 390                 395                 400

Lys His Ser Asn His Glu Thr Phe Glu Glu Glu Thr Ser Glu Ser Glu
                405                 410                 415

His Glu Glu Ala Val Ser Glu Lys Asn Ala His Glu Thr Val Glu His
            420                 425                 430

Glu Glu Thr Val Ser Gln Glu Ser Asn Pro Glu Lys Ala Asp Asn Asp
        435                 440                 445

Gly Asn Val Ser Gln Asn Ser Asn Asn Glu Leu Asn Glu Asn Glu Phe
    450                 455                 460

Val Glu Ser Glu Lys Ser Glu His Glu Ala
465                 470
```

<210> SEQ ID NO 22
<211> LENGTH: 1422
<212> TYPE: DNA
<213> ORGANISM: Plasmodium falciparum
<220> FEATURE:
<221> NAME/KEY: GLURP nucleic acid sequence
<222> LOCATION: (1)..(1)

<400> SEQUENCE: 22

```
acaagtgaga atagaaataa acgaatcggg ggtcctaaat taaggggtaa tgttacaagt     60

aatataaagt tcccatcaga taacaaaggt aaaattataa gaggttcgaa tgataaactt    120

aataaaaact ctgaagatgt tttagaacaa agcgaaaaat cgcttgtttc agaaaatgtt    180

cctagtggat tagatataga tgatatccct aaagaatcta tttttattca agaagatcaa    240

gaaggtcaaa ctcattctga attaaatcct gaaacatcag aacatagtaa agatttaaat    300

aataatggtt caaaaaatga atctagtgat attatttcag aaaataataa atcaaataaa    360

gtacaaaatc attttgaatc attatcagat ttagaattac ttgaaaattc ctcacaagat    420

aatttagaca aagatacaat ttcaacagaa cctttttccta atcaaaaaca taaagactta    480

caacaagatt taaatgatga acctttagaa ccctttccta cacaaataca taaagattat    540

aaagaaaaaa atttaataaa tgaagaagat tcagaaccat ttcccagaca aaagcataaa    600

aaggtagaca atcataatga agaaaaaaac gtatttcatg aaaatggttc tgcaaatggt    660

aatcaaggaa gtttgaaact taaatcattc gatgaacatt taaaagatga aaaaatagaa    720

aatgaaccac ttgttcatga aaatttatcc ataccaaatg atccaataga acaaatatta    780

aatcaacctg aacaagaaac aaatatccag gaacaattgt ataatgaaaa acaaaatgtt    840

gaagaaaaac aaaattctca aataccttcg ttagatttaa aagaaccaac aaatgaagat    900

attttaccaa atcataatcc attagaaaat ataaaacaaa gtgaatcaga aataaatcat    960

gtacaagatc atgcgctacc aaaagagaat ataatagaca aacttgataa tcaaaaagaa   1020

cacatcgatc aatcacaaca taatataaat gtattacaag aaaataacat aaacaatcac   1080

caattagaac ctcaagagaa acctaatatt gaatcgtttg aacctaaaaa tatagattca   1140

gaaattattc ttcctgaaaa tgttgaaaca gaagaaataa tagatgatgt gccttcccct   1200

aaacattcta accatgaaac atttgaagaa gaaacaagtg aatctgaaca tgaagaagcc   1260

gtatctgaaa aaaatgccca cgaaactgtc gaacatgaag aaactgtgtc tcaagaaagc   1320

aatcctgaaa aagctgataa tgatggaaat gtatctcaaa acagcaacaa cgaattaaat   1380

gaaaatgaat tcgttgaatc ggaaaaaagc gagcatgaag ca                      1422
```

<210> SEQ ID NO 23
<211> LENGTH: 16

<212> TYPE: PRT
<213> ORGANISM: Artificial sequence
<220> FEATURE:
<223> OTHER INFORMATION: SpyTag protein sequence
<220> FEATURE:
<221> NAME/KEY: SpyTag protein sequence
<222> LOCATION: (1)..(1)

<400> SEQUENCE: 23

Ala His Ile Val Met Val Asp Ala Tyr Lys Pro Thr Lys Gly Gly Ser
1 5 10 15

<210> SEQ ID NO 24
<211> LENGTH: 48
<212> TYPE: DNA
<213> ORGANISM: Artificial sequence
<220> FEATURE:
<223> OTHER INFORMATION: SpyTag nucleic acid sequence
<220> FEATURE:
<221> NAME/KEY: SpyTag nucleic acid sequence
<222> LOCATION: (1)..(1)

<400> SEQUENCE: 24
gctcatattg ttatggttga tgcttataaa cctactaaag gtggatca 48

<210> SEQ ID NO 25
<211> LENGTH: 222
<212> TYPE: PRT
<213> ORGANISM: Plasmodium falciparum
<220> FEATURE:
<221> NAME/KEY: CSP protein sequence
<222> LOCATION: (1)..(1)

<400> SEQUENCE: 25

Gly Ser Ser Ser Asn Thr Arg Val Leu Asn Glu Leu Asn Tyr Asp Asn
1 5 10 15

Ala Gly Thr Asn Leu Tyr Asn Glu Leu Glu Met Asn Tyr Tyr Gly Lys
20 25 30

Gln Glu Asn Trp Tyr Ser Leu Lys Lys Asn Ser Arg Ser Leu Gly Glu
35 40 45

Asn Asp Asp Gly Asn Asn Glu Asp Asn Glu Lys Leu Arg Lys Pro Lys
50 55 60

His Lys Lys Leu Lys Gln Pro Ala Asp Gly Asn Pro Asp Pro Asn Ala
65 70 75 80

Asn Pro Asn Val Asp Pro Asn Ala Asn Pro Asn Val Asp Pro Asn Ala
85 90 95

Asn Pro Asn Val Asp Pro Asn Ala Asn Pro Asn Ala Asn Pro Asn Ala
100 105 110

Asn Pro Asn Ala Asn Pro Asn Ala Asn Pro Asn Ala Asn Pro Asn Ala
115 120 125

Asn Pro Asn Ala Asn Pro Asn Ala Asn Pro Asn Ala Asn Pro Asn Ala
130 135 140

Asn Pro Asn Ala Asn Pro Asn Ala Asn Pro Asn Ala Asn Pro Asn Ala
145 150 155 160

Asn Pro Asn Ala Asn Pro Asn Lys Asn Asn Gln Gly Asn Gly Gln Gly
165 170 175

His Asn Met Pro Asn Asp Pro Asn Arg Asn Val Asp Glu Asn Ala Asn
180 185 190

Ala Asn Ser Ala Val Lys Asn Asn Asn Asn Glu Glu Pro Ser Asp Lys
195 200 205

His Ile Lys Glu Tyr Leu Asn Lys Ile Gln Asn Ser Leu Ser 210 215 220

<210> SEQ ID NO 26
<211> LENGTH: 666
<212> TYPE: DNA
<213> ORGANISM: Plasmodium falciparum
<220> FEATURE:
<221> NAME/KEY: CSP nucleic acid sequence
<222> LOCATION: (1)..(1)

<400> SEQUENCE: 26
ggttcatcat caaatacccg tgttcttaac gaacttaact atgataatgc cggtacaaat 60
ctttataatg aacttgaaat gaattattac ggtaaacaag aaaattggta ttcattgaaa 120
aaaaactcac gttcacttgg tgaaaatgac gacgggaata atgaagataa tgaaaaactt 180
cgtaaaccaa aacataaaaa acttaaacaa ccagccgacg gaaatccaga tccaaatgct 240
aatccaaatg ttgaccctaa cgccaatcct aatgtagacc caaatgcaaa ccctaacgtt 300
gatcctaatg ctaacccaaa cgccaatcca aacgcaaatc ctaatgccaa tccaaacgct 360
aaccctaacg ctaacccaaa tgctaatcct aatgcaaacc ctaatgcaaa tccaaatgcc 420
aatcctaacg caaatccaaa cgcaaaccca aatgcaaacc ctaatgctaa cccaaatgca 480
aacccaaacg ctaatcctaa caaaaacaat caaggtaatg gtcaagggca caatatgcca 540
aatgatccaa atcgtaatgt tgatgaaaat gccaacgcta actcagccgt taaaaacaac 600
aataacgaag aaccatcaga taaacatatt aaagaatatc ttaacaaaat tcaaaattca 660
ctttca 666

<210> SEQ ID NO 27
<211> LENGTH: 172
<212> TYPE: PRT
<213> ORGANISM: Plasmodium falciparum
<220> FEATURE:
<221> NAME/KEY: MSP3 protein sequence
<222> LOCATION: (1)..(1)

<400> SEQUENCE: 27

Lys Ala Lys Glu Ala Ser Ser Tyr Asp Tyr Ile Leu Gly Trp Glu Phe
1 5 10 15

Gly Gly Gly Val Pro Glu His Lys Lys Glu Glu Asn Met Leu Ser His
20 25 30

Leu Tyr Val Ser Ser Lys Asp Lys Glu Asn Ile Ser Lys Glu Asn Asp
35 40 45

Asp Val Leu Asp Glu Lys Glu Glu Glu Ala Glu Glu Thr Glu Glu Glu
50 55 60

Glu Leu Glu Glu Lys Asn Glu Glu Glu Thr Glu Ser Glu Ile Ser Glu
65 70 75 80

Asp Glu Glu Glu Glu Glu Glu Glu Glu Glu Lys Glu Glu Glu Asn Asp
85 90 95

Lys Lys Lys Glu Gln Glu Lys Glu Gln Ser Asn Glu Asn Asn Asp Gln
100 105 110

Lys Lys Asp Met Glu Ala Gln Asn Leu Ile Ser Lys Asn Gln Asn Asn
115 120 125

Asn Glu Lys Asn Val Lys Glu Ala Ala Glu Ser Ile Met Lys Thr Leu
130 135 140

Ala Gly Leu Ile Lys Gly Asn Asn Gln Ile Asp Ser Thr Leu Lys Asp
145 150 155 160

Leu Val Glu Glu Leu Ser Lys Tyr Phe Lys Asn His 165 170

<210> SEQ ID NO 28
<211> LENGTH: 516
<212> TYPE: DNA
<213> ORGANISM: Plasmodium falciparum
<220> FEATURE:
<221> NAME/KEY: MSP3 nucleic acid sequence
<222> LOCATION: (1)..(1)

<400> SEQUENCE: 28
aaagcaaaag aagcttctag ttatgattat attttaggtt gggaatttgg aggaggcgtt 60
ccagaacaca aaaaagaaga aaatatgtta tcacatttat atgtttcttc aaaggataag 120
gaaaatatat ctaaggaaaa tgatgatgta ttagatgaga aggaagaaga ggcagaagaa 180
acagaagaag aagaacttga agaaaaaaat gaagaagaaa cagaatcaga aataagtgaa 240
gatgaagaag aagaagaaga agaagaagaa aaggaagaag aaaatgacaa aaaaaaagaa 300
caagaaaaag aacaaagtaa tgaaaataat gatcaaaaaa aagatatgga agcacagaat 360
ttaatttcta aaaaccagaa taataatgag aaaaacgtaa aagaagctgc tgaaagcatc 420
atgaaaactt tagctggttt aatcaaggga aataatcaaa tagattctac cttaaaagat 480
ttagtagaag aattatccaa atattttaaa aatcat 516

<210> SEQ ID NO 29
<211> LENGTH: 33
<212> TYPE: PRT
<213> ORGANISM: Artificial sequence
<220> FEATURE:
<223> OTHER INFORMATION: Pfs230 Pro domain forward primer
<220> FEATURE:
<221> NAME/KEY: Pfs230 Pro domain forward primer
<222> LOCATION: (1)..(1)

<400> SEQUENCE: 29

Gly Ala Ala Thr Gly Gly Ala Thr Cys Cys Gly Ala Ala Thr Ala Thr
1 5 10 15

Gly Thr Cys Gly Ala Cys Gly Ala Ala Ala Ala Ala Gly Ala Ala Cys
20 25 30

Gly

<210> SEQ ID NO 30
<211> LENGTH: 34
<212> TYPE: DNA
<213> ORGANISM: Artificial sequence
<220> FEATURE:
<223> OTHER INFORMATION: Pfs230 Pro domain reverse primer
<220> FEATURE:
<221> NAME/KEY: Pfs230 Pro domain reverse primer
<222> LOCATION: (1)..(1)

<400> SEQUENCE: 30
gaatagatct ttctttattt gtattatttg aagc 34

<210> SEQ ID NO 31
<211> LENGTH: 42
<212> TYPE: DNA
<213> ORGANISM: Artificial sequence
<220> FEATURE:
<223> OTHER INFORMATION: Pfs230 domain I forward primer
<220> FEATURE:
<221> NAME/KEY: Pfs230 domain I forward primer
<222> LOCATION: (1)..(1)

<400> SEQUENCE: 31
gaatggatcc tacgtttgtg attttacaga tcaattaaaa cc 42

<210> SEQ ID NO 32
<211> LENGTH: 34
<212> TYPE: DNA
<213> ORGANISM: Artificial sequence
<220> FEATURE:
<223> OTHER INFORMATION: Pfs230 domain I reverse primer
<220> FEATURE:
<221> NAME/KEY: Pfs230 domain I reverse primer
<222> LOCATION: (1)..(1)

<400> SEQUENCE: 32
gaatagatct tccattaatt ttattaccat atgg 34

<210> SEQ ID NO 33
<211> LENGTH: 51
<212> TYPE: DNA
<213> ORGANISM: Artificial sequence
<220> FEATURE:
<223> OTHER INFORMATION: Pfs230 domain II forward primer
<220> FEATURE:
<221> NAME/KEY: Pfs230 domain II forward primer
<222> LOCATION: (1)..(1)

<400> SEQUENCE: 33
gaatggatcc tgtgctttct tggatgaaga tgaagaagaa gaaaaatatg g 51

<210> SEQ ID NO 34
<211> LENGTH: 40
<212> TYPE: DNA
<213> ORGANISM: Artificial sequence
<220> FEATURE:
<223> OTHER INFORMATION: Pfs230 domain II reverse primer
<220> FEATURE:
<221> NAME/KEY: Pfs230 domain II reverse primer
<222> LOCATION: (1)..(1)

<400> SEQUENCE: 34
gaatagatct atgttcttta ttatttacat tcttttgagc 40

<210> SEQ ID NO 35
<211> LENGTH: 49
<212> TYPE: DNA
<213> ORGANISM: Artificial sequence
<220> FEATURE:
<223> OTHER INFORMATION: Pfs230 domain III forward primer
<220> FEATURE:
<221> NAME/KEY: Pfs230 domain III forward primer
<222> LOCATION: (1)..(1)

<400> SEQUENCE: 35
gaatagatct gattatacat gtgattttac cgataaatta gataaaacg 49

<210> SEQ ID NO 36
<211> LENGTH: 40
<212> TYPE: DNA
<213> ORGANISM: Artificial sequence
<220> FEATURE:
<223> OTHER INFORMATION: Pfs230 domain III reverse primer
<220> FEATURE:
<221> NAME/KEY: Pfs230 domain III reverse primer
<222> LOCATION: (1)..(1)

<400> SEQUENCE: 36
gaatggatcc ttgcttagat attaataatt caacaattcc 40

<210> SEQ ID NO 37
<211> LENGTH: 45
<212> TYPE: DNA
<213> ORGANISM: Artificial sequence
<220> FEATURE:
<223> OTHER INFORMATION: Pfs48/45 10C domain forward primer
<220> FEATURE:
<221> NAME/KEY: Pfs48/45 10C domain forward primer
<222> LOCATION: (1)..(1)

<400> SEQUENCE: 37
caatggatcc gataatactg aaaaggttat atcaagtata gaagg 45

<210> SEQ ID NO 38
<211> LENGTH: 40
<212> TYPE: DNA
<213> ORGANISM: Artificial sequence
<220> FEATURE:
<223> OTHER INFORMATION: Pfs48/45 10C domain reverse primer
<220> FEATURE:
<221> NAME/KEY: Pfs48/45 10C domain reverse primer
<222> LOCATION: (1)..(1)

<400> SEQUENCE: 38
ccatagatct tgctgaatct atagtaactg tcatataagc 40

<210> SEQ ID NO 39
<211> LENGTH: 40
<212> TYPE: DNA
<213> ORGANISM: Artificial sequence
<220> FEATURE:
<223> OTHER INFORMATION: Pfs48/45 6C domain forward primer
<220> FEATURE:
<221> NAME/KEY: Pfs48/45 6C domain forward primer
<222> LOCATION: (1)..(1)

<400> SEQUENCE: 39
ccatggatcc gaaaaaaaag tcatacacgg atgtaacttc 40

<210> SEQ ID NO 40
<211> LENGTH: 40
<212> TYPE: DNA
<213> ORGANISM: Artificial sequence
<220> FEATURE:
<223> OTHER INFORMATION: Pfs48/45 6C domain reverse primer
<220> FEATURE:
<221> NAME/KEY: Pfs48/45 6C domain reverse primer
<222> LOCATION: (1)..(1)

<400> SEQUENCE: 40
ccatagatct tgctgaatct atagtaactg tcatataagc 40

<210> SEQ ID NO 41
<211> LENGTH: 11
<212> TYPE: PRT
<213> ORGANISM: Artificial sequence
<220> FEATURE:
<223> OTHER INFORMATION: Linker to SpyTag
<220> FEATURE:
<221> NAME/KEY: Linker to SpyTag
<222> LOCATION: (1)..(1)

<400> SEQUENCE: 41

Gly Ser Gly Thr Ala Gly Gly Gly Ser Gly Ser
1 5 10

<210> SEQ ID NO 42
<211> LENGTH: 14
<212> TYPE: PRT

<213> ORGANISM: Artificial sequence
<220> FEATURE:
<223> OTHER INFORMATION: Linker Flex2 protein sequence

<400> SEQUENCE: 42

Gly Gly Gly Gly Ser Gly Gly Gly Gly Ser Gly Gly Gly Gly
1               5                   10

<210> SEQ ID NO 43
<211> LENGTH: 45
<212> TYPE: DNA
<213> ORGANISM: Artificial sequence
<220> FEATURE:
<223> OTHER INFORMATION: Linker Flex2 nucleic acid sequence

<400> SEQUENCE: 43
ggcggaggcg gttcaggtgg tggtggaagc ggaggtggtg gatca 45

<210> SEQ ID NO 44
<211> LENGTH: 57
<212> TYPE: PRT
<213> ORGANISM: Artificial sequence
<220> FEATURE:
<223> OTHER INFORMATION: Linker CsTSR protein sequence

<400> SEQUENCE: 44

Tyr Leu Asn Lys Ile Gln Asn Ser Leu Ser Thr Glu Trp Ser Pro Cys
1               5                   10                  15

Ser Val Thr Cys Gly Asn Gly Ile Gln Val Arg Ile Lys Pro Gly Ser
            20                  25                  30

Ala Asn Lys Pro Lys Asp Glu Leu Asp Tyr Ala Asn Asp Ile Glu Lys
        35                  40                  45

Lys Ile Cys Lys Met Glu Lys Cys Ser
    50                  55

<210> SEQ ID NO 45
<211> LENGTH: 171
<212> TYPE: DNA
<213> ORGANISM: Artificial sequence
<220> FEATURE:
<223> OTHER INFORMATION: Linker CsTSR nucleic acid sequence

<400> SEQUENCE: 45
tatcttaaca aaattcaaaa ttcactttca acagaatggt caccatgttc agttacatgt 60
ggtaatggta ttcaagttcg tatcaaacca gggtcagcca ataaacctaa agacgaattg 120
gattacgcca atgatattga aaaaaaaatt tgtaaaatgg aaaaatgttc a 171

<210> SEQ ID NO 46
<211> LENGTH: 27
<212> TYPE: PRT
<213> ORGANISM: Artificial sequence
<220> FEATURE:
<223> OTHER INFORMATION: Linker CsLNK protein sequence

<400> SEQUENCE: 46

Asn Met Pro Asn Asp Pro Asn Arg Asn Val Asp Glu Asn Ala Asn Ala
1               5                   10                  15

Asn Ser Ala Val Lys Asn Asn Asn Asn Glu Glu
            20                  25

<210> SEQ ID NO 47
<211> LENGTH: 81
<212> TYPE: DNA

<213> ORGANISM: Artificial sequence
<220> FEATURE:
<223> OTHER INFORMATION: Linker CsLNK nucleic acid sequence

<400> SEQUENCE: 47
aacatgccaa atgatccaaa tcgtaatgtt gacgaaaatg ccaatgctaa ctcagccgtt 60
aaaaacaata acaatgaaga a 81

<210> SEQ ID NO 48
<211> LENGTH: 36
<212> TYPE: PRT
<213> ORGANISM: Artificial sequence
<220> FEATURE:
<223> OTHER INFORMATION: Linker Cs3 protein sequence

<400> SEQUENCE: 48

Asn Ala Asn Pro Asn Val Asp Pro Asn Ala Asn Pro Asn Val Asp Pro
1 5 10 15

Asn Ala Asn Pro Asn Val Asp Pro Asn Ala Asn Pro Asn Ala Asn Pro
20 25 30

Asn Ala Asn Pro
35

<210> SEQ ID NO 49
<211> LENGTH: 108
<212> TYPE: DNA
<213> ORGANISM: Artificial sequence
<220> FEATURE:
<223> OTHER INFORMATION: Linker Cs3 nucleic acid sequence

<400> SEQUENCE: 49
aatgctaatc caaatgttga tccaaatgca aatcctaacg tagacccaaa cgcaaaccct 60
aatgtcgatc ctaacgccaa tccaaatgct aaccctaatg ctaatcct 108

<210> SEQ ID NO 50
<211> LENGTH: 16
<212> TYPE: PRT
<213> ORGANISM: Artificial sequence
<220> FEATURE:
<223> OTHER INFORMATION: Linker Sol protein sequence

<400> SEQUENCE: 50

Ser Gly Ser Val Ser Ser Glu Gln Leu Ala Gln Phe Arg Ser Leu Asp
1 5 10 15

<210> SEQ ID NO 51
<211> LENGTH: 54
<212> TYPE: DNA
<213> ORGANISM: Artificial sequence
<220> FEATURE:
<223> OTHER INFORMATION: Linker Sol nucleic acid sequence

<400> SEQUENCE: 51
aaagaatcag gttcagtttc atcagaacaa cttgcccaat ttcgtagctt ggac 54

<210> SEQ ID NO 52
<211> LENGTH: 301
<212> TYPE: PRT
<213> ORGANISM: Artificial sequence
<220> FEATURE:
<223> OTHER INFORMATION: Pro(Flex2)-6C protein sequence

<400> SEQUENCE: 52

Glu Tyr Val Asp Glu Lys Glu Arg Gln Gly Glu Ile Tyr Pro Phe Gly

```
1               5                   10                  15

Asp Glu Glu Glu Lys Asp Glu Gly Gly Glu Ser Phe Thr Tyr Glu Lys
            20                  25                  30

Ser Glu Val Asp Lys Thr Asp Leu Phe Lys Phe Ile Glu Gly Gly Glu
        35                  40                  45

Gly Asp Asp Val Tyr Lys Val Asp Gly Ser Lys Val Leu Leu Asp Asp
    50                  55                  60

Asp Thr Ile Ser Arg Val Ser Lys Lys His Thr Ala Arg Asp Gly Glu
65                  70                  75                  80

Tyr Gly Glu Tyr Gly Glu Ala Val Glu Asp Gly Glu Asn Val Ile Lys
                85                  90                  95

Ile Ile Arg Ser Val Leu Gln Ser Gly Ala Leu Pro Ser Val Gly Val
            100                 105                 110

Asp Glu Leu Asp Lys Ile Asp Leu Ser Tyr Glu Thr Thr Glu Ser Gly
        115                 120                 125

Asp Thr Ala Val Ser Glu Asp Ser Tyr Asp Lys Tyr Ala Ser Asn Asn
    130                 135                 140

Thr Asn Lys Glu Gly Gly Gly Gly Ser Gly Gly Gly Gly Ser Gly Gly
145                 150                 155                 160

Gly Gly Ser Glu Lys Lys Val Ile His Gly Cys Asn Phe Ser Ser Asn
                165                 170                 175

Val Ser Ser Lys His Thr Phe Thr Asp Ser Leu Asp Ile Ser Leu Val
            180                 185                 190

Asp Asp Ser Ala His Ile Ser Cys Asn Val His Leu Ser Glu Pro Lys
        195                 200                 205

Tyr Asn His Leu Val Gly Leu Asn Cys Pro Gly Asp Ile Ile Pro Asp
    210                 215                 220

Cys Phe Phe Gln Val Tyr Gln Pro Glu Ser Glu Glu Leu Glu Pro Ser
225                 230                 235                 240

Asn Ile Val Tyr Leu Asp Ser Gln Ile Asn Ile Gly Asp Ile Glu Tyr
                245                 250                 255

Tyr Glu Asp Ala Glu Gly Asp Asp Lys Ile Lys Leu Phe Gly Ile Val
            260                 265                 270

Gly Ser Ile Pro Lys Thr Thr Ser Phe Thr Cys Ile Cys Lys Lys Asp
        275                 280                 285

Lys Lys Ser Ala Tyr Met Thr Val Thr Ile Asp Ser Ala
    290                 295                 300
```

<210> SEQ ID NO 53
<211> LENGTH: 903
<212> TYPE: DNA
<213> ORGANISM: Artificial sequence
<220> FEATURE:
<223> OTHER INFORMATION: Pro(Flex2)-6C nucleic acid sequence

<400> SEQUENCE: 53

```
gaatacgttg atgaaaaaga acgtcaaggt gaaatttatc cattcggcga cgaagaagaa     60

aaagatgaag gtggtgaaag ctttacatat gaaaaatcag aagttgataa aactgatttg    120

tttaaattca tcgaaggcgg tgaaggtgac gacgtttata aagttgatgg gtcaaaagtt    180

cttcttgacg acgatacaat ttcacgtgtt agcaaaaaac atacagctcg tgatggtgaa    240

tacggtgaat atggggaagc tgttgaagat ggggaaaacg tcattaaaat catccgttca    300

gttcttcaat caggtgcttt accatcagtt ggtgttgatg aacttgacaa aatcgatctt    360

tcatacgaaa caacagaatc aggtgataca gccgtttcag aagattcata cgataaatac    420
```

```
gcctcaaata atacaaataa agaaggcgga ggcggttcag gtggtggtgg aagcggaggt    480

ggtggatcag aaaaaaaagt tattcacggg tgtaattttt catctaatgt ttcatcaaaa    540

catactttta cagattcact tgatatttca cttgttgacg actcagccca catttcatgt    600

aatgtccatc ttagcgaacc aaaatacaat caccttgttg ggcttaattg tccaggtgat    660

attattccag actgtttttt tcaagtttac caaccagaat cagaagaatt ggaaccatca    720

aacattgttt atcttgattc acaaatcaat attggtgata ttgaatacta tgaagatgcc    780

gaaggggatg ataaaatcaa actttttggt atcgtcggtt caattccaaa aaccacctca    840

ttcacctgta tttgtaaaaa agacaaaaaa tcagcttata tgacagttac aatcgactca    900

gct                                                                  903


<210> SEQ ID NO 54
<211> LENGTH: 343
<212> TYPE: PRT
<213> ORGANISM: Artificial sequence
<220> FEATURE:
<223> OTHER INFORMATION: Pro(CsTSR)-6C protein sequence

<400> SEQUENCE: 54

Glu Tyr Val Asp Glu Lys Glu Arg Gln Gly Glu Ile Tyr Pro Phe Gly
1               5                   10                  15

Asp Glu Glu Glu Lys Asp Glu Gly Gly Glu Ser Phe Thr Tyr Glu Lys
            20                  25                  30

Ser Glu Val Asp Lys Thr Asp Leu Phe Lys Phe Ile Glu Gly Gly Glu
        35                  40                  45

Gly Asp Asp Val Tyr Lys Val Asp Gly Ser Lys Val Leu Leu Asp Asp
    50                  55                  60

Asp Thr Ile Ser Arg Val Ser Lys Lys His Thr Ala Arg Asp Gly Glu
65                  70                  75                  80

Tyr Gly Glu Tyr Gly Glu Ala Val Glu Asp Gly Glu Asn Val Ile Lys
                85                  90                  95

Ile Ile Arg Ser Val Leu Gln Ser Gly Ala Leu Pro Ser Val Gly Val
            100                 105                 110

Asp Glu Leu Asp Lys Ile Asp Leu Ser Tyr Glu Thr Thr Glu Ser Gly
        115                 120                 125

Asp Thr Ala Val Ser Glu Asp Ser Tyr Asp Lys Tyr Ala Ser Asn Asn
    130                 135                 140

Thr Asn Lys Glu Tyr Leu Asn Lys Ile Gln Asn Ser Leu Ser Thr Glu
145                 150                 155                 160

Trp Ser Pro Cys Ser Val Thr Cys Gly Asn Gly Ile Gln Val Arg Ile
                165                 170                 175

Lys Pro Gly Ser Ala Asn Lys Pro Lys Asp Glu Leu Asp Tyr Ala Asn
            180                 185                 190

Asp Ile Glu Lys Lys Ile Cys Lys Met Glu Lys Cys Ser Glu Lys Lys
        195                 200                 205

Val Ile His Gly Cys Asn Phe Ser Ser Asn Val Ser Ser Lys His Thr
    210                 215                 220

Phe Thr Asp Ser Leu Asp Ile Ser Leu Val Asp Asp Ser Ala His Ile
225                 230                 235                 240

Ser Cys Asn Val His Leu Ser Glu Pro Lys Tyr Asn His Leu Val Gly
                245                 250                 255

Leu Asn Cys Pro Gly Asp Ile Ile Pro Asp Cys Phe Phe Gln Val Tyr
            260                 265                 270
```

Gln Pro Glu Ser Glu Glu Leu Glu Pro Ser Asn Ile Val Tyr Leu Asp
        275                 280                 285

Ser Gln Ile Asn Ile Gly Asp Ile Glu Tyr Tyr Glu Asp Ala Glu Gly
    290                 295                 300

Asp Asp Lys Ile Lys Leu Phe Gly Ile Val Gly Ser Ile Pro Lys Thr
305                 310                 315                 320

Thr Ser Phe Thr Cys Ile Cys Lys Lys Asp Lys Lys Ser Ala Tyr Met
                325                 330                 335

Thr Val Thr Ile Asp Ser Ala
            340

<210> SEQ ID NO 55
<211> LENGTH: 1029
<212> TYPE: DNA
<213> ORGANISM: Artificial sequence
<220> FEATURE:
<223> OTHER INFORMATION: Pro(CsTSR)-6C nucleic acid sequence

<400> SEQUENCE: 55
gaatacgttg atgaaaaaga acgtcaaggt gaaatttatc cattcggcga cgaagaagaa 60
aaagatgaag gtggtgaaag ctttacatat gaaaaatcag aagttgataa aactgatttg 120
tttaaattca tcgaaggcgg tgaaggtgac gacgtttata aagttgatgg gtcaaaagtt 180
cttcttgacg acgatacaat ttcacgtgtt agcaaaaaac atacagctcg tgatggtgaa 240
tacggtgaat atggggaagc tgttgaagat ggggaaaacg tcattaaaat catccgttca 300
gttcttcaat caggtgcttt accatcagtt ggtgttgatg aacttgacaa aatcgatctt 360
tcatacgaaa caacagaatc aggtgataca gccgtttcag aagattcata cgataaatac 420
gcctcaaata atacaaataa agaatatctt aacaaaattc aaaattcact ttcaacagaa 480
tggtcaccat gttcagttac atgtggtaat ggtattcaag ttcgtatcaa accagggtca 540
gccaataaac ctaaagacga attggattac gccaatgata ttgaaaaaaa aatttgtaaa 600
atggaaaaat gttcagaaaa aaaagttatt catggttgta atttttcatc taatgtttca 660
tcaaaacata cttttacaga ttcacttgat atttcacttg ttgacgactc agcccacatt 720
tcatgtaatg tccatcttag cgaaccaaaa tacaatcacc ttgttgggct taattgtcca 780
ggtgatatta ttccagactg ttttttccaa gtttatcaac cagaatcaga agaattggaa 840
ccatcaaaca ttgtttatct tgattcacaa atcaatattg gagatattga atactatgaa 900
gatgccgaag ggatgataa aatcaaactt tttggtatcg tcggttcaat tccaaaaacc 960
acctcattca cctgtatttg taaaaaagac aaaaaatcag cttatatgac agttacaatc 1020
gactcagct 1029

<210> SEQ ID NO 56
<211> LENGTH: 313
<212> TYPE: PRT
<213> ORGANISM: Artificial sequence
<220> FEATURE:
<223> OTHER INFORMATION: Pro(CsLNK)-6C protein sequence

<400> SEQUENCE: 56

Glu Tyr Val Asp Glu Lys Glu Arg Gln Gly Glu Ile Tyr Pro Phe Gly
1               5                   10                  15

Asp Glu Glu Glu Lys Asp Glu Gly Gly Glu Ser Phe Thr Tyr Glu Lys
            20                  25                  30

Ser Glu Val Asp Lys Thr Asp Leu Phe Lys Phe Ile Glu Gly Gly Glu

-continued

```
        35                  40                  45

Gly Asp Asp Val Tyr Lys Val Asp Gly Ser Lys Val Leu Leu Asp Asp
    50                  55                  60

Asp Thr Ile Ser Arg Val Ser Lys Lys His Thr Ala Arg Asp Gly Glu
65                  70                  75                  80

Tyr Gly Glu Tyr Gly Glu Ala Val Glu Asp Gly Glu Asn Val Ile Lys
                85                  90                  95

Ile Ile Arg Ser Val Leu Gln Ser Gly Ala Leu Pro Ser Val Gly Val
            100                 105                 110

Asp Glu Leu Asp Lys Ile Asp Leu Ser Tyr Glu Thr Thr Glu Ser Gly
        115                 120                 125

Asp Thr Ala Val Ser Glu Asp Ser Tyr Asp Lys Tyr Ala Ser Asn Asn
    130                 135                 140

Thr Asn Lys Glu Asn Met Pro Asn Asp Pro Asn Arg Asn Val Asp Glu
145                 150                 155                 160

Asn Ala Asn Ala Asn Ser Ala Val Lys Asn Asn Asn Asn Glu Glu Glu
                165                 170                 175

Lys Lys Val Ile His Gly Cys Asn Phe Ser Ser Asn Val Ser Ser Lys
            180                 185                 190

His Thr Phe Thr Asp Ser Leu Asp Ile Ser Leu Val Asp Asp Ser Ala
        195                 200                 205

His Ile Ser Cys Asn Val His Leu Ser Glu Pro Lys Tyr Asn His Leu
    210                 215                 220

Val Gly Leu Asn Cys Pro Gly Asp Ile Ile Pro Asp Cys Phe Phe Gln
225                 230                 235                 240

Val Tyr Gln Pro Glu Ser Glu Glu Leu Glu Pro Ser Asn Ile Val Tyr
                245                 250                 255

Leu Asp Ser Gln Ile Asn Ile Gly Asp Ile Glu Tyr Tyr Glu Asp Ala
            260                 265                 270

Glu Gly Asp Asp Lys Ile Lys Leu Phe Gly Ile Val Gly Ser Ile Pro
        275                 280                 285

Lys Thr Thr Ser Phe Thr Cys Ile Cys Lys Lys Asp Lys Lys Ser Ala
    290                 295                 300

Tyr Met Thr Val Thr Ile Asp Ser Ala
305                 310
```

<210> SEQ ID NO 57
<211> LENGTH: 939
<212> TYPE: DNA
<213> ORGANISM: Artificial sequence
<220> FEATURE:
<223> OTHER INFORMATION: Pro(CsLNK)-6C nucleic acid sequence

<400> SEQUENCE: 57

```
gaatacgttg atgaaaaaga acgtcaaggt gaaatttatc cattcggcga cgaagaagaa      60

aaagatgaag gtggtgaaag ctttacatat gaaaaatcag aagttgataa aactgatttg     120

tttaaattca tcgaaggcgg tgaaggtgac gacgtttata aagttgatgg gtcaaaagtt     180

cttcttgacg acgatacaat ttcacgtgtt agcaaaaaac atacagctcg tgatggtgaa     240

tacggtgaat atggggaagc tgttgaagat ggggaaaacg tcattaaaat catccgttca     300

gttcttcaat caggtgcttt accatcagtt ggtgttgatg aacttgacaa aatcgatctt     360

tcatacgaaa caacagaatc aggtgataca gccgtttcag aagattcata cgataaatac     420

gcctcaaata atacaaataa agaaaacatg ccaaatgatc caaatcgtaa tgttgacgaa     480
```

```
aatgccaatg ctaactcagc cgttaaaaac aataacaatg aagaagaaaa aaaagttatt    540

catggttgta atttttcatc taatgtttca tcaaaacata cttttacaga ttcacttgat    600

atttcacttg ttgacgactc agcccacatt tcatgtaatg tccatcttag cgaaccaaaa    660

tacaatcacc ttgttgggct taattgtcca ggtgatatta ttccagactg tttttttcaa    720

gtttaccaac cagaatcaga agaattggaa ccatcaaaca ttgtttatct tgattcacaa    780

atcaatattg gtgatattga atactatgaa gatgccgaag ggatgataa aatcaaactt     840

tttggtatcg tcggttcaat tccaaaaacc acctcattca cctgtatttg taaaaaagac    900

aaaaaatcag cttatatgac agttacaatc gactcagct                            939
```

<210> SEQ ID NO 58
<211> LENGTH: 322
<212> TYPE: PRT
<213> ORGANISM: Artificial sequence
<220> FEATURE:
<223> OTHER INFORMATION: Pro(Cs3)-6C protein sequence

<400> SEQUENCE: 58

```
Glu Tyr Val Asp Glu Lys Glu Arg Gln Gly Glu Ile Tyr Pro Phe Gly
1               5                   10                  15

Asp Glu Glu Glu Lys Asp Glu Gly Gly Glu Ser Phe Thr Tyr Glu Lys
            20                  25                  30

Ser Glu Val Asp Lys Thr Asp Leu Phe Lys Phe Ile Glu Gly Gly Glu
        35                  40                  45

Gly Asp Asp Val Tyr Lys Val Asp Gly Ser Lys Val Leu Leu Asp Asp
    50                  55                  60

Asp Thr Ile Ser Arg Val Ser Lys Lys His Thr Ala Arg Asp Gly Glu
65                  70                  75                  80

Tyr Gly Glu Tyr Gly Glu Ala Val Glu Asp Gly Glu Asn Val Ile Lys
                85                  90                  95

Ile Ile Arg Ser Val Leu Gln Ser Gly Ala Leu Pro Ser Val Gly Val
            100                 105                 110

Asp Glu Leu Asp Lys Ile Asp Leu Ser Tyr Glu Thr Thr Glu Ser Gly
        115                 120                 125

Asp Thr Ala Val Ser Glu Asp Ser Tyr Asp Lys Tyr Ala Ser Asn Asn
    130                 135                 140

Thr Asn Lys Glu Asn Ala Asn Pro Asn Val Asp Pro Asn Ala Asn Pro
145                 150                 155                 160

Asn Val Asp Pro Asn Ala Asn Pro Asn Val Asp Pro Asn Ala Asn Pro
                165                 170                 175

Asn Ala Asn Pro Asn Ala Asn Pro Glu Lys Lys Val Ile His Gly Cys
            180                 185                 190

Asn Phe Ser Ser Asn Val Ser Ser Lys His Thr Phe Thr Asp Ser Leu
        195                 200                 205

Asp Ile Ser Leu Val Asp Asp Ser Ala His Ile Ser Cys Asn Val His
    210                 215                 220

Leu Ser Glu Pro Lys Tyr Asn His Leu Val Gly Leu Asn Cys Pro Gly
225                 230                 235                 240

Asp Ile Ile Pro Asp Cys Phe Phe Gln Val Tyr Gln Pro Glu Ser Glu
                245                 250                 255

Glu Leu Glu Pro Ser Asn Ile Val Tyr Leu Asp Ser Gln Ile Asn Ile
            260                 265                 270

Gly Asp Ile Glu Tyr Tyr Glu Asp Ala Glu Gly Asp Asp Lys Ile Lys
        275                 280                 285
```

Leu Phe Gly Ile Val Gly Ser Ile Pro Lys Thr Thr Ser Phe Thr Cys
290 295 300

Ile Cys Lys Lys Asp Lys Lys Ser Ala Tyr Met Thr Val Thr Ile Asp
305 310 315 320

Ser Ala

<210> SEQ ID NO 59
<211> LENGTH: 966
<212> TYPE: DNA
<213> ORGANISM: Artificial sequence
<220> FEATURE:
<223> OTHER INFORMATION: Pro(Cs3)-6C nucleic acid sequence

<400> SEQUENCE: 59
gaatacgttg atgaaaaaga acgtcaaggt gaaatttatc cattcggcga cgaagaagaa 60
aaagatgaag gtggtgaaag ctttacatat gaaaaatcag aagttgataa aactgatttg 120
tttaaattca tcgaaggcgg tgaaggtgac gacgtttata aagttgatgg gtcaaaagtt 180
cttcttgacg acgatacaat ttcacgtgtt agcaaaaaac atacagctcg tgatggtgaa 240
tacggtgaat atggggaagc tgttgaagat ggggaaaacg tcattaaaat catccgttca 300
gttcttcaat caggtgcttt accatcagtt ggtgttgatg aacttgacaa aatcgatctt 360
tcatacgaaa caacagaatc aggtgataca gccgtttcag aagattcata cgataaatac 420
gcctcaaata atacaaataa agaaaatgct aatccaaatg ttgatccaaa tgcaaatcct 480
aacgtagacc caaacgcaaa ccctaatgtc gatcctaacg ccaatccaaa tgctaaccct 540
aatgctaatc ctgaaaaaaa agtcatccac ggttgtaatt tttcatctaa tgtttcatca 600
aaacatactt ttacagattc acttgatatt tcacttgttg acgactcagc ccacatttca 660
tgtaatgtcc atcttagcga accaaaatac aatcaccttg ttgggcttaa ttgtccaggt 720
gatattattc cagactgttt tttccaagtt tatcaaccag aatcagaaga attggaacca 780
tcaaacattg tttatcttga ttcacaaatc aatattggtg atattgaata ctatgaagat 840
gccgaagggg atgataaaat caaacttttt ggtatcgtcg gttcaattcc aaaaaccacc 900
tcattcacct gtatttgtaa aaaagacaaa aaatcagctt atatgacagt tacaatcgac 960
tcagct 966

<210> SEQ ID NO 60
<211> LENGTH: 304
<212> TYPE: PRT
<213> ORGANISM: Artificial sequence
<220> FEATURE:
<223> OTHER INFORMATION: Pro(Sol)-6C protein sequence

<400> SEQUENCE: 60

Glu Tyr Val Asp Glu Lys Glu Arg Gln Gly Glu Ile Tyr Pro Phe Gly
1 5 10 15

Asp Glu Glu Glu Lys Asp Glu Gly Gly Glu Ser Phe Thr Tyr Glu Lys
20 25 30

Ser Glu Val Asp Lys Thr Asp Leu Phe Lys Phe Ile Glu Gly Gly Glu
35 40 45

Gly Asp Asp Val Tyr Lys Val Asp Gly Ser Lys Val Leu Leu Asp Asp
50 55 60

Asp Thr Ile Ser Arg Val Ser Lys Lys His Thr Ala Arg Asp Gly Glu
65 70 75 80

Tyr Gly Glu Tyr Gly Glu Ala Val Glu Asp Gly Glu Asn Val Ile Lys

```
                85                  90                  95

Ile Ile Arg Ser Val Leu Gln Ser Gly Ala Leu Pro Ser Val Gly Val
            100                 105                 110

Asp Glu Leu Asp Lys Ile Asp Leu Ser Tyr Glu Thr Thr Glu Ser Gly
        115                 120                 125

Asp Thr Ala Val Ser Glu Asp Ser Tyr Asp Lys Tyr Ala Ser Asn Asn
    130                 135                 140

Thr Asn Lys Glu Lys Glu Ser Gly Ser Val Ser Ser Glu Gln Leu Ala
145                 150                 155                 160

Gln Phe Arg Ser Leu Asp Glu Lys Lys Val Ile His Gly Cys Asn Phe
                165                 170                 175

Ser Ser Asn Val Ser Ser Lys His Thr Phe Thr Asp Ser Leu Asp Ile
            180                 185                 190

Ser Leu Val Asp Asp Ser Ala His Ile Ser Cys Asn Val His Leu Ser
        195                 200                 205

Glu Pro Lys Tyr Asn His Leu Val Gly Leu Asn Cys Pro Gly Asp Ile
    210                 215                 220

Ile Pro Asp Cys Phe Phe Gln Val Tyr Gln Pro Glu Ser Glu Glu Leu
225                 230                 235                 240

Glu Pro Ser Asn Ile Val Tyr Leu Asp Ser Gln Ile Asn Ile Gly Asp
                245                 250                 255

Ile Glu Tyr Tyr Glu Asp Ala Glu Gly Asp Asp Lys Ile Lys Leu Phe
            260                 265                 270

Gly Ile Val Gly Ser Ile Pro Lys Thr Thr Ser Phe Thr Cys Ile Cys
        275                 280                 285

Lys Lys Asp Lys Lys Ser Ala Tyr Met Thr Val Thr Ile Asp Ser Ala
    290                 295                 300
```

<210> SEQ ID NO 61
<211> LENGTH: 912
<212> TYPE: DNA
<213> ORGANISM: Artificial sequence
<220> FEATURE:
<223> OTHER INFORMATION: Pro(Sol)-6C nucleic acid sequence

<400> SEQUENCE: 61

```
gaatacgttg atgaaaaaga acgtcaaggt gaaatttatc cattcggcga cgaagaagaa     60

aaagatgaag gtggtgaaag ctttacatat gaaaaatcag aagttgataa aactgatttg    120

tttaaattca tcgaaggcgg tgaaggtgac gacgtttata aagttgatgg gtcaaaagtt    180

cttcttgacg acgatacaat ttcacgtgtt agcaaaaaac atacagctcg tgatggtgaa    240

tacggtgaat atggggaagc tgttgaagat ggggaaaacg tcattaaaat catccgttca    300

gttcttcaat caggtgcttt accatcagtt ggtgttgatg aacttgacaa aatcgatctt    360

tcatacgaaa caacagaatc aggtgataca gccgtttcag aagattcata cgataaatac    420

gcctcaaata atacaaataa agaaaaagaa tcaggttcag tttcatcaga acaacttgcc    480

caatttcgta gcttggacga aaaaaaagtt atccacgggt gtaatttttc atctaatgtt    540

tcttcaaaac atacttttac agattcactt gatatttcac ttgttgacga ctcagcccac    600

atttcatgta atgtccatct tagcgaacca aaatacaatc accttgttgg gcttaattgt    660

ccaggtgata ttattccaga ctgttttttt caagtttacc aaccagaatc agaagaattg    720

gaaccatcaa acattgttta tcttgattca caaatcaata ttggtgatat tgaatactat    780

gaagatgccg aaggggatga taaaatcaaa ctttttggta tcgtcggttc aattccaaaa    840
```

accacctcat tcacctgtat ttgtaaaaaa gacaaaaaat cagcttatat gacagttaca 900
atcgactcag ct 912

<210> SEQ ID NO 62
<211> LENGTH: 284
<212> TYPE: PRT
<213> ORGANISM: Plasmodium falciparum
<220> FEATURE:
<221> NAME/KEY: I-6C protein sequence
<222> LOCATION: (1)..(1)

<400> SEQUENCE: 62

```
Tyr Val Cys Asp Phe Thr Asp Gln Leu Lys Pro Thr Glu Ser Gly Pro
1               5                   10                  15

Lys Val Lys Lys Cys Glu Val Lys Val Asn Glu Pro Leu Ile Lys Val
            20                  25                  30

Lys Ile Ile Cys Pro Leu Lys Gly Ser Val Glu Lys Leu Tyr Asp Asn
        35                  40                  45

Ile Glu Tyr Val Pro Lys Lys Ser Pro Tyr Val Val Leu Thr Lys Glu
    50                  55                  60

Glu Thr Lys Leu Lys Glu Lys Leu Leu Ser Lys Leu Ile Tyr Gly Leu
65                  70                  75                  80

Leu Ile Ser Pro Thr Val Asn Glu Lys Glu Asn Asn Phe Lys Glu Gly
                85                  90                  95

Val Ile Glu Phe Thr Leu Pro Pro Val Val His Lys Ala Thr Val Phe
            100                 105                 110

Tyr Phe Ile Cys Asp Asn Ser Lys Thr Glu Asp Asp Asn Lys Lys Gly
        115                 120                 125

Asn Arg Gly Ile Val Glu Val Tyr Val Glu Pro Tyr Gly Asn Lys Ile
    130                 135                 140

Asn Gly Glu Lys Lys Val Ile His Gly Cys Asn Phe Ser Ser Asn Val
145                 150                 155                 160

Ser Ser Lys His Thr Phe Thr Asp Ser Leu Asp Ile Ser Leu Val Asp
                165                 170                 175

Asp Ser Ala His Ile Ser Cys Asn Val His Leu Ser Glu Pro Lys Tyr
            180                 185                 190

Asn His Leu Val Gly Leu Asn Cys Pro Gly Asp Ile Ile Pro Asp Cys
        195                 200                 205

Phe Phe Gln Val Tyr Gln Pro Glu Ser Glu Glu Leu Glu Pro Ser Asn
    210                 215                 220

Ile Val Tyr Leu Asp Ser Gln Ile Asn Ile Gly Asp Ile Glu Tyr Tyr
225                 230                 235                 240

Glu Asp Ala Glu Gly Asp Asp Lys Ile Lys Leu Phe Gly Ile Val Gly
                245                 250                 255

Ser Ile Pro Lys Thr Thr Ser Phe Thr Cys Ile Cys Lys Lys Asp Lys
            260                 265                 270

Lys Ser Ala Tyr Met Thr Val Thr Ile Asp Ser Ala
        275                 280
```

<210> SEQ ID NO 63
<211> LENGTH: 852
<212> TYPE: DNA
<213> ORGANISM: Plasmodium falciparum
<220> FEATURE:
<221> NAME/KEY: I-6C nucleic acid sequence
<222> LOCATION: (1)..(1)

<400> SEQUENCE: 63

-continued

```
tacgtgtgcg atttcaccga tcagctgaag ccaaccgaga gcggccccaa agtgaagaaa     60

tgcgaagtga aagtgaacga gcccctgatc aaagtcaaga tcatctgccc gctgaagggc    120

agcgtggaaa agctgtacga taacatcgag tacgtgccca agaaaagccc ctacgtggtg    180

ctgaccaaag aggaaacgaa gctgaaagag aagctgctga gcaagctgat ctacggcctg    240

ctgatctccc cgaccgtgaa cgagaaagag aacaacttca aagagggcgt catcgagttc    300

accctgccgc cagtggtgca taaggccacc gtgttctact tcatctgcga taacagcaag    360

accgaggacg acaacaagaa gggcaaccgc ggcatcgtgg aagtgtacgt ggaaccctac    420

ggcaacaaga tcaacggcga gaagaaagtg atccacggct gcaacttcag cagcaacgtg    480

tccagcaagc acaccttcac cgatagcctg gatatcagcc tggtggatga tagcgcccac    540

atctcctgca atgtgcacct gagcgagccc aagtacaatc acctcgtggg actgaactgc    600

ccaggcgata tcatccccga ttgctttttc caagtgtacc agccagagag cgaggaactg    660

gaacccagca acatcgtgta cctggatagc cagatcaaca tcggcgatat cgagtactac    720

gaggatgccg agggcgacga taagatcaag ctgttcggca ttgtgggcag catccccaag    780

accaccagct ttacctgcat ctgcaagaag gacaagaaat ccgcctacat gaccgtgacc    840

atcgatagtg cc                                                        852
```

```
<210> SEQ ID NO 64
<211> LENGTH: 326
<212> TYPE: PRT
<213> ORGANISM: Artificial sequence
<220> FEATURE:
<223> OTHER INFORMATION: I-CSpep-6C protein sequence

<400> SEQUENCE: 64

Tyr Val Cys Asp Phe Thr Asp Gln Leu Lys Pro Thr Glu Ser Gly Pro
1               5                   10                  15

Lys Val Lys Lys Cys Glu Val Lys Val Asn Glu Pro Leu Ile Lys Val
            20                  25                  30

Lys Ile Ile Cys Pro Leu Lys Gly Ser Val Glu Lys Leu Tyr Asp Asn
        35                  40                  45

Ile Glu Tyr Val Pro Lys Lys Ser Pro Tyr Val Val Leu Thr Lys Glu
    50                  55                  60

Glu Thr Lys Leu Lys Glu Lys Leu Leu Ser Lys Leu Ile Tyr Gly Leu
65                  70                  75                  80

Leu Ile Ser Pro Thr Val Asn Glu Lys Glu Asn Asn Phe Lys Glu Gly
                85                  90                  95

Val Ile Glu Phe Thr Leu Pro Pro Val Val His Lys Ala Thr Val Phe
            100                 105                 110

Tyr Phe Ile Cys Asp Asn Ser Lys Thr Glu Asp Asp Asn Lys Lys Gly
        115                 120                 125

Asn Arg Gly Ile Val Glu Val Tyr Val Glu Pro Tyr Gly Asn Lys Ile
    130                 135                 140

Asn Gly Asn Asn Glu Asp Asn Glu Lys Leu Arg Lys Pro Lys His Lys
145                 150                 155                 160

Lys Leu Lys Gln Pro Ala Asp Gly Asn Pro Asp Pro Asn Ala Asn Pro
                165                 170                 175

Asn Val Asp Pro Asn Ala Asn Pro Asn Val Asp Pro Glu Lys Lys Val
            180                 185                 190

Ile His Gly Cys Asn Phe Ser Ser Asn Val Ser Ser Lys His Thr Phe
        195                 200                 205
```

-continued

```
Thr Asp Ser Leu Asp Ile Ser Leu Val Asp Asp Ser Ala His Ile Ser
    210                 215                 220

Cys Asn Val His Leu Ser Glu Pro Lys Tyr Asn His Leu Val Gly Leu
225                 230                 235                 240

Asn Cys Pro Gly Asp Ile Ile Pro Asp Cys Phe Phe Gln Val Tyr Gln
                245                 250                 255

Pro Glu Ser Glu Glu Leu Glu Pro Ser Asn Ile Val Tyr Leu Asp Ser
            260                 265                 270

Gln Ile Asn Ile Gly Asp Ile Glu Tyr Tyr Glu Asp Ala Glu Gly Asp
        275                 280                 285

Asp Lys Ile Lys Leu Phe Gly Ile Val Gly Ser Ile Pro Lys Thr Thr
    290                 295                 300

Ser Phe Thr Cys Ile Cys Lys Lys Asp Lys Lys Ser Ala Tyr Met Thr
305                 310                 315                 320

Val Thr Ile Asp Ser Ala
                325


<210> SEQ ID NO 65
<211> LENGTH: 978
<212> TYPE: DNA
<213> ORGANISM: Artificial sequence
<220> FEATURE:
<223> OTHER INFORMATION: I-CSpep-6C nucleic acid sequence

<400> SEQUENCE: 65

tacgtgtgcg atttcaccga tcagctgaag ccaaccgaga gcggccccaa agtgaagaaa      60

tgcgaagtga aagtgaacga gcccctgatc aaagtcaaga tcatctgccc gctgaagggc     120

agcgtggaaa agctgtacga taacatcgag tacgtgccca agaaaagccc ctacgtggtg     180

ctgaccaaag aggaaacgaa gctgaaagag aagctgctga gcaagctgat ctacggcctg     240

ctgatctccc cgaccgtgaa cgagaaagag aacaacttca aagagggcgt catcgagttc     300

accctgccgc cagtggtgca taaggccacc gtgttctact tcatctgcga taacagcaag     360

accgaggacg acaacaagaa gggcaaccgc ggcatcgtgg aagtgtacgt ggaaccctac     420

ggcaacaaga tcaatggcaa caacgaggac aacgaaaagc tgcgcaagcc caagcacaag     480

aagctgaagc agccagccga tggcaacccc gatccgaacg ccaatccaaa cgtggacccc     540

aatgctaacc ccaatgtgga ccccgagaag aaagtgatcc acggctgcaa cttcagcagc     600

aacgtgtcca gcaagcacac cttcaccgat agcctggata tcagcctggt ggatgatagc     660

gcccacatct cctgcaatgt gcacctgagc gagcccaagt acaatcacct cgtgggactg     720

aactgcccag gcgatatcat ccccgattgc tttttccaag tgtaccagcc agagagcgag     780

gaactggaac ccagcaacat cgtgtacctg gatagccaga tcaacatcgg cgatatcgag     840

tactacgagg atgccgaggg cgacgataag atcaagctgt tcggcattgt gggcagcatc     900

cccaagacca ccagctttac ctgcatctgc aagaaggaca agaaatccgc ctacatgacc     960

gtgaccatcg atagtgcc                                                   978


<210> SEQ ID NO 66
<211> LENGTH: 606
<212> TYPE: PRT
<213> ORGANISM: Artificial sequence
<220> FEATURE:
<223> OTHER INFORMATION: Pro+I-CSpep-10C protein sequence

<400> SEQUENCE: 66
```

-continued

```
Glu Tyr Val Asp Glu Lys Glu Arg Gln Gly Glu Ile Tyr Pro Phe Gly
1               5                   10                  15

Asp Glu Glu Glu Lys Asp Glu Gly Gly Glu Ser Phe Thr Tyr Glu Lys
            20                  25                  30

Ser Glu Val Asp Lys Thr Asp Leu Phe Lys Phe Ile Glu Gly Gly Glu
        35                  40                  45

Gly Asp Asp Val Tyr Lys Val Asp Gly Ser Lys Val Leu Leu Asp Asp
    50                  55                  60

Asp Thr Ile Ser Arg Val Ser Lys Lys His Thr Ala Arg Asp Gly Glu
65                  70                  75                  80

Tyr Gly Glu Tyr Gly Glu Ala Val Glu Asp Gly Glu Asn Val Ile Lys
                85                  90                  95

Ile Ile Arg Ser Val Leu Gln Ser Gly Ala Leu Pro Ser Val Gly Val
            100                 105                 110

Asp Glu Leu Asp Lys Ile Asp Leu Ser Tyr Glu Thr Thr Glu Ser Gly
        115                 120                 125

Asp Thr Ala Val Ser Glu Asp Ser Tyr Asp Lys Tyr Ala Ser Asn Asn
    130                 135                 140

Thr Asn Lys Glu Tyr Val Cys Asp Phe Thr Asp Gln Leu Lys Pro Thr
145                 150                 155                 160

Glu Ser Gly Pro Lys Val Lys Lys Cys Glu Val Lys Val Asn Glu Pro
                165                 170                 175

Leu Ile Lys Val Lys Ile Ile Cys Pro Leu Lys Gly Ser Val Glu Lys
            180                 185                 190

Leu Tyr Asp Asn Ile Glu Tyr Val Pro Lys Lys Ser Pro Tyr Val Val
        195                 200                 205

Leu Thr Lys Glu Glu Thr Lys Leu Lys Glu Lys Leu Leu Ser Lys Leu
    210                 215                 220

Ile Tyr Gly Leu Leu Ile Ser Pro Thr Val Asn Glu Lys Glu Asn Asn
225                 230                 235                 240

Phe Lys Glu Gly Val Ile Glu Phe Thr Leu Pro Pro Val Val His Lys
                245                 250                 255

Ala Thr Val Phe Tyr Phe Ile Cys Asp Asn Ser Lys Thr Glu Asp Asp
            260                 265                 270

Asn Lys Lys Gly Asn Arg Gly Ile Val Glu Val Tyr Val Glu Pro Tyr
        275                 280                 285

Gly Asn Lys Ile Asn Gly Asn Asn Glu Asp Asn Glu Lys Leu Arg Lys
    290                 295                 300

Pro Lys His Lys Lys Leu Lys Gln Pro Ala Asp Gly Asn Pro Asp Pro
305                 310                 315                 320

Asn Ala Asn Pro Asn Val Asp Pro Asn Ala Asn Pro Asn Val Asp Pro
                325                 330                 335

Asp Asn Thr Glu Lys Val Ile Ser Ser Ile Glu Gly Arg Ser Ala Met
            340                 345                 350

Val His Val Arg Val Leu Lys Tyr Pro His Asn Ile Leu Phe Thr Asn
        355                 360                 365

Leu Thr Asn Asp Leu Phe Thr Tyr Leu Pro Lys Thr Tyr Asn Glu Ser
    370                 375                 380

Asn Phe Val Ser Asn Val Leu Glu Val Glu Leu Asn Asp Gly Glu Leu
385                 390                 395                 400

Phe Val Leu Ala Cys Glu Leu Ile Asn Lys Lys Cys Phe Gln Glu Gly
                405                 410                 415

Lys Glu Lys Ala Leu Tyr Lys Ser Asn Lys Ile Ile Tyr His Lys Asn
```

-continued

```
            420                 425                 430

Leu Thr Ile Phe Lys Ala Pro Phe Tyr Val Thr Ser Lys Asp Val Asn
        435                 440                 445

Thr Glu Cys Thr Cys Lys Phe Lys Asn Asn Asn Tyr Lys Ile Val Leu
    450                 455                 460

Lys Pro Lys Tyr Glu Lys Lys Val Ile His Gly Cys Asn Phe Ser Ser
465                 470                 475                 480

Asn Val Ser Ser Lys His Thr Phe Thr Asp Ser Leu Asp Ile Ser Leu
                485                 490                 495

Val Asp Asp Ser Ala His Ile Ser Cys Asn Val His Leu Ser Glu Pro
            500                 505                 510

Lys Tyr Asn His Leu Val Gly Leu Asn Cys Pro Gly Asp Ile Ile Pro
        515                 520                 525

Asp Cys Phe Phe Gln Val Tyr Gln Pro Glu Ser Glu Glu Leu Glu Pro
    530                 535                 540

Ser Asn Ile Val Tyr Leu Asp Ser Gln Ile Asn Ile Gly Asp Ile Glu
545                 550                 555                 560

Tyr Tyr Glu Asp Ala Glu Gly Asp Asp Lys Ile Lys Leu Phe Gly Ile
                565                 570                 575

Val Gly Ser Ile Pro Lys Thr Thr Ser Phe Thr Cys Ile Cys Lys Lys
            580                 585                 590

Asp Lys Lys Ser Ala Tyr Met Thr Val Thr Ile Asp Ser Ala
        595                 600                 605
```

<210> SEQ ID NO 67
<211> LENGTH: 1818
<212> TYPE: DNA
<213> ORGANISM: Artificial sequence
<220> FEATURE:
<223> OTHER INFORMATION: Pro+I-CSpep-10C nucleic acid sequence

<400> SEQUENCE: 67

```
gagtacgtgg acgagaaaga gcgccagggc gagatctacc ccttcggaga tgaggaagaa      60

aaggacgaag gcggcgagag cttcacctac gagaagtccg aagtggataa gaccgacctg     120

ttcaagttca tcgaaggcgg agagggcgac gatgtgtaca aggtggacgg aagcaaggtg     180

ctgctggatg atgataccat cagccgcgtg tccaagaagc acacagctcg cgacggcgag     240

tacggcgaat atggcgaagc tgtggaagat ggcgagaacg tgatcaagat catccgcagc     300

gtgctgcaaa gcggagcctt gccaagtgtg ggagtcgatg agctggacaa gatcgacctg     360

agctacgaga caaccgagag cggagataca gccgtgtccg aggatagcta cgataagtac     420

gccagcaaca acaccaacaa agagtacgtc tgcgatttca ccgatcagct gaagcccacc     480

gagtcgggcc ccaaagtgaa gaaatgcgaa gtgaaagtga acgagcccct gatcaaagtg     540

aaaatcatct gcccgctgaa gggcagcgtg gaaaagctgt acgataacat tgagtacgtg     600

cccaagaaaa gcccctacgt ggtgctgacc aaagaggaaa cgaagctgaa agagaagctg     660

ctgagcaagc tgatctacgg cctgctgatc tccccgaccg tgaatgagaa agagaacaac     720

ttcaaagagg gcgtcatcga gttcaccctg ccgccagtgg tgcataaggc caccgtgttc     780

tacttcatct gcgataacag caagaccgag gacgacaaca agaagggcaa ccgcggcatc     840

gtggaagtgt acgtggaacc ctacggcaac aagatcaatg gcaacaacga ggacaacgaa     900

aagctgcgca agcccaagca caagaagctg aagcagccag ccgatggcaa ccccgatccg     960

aacgccaatc caaacgtgga ccccaatgct aaccccaatg tggaccccga taacaccgag    1020
```

aaagtgatct ccagcattga gggccgcagt gccatggtgc atgtgcgcgt gctgaagtac 1080
ccgcacaaca tcctgttcac caacctgacc aacgatctgt tcacctatct gcccaagacc 1140
tacaacgaga gcaacttcgt gtccaacgtg ctggaagtgg aactgaacga tggcgagctg 1200
tttgtgctgg cctgcgagct gattaacaag aagtgcttcc aagagggcaa agagaaggcc 1260
ctgtacaagt ccaacaagat tatctaccac aagaacctga cgatcttcaa ggccccgttc 1320
tacgtgacca gcaaggatgt gaataccgag tgcacatgca agttcaagaa caacaactac 1380
aagatcgtgc tcaagccgaa gtacgagaag aaagtcatcc acggctgcaa cttcagcagc 1440
aacgtgtcct ccaagcacac cttcaccgat agcctggata tcagcctggt ggatgatagc 1500
gcccacatct cctgcaatgt gcacctgagc gagcccaagt acaatcacct cgtgggactg 1560
aactgcccag gcgatatcat ccccgattgc tttttccaag tgtaccagcc agagagcgag 1620
gaactggaac ccagcaacat cgtgtacctg gatagccaga tcaacatcgg cgatatcgag 1680
tactacgagg atgccgaagg cgacgataag atcaagctgt tcggcattgt gggcagcatc 1740
cccaagacca ccagctttac ctgcatctgc aagaaggaca agaaatccgc ctacatgacc 1800
gtgaccatcg atagtgcc 1818

<210> SEQ ID NO 68
<211> LENGTH: 474
<212> TYPE: PRT
<213> ORGANISM: Artificial sequence
<220> FEATURE:
<223> OTHER INFORMATION: Pro+I-CSpep-6C protein sequence

<400> SEQUENCE: 68

Glu Tyr Val Asp Glu Lys Glu Arg Gln Gly Glu Ile Tyr Pro Phe Gly
1 5 10 15

Asp Glu Glu Glu Lys Asp Glu Gly Gly Glu Ser Phe Thr Tyr Glu Lys
20 25 30

Ser Glu Val Asp Lys Thr Asp Leu Phe Lys Phe Ile Glu Gly Gly Glu
35 40 45

Gly Asp Asp Val Tyr Lys Val Asp Gly Ser Lys Val Leu Leu Asp Asp
50 55 60

Asp Thr Ile Ser Arg Val Ser Lys Lys His Thr Ala Arg Asp Gly Glu
65 70 75 80

Tyr Gly Glu Tyr Gly Glu Ala Val Glu Asp Gly Glu Asn Val Ile Lys
85 90 95

Ile Ile Arg Ser Val Leu Gln Ser Gly Ala Leu Pro Ser Val Gly Val
100 105 110

Asp Glu Leu Asp Lys Ile Asp Leu Ser Tyr Glu Thr Thr Glu Ser Gly
115 120 125

Asp Thr Ala Val Ser Glu Asp Ser Tyr Asp Lys Tyr Ala Ser Asn Asn
130 135 140

Thr Asn Lys Glu Tyr Val Cys Asp Phe Thr Asp Gln Leu Lys Pro Thr
145 150 155 160

Glu Ser Gly Pro Lys Val Lys Lys Cys Glu Val Lys Val Asn Glu Pro
165 170 175

Leu Ile Lys Val Lys Ile Ile Cys Pro Leu Lys Gly Ser Val Glu Lys
180 185 190

Leu Tyr Asp Asn Ile Glu Tyr Val Pro Lys Lys Ser Pro Tyr Val Val
195 200 205

Leu Thr Lys Glu Glu Thr Lys Leu Lys Glu Lys Leu Leu Ser Lys Leu
210 215 220

```
Ile Tyr Gly Leu Leu Ile Ser Pro Thr Val Asn Glu Lys Glu Asn Asn
225                 230                 235                 240

Phe Lys Glu Gly Val Ile Glu Phe Thr Leu Pro Pro Val Val His Lys
                245                 250                 255

Ala Thr Val Phe Tyr Phe Ile Cys Asp Asn Ser Lys Thr Glu Asp Asp
            260                 265                 270

Asn Lys Lys Gly Asn Arg Gly Ile Val Glu Val Tyr Val Glu Pro Tyr
        275                 280                 285

Gly Asn Lys Ile Asn Gly Asn Asn Glu Asp Asn Glu Lys Leu Arg Lys
    290                 295                 300

Pro Lys His Lys Lys Leu Lys Gln Pro Ala Asp Gly Asn Pro Asp Pro
305                 310                 315                 320

Asn Ala Asn Pro Asn Val Asp Pro Asn Ala Asn Pro Asn Val Asp Pro
                325                 330                 335

Glu Lys Lys Val Ile His Gly Cys Asn Phe Ser Ser Asn Val Ser Ser
            340                 345                 350

Lys His Thr Phe Thr Asp Ser Leu Asp Ile Ser Leu Val Asp Asp Ser
        355                 360                 365

Ala His Ile Ser Cys Asn Val His Leu Ser Glu Pro Lys Tyr Asn His
    370                 375                 380

Leu Val Gly Leu Asn Cys Pro Gly Asp Ile Ile Pro Asp Cys Phe Phe
385                 390                 395                 400

Gln Val Tyr Gln Pro Glu Ser Glu Glu Leu Glu Pro Ser Asn Ile Val
                405                 410                 415

Tyr Leu Asp Ser Gln Ile Asn Ile Gly Asp Ile Glu Tyr Tyr Glu Asp
            420                 425                 430

Ala Glu Gly Asp Asp Lys Ile Lys Leu Phe Gly Ile Val Gly Ser Ile
        435                 440                 445

Pro Lys Thr Thr Ser Phe Thr Cys Ile Cys Lys Lys Asp Lys Lys Ser
    450                 455                 460

Ala Tyr Met Thr Val Thr Ile Asp Ser Ala
465                 470
```

<210> SEQ ID NO 69
<211> LENGTH: 1488
<212> TYPE: DNA
<213> ORGANISM: Artificial sequence
<220> FEATURE:
<223> OTHER INFORMATION: Pro+I-CSpep-6C nucleic acid sequence

<400> SEQUENCE: 69

```
gaattcgcca ccatgaagct gtgcatcctg ctggccgtgg tggcctttgt tggactgagt     60

ttgggagagt acgtggacga gaaagagcgc cagggcgaga tctacccctt cggagatgag    120

gaagaaaagg acgaaggcgg cgagagcttc acctacgaga agtccgaagt ggataagacc    180

gacctgttca agttcatcga aggcggagag ggcgacgatg tgtacaaggt ggacggaagc    240

aaggtgctgc tggatgatga taccatcagc cgcgtgtcca agaagcacac agctcgcgac    300

ggcgagtacg gcgaatatgg cgaagctgtg gaagatggcg agaacgtgat caagatcatc    360

cgcagcgtgc tgcaaagcgg agccttgcca agtgtgggag tcgatgagct ggacaagatc    420

gacctgagct acgagacaac cgagagcgga gatacagccg tgtccgagga tagctacgat    480

aagtacgcca gcaacaacac caacaaagag tacgtctgcg atttcaccga tcagctgaag    540

cccaccgagt cgggccccaa agtgaagaaa tgcgaagtga aagtgaacga gcccctgatc    600
```

```
aaagtgaaaa tcatctgccc gctgaagggc agcgtggaaa agctgtacga taacattgag    660

tacgtgccca agaaaagccc ctacgtggtg ctgaccaaag aggaaacgaa gctgaaagag    720

aagctgctga gcaagctgat ctacggcctg ctgatctccc cgaccgtgaa tgagaaagag    780

aacaacttca aagagggcgt catcgagttc accctgccgc cagtggtgca taaggccacc    840

gtgttctact tcatctgcga taacagcaag accgaggacg acaacaagaa gggcaaccgc    900

ggcatcgtgg aagtgtacgt ggaaccctac ggcaacaaga tcaatggcaa caacgaggac    960

aacgaaaagc tgcgcaagcc caagcacaag aagctgaagc agccagccga tggcaacccc   1020

gatccgaacg ccaatccaaa cgtggacccc aatgctaacc ccaatgtgga ccccgagaag   1080

aaagtgatcc acggctgcaa cttcagcagc aacgtgtcct ccaagcacac cttcaccgat   1140

agcctggata tcagcctggt ggatgatagc gcccacatct cctgcaatgt gcacctgagc   1200

gagcccaagt acaatcacct cgtgggactg aactgcccag gcgatatcat ccccgattgc   1260

tttttccaag tgtaccagcc agagagcgag gaactggaac ccagcaacat cgtgtacctg   1320

gatagccaga tcaacatcgg cgatatcgag tactacgagg atgccgaagg cgacgataag   1380

atcaagctgt tcggcattgt gggcagcatc cccaagacca ccagctttac ctgcatctgc   1440

aagaaggaca agaaatccgc ctacatgacc gtgaccatcg atagtgcc                1488
```

<210> SEQ ID NO 70
<211> LENGTH: 474
<212> TYPE: PRT
<213> ORGANISM: Artificial sequence
<220> FEATURE:
<223> OTHER INFORMATION: Pro+I-CSpep-6C G397L protein sequence

<400> SEQUENCE: 70

```
Glu Tyr Val Asp Glu Lys Glu Arg Gln Gly Glu Ile Tyr Pro Phe Gly
1               5                   10                  15

Asp Glu Glu Glu Lys Asp Glu Gly Gly Glu Ser Phe Thr Tyr Glu Lys
            20                  25                  30

Ser Glu Val Asp Lys Thr Asp Leu Phe Lys Phe Ile Glu Gly Gly Glu
        35                  40                  45

Gly Asp Asp Val Tyr Lys Val Asp Gly Ser Lys Val Leu Leu Asp Asp
    50                  55                  60

Asp Thr Ile Ser Arg Val Ser Lys Lys His Thr Ala Arg Asp Gly Glu
65                  70                  75                  80

Tyr Gly Glu Tyr Gly Glu Ala Val Glu Asp Gly Glu Asn Val Ile Lys
                85                  90                  95

Ile Ile Arg Ser Val Leu Gln Ser Gly Ala Leu Pro Ser Val Gly Val
            100                 105                 110

Asp Glu Leu Asp Lys Ile Asp Leu Ser Tyr Glu Thr Thr Glu Ser Gly
        115                 120                 125

Asp Thr Ala Val Ser Glu Asp Ser Tyr Asp Lys Tyr Ala Ser Asn Asn
    130                 135                 140

Thr Asn Lys Glu Tyr Val Cys Asp Phe Thr Asp Gln Leu Lys Pro Thr
145                 150                 155                 160

Glu Ser Gly Pro Lys Val Lys Lys Cys Glu Val Lys Val Asn Glu Pro
                165                 170                 175

Leu Ile Lys Val Lys Ile Ile Cys Pro Leu Lys Gly Ser Val Glu Lys
            180                 185                 190

Leu Tyr Asp Asn Ile Glu Tyr Val Pro Lys Lys Ser Pro Tyr Val Val
        195                 200                 205
```

-continued

```
Leu Thr Lys Glu Glu Thr Lys Leu Lys Glu Lys Leu Leu Ser Lys Leu
    210                 215                 220

Ile Tyr Gly Leu Leu Ile Ser Pro Thr Val Asn Glu Lys Glu Asn Asn
225                 230                 235                 240

Phe Lys Glu Gly Val Ile Glu Phe Thr Leu Pro Pro Val Val His Lys
                245                 250                 255

Ala Thr Val Phe Tyr Phe Ile Cys Asp Asn Ser Lys Thr Glu Asp Asp
            260                 265                 270

Asn Lys Lys Gly Asn Arg Gly Ile Val Glu Val Tyr Val Glu Pro Tyr
        275                 280                 285

Gly Asn Lys Ile Asn Gly Asn Asn Glu Asp Asn Glu Lys Leu Arg Lys
    290                 295                 300

Pro Lys His Lys Lys Leu Lys Gln Pro Ala Asp Gly Asn Pro Asp Pro
305                 310                 315                 320

Asn Ala Asn Pro Asn Val Asp Pro Asn Ala Asn Pro Asn Val Asp Pro
                325                 330                 335

Glu Lys Lys Val Ile His Gly Cys Asn Phe Ser Ser Asn Val Ser Ser
            340                 345                 350

Lys His Thr Phe Thr Asp Ser Leu Asp Ile Ser Leu Val Asp Asp Ser
        355                 360                 365

Ala His Ile Ser Cys Asn Val His Leu Ser Glu Pro Lys Tyr Asn His
    370                 375                 380

Leu Val Gly Leu Asn Cys Pro Gly Asp Ile Ile Pro Asp Cys Phe Phe
385                 390                 395                 400

Gln Val Tyr Gln Pro Glu Ser Glu Glu Leu Glu Pro Ser Asn Ile Val
                405                 410                 415

Tyr Leu Asp Ser Gln Ile Asn Ile Gly Asp Ile Glu Tyr Tyr Glu Asp
            420                 425                 430

Ala Glu Gly Asp Asp Lys Ile Lys Leu Phe Leu Ile Val Gly Ser Ile
        435                 440                 445

Pro Lys Thr Thr Ser Phe Thr Cys Ile Cys Lys Lys Asp Lys Lys Ser
    450                 455                 460

Ala Tyr Met Thr Val Thr Ile Asp Ser Ala
465                 470


<210> SEQ ID NO 71
<211> LENGTH: 1422
<212> TYPE: DNA
<213> ORGANISM: Artificial sequence
<220> FEATURE:
<223> OTHER INFORMATION: Pro+I-CSpep-6C G397L nucleic acid sequence

<400> SEQUENCE: 71

gagtacgtgg acgagaaaga gcgccagggc gagatctacc ccttcggaga tgaggaagaa      60

aaggacgaag gcggcgagag cttcacctac gagaagtccg aagtggataa gaccgacctg     120

ttcaagttca tcgaaggcgg agagggcgac gatgtgtaca aggtggacgg aagcaaggtg     180

ctgctggatg atgataccat cagccgcgtg tccaagaagc acacagctcg cgacggcgag     240

tacggcgaat atggcgaagc tgtggaagat ggcgagaacg tgatcaagat catccgcagc     300

gtgctgcaaa gcggagcctt gccaagtgtg ggagtcgatg agctggacaa gatcgacctg     360

agctacgaga caaccgagag cggagataca gccgtgtccg aggatagcta cgataagtac     420

gccagcaaca acaccaacaa agagtacgtc tgcgatttca ccgatcagct gaagcccacc     480

gagtcgggcc ccaaagtgaa gaaatgcgaa gtgaaagtga acgagcccct gatcaaagtg     540
```

-continued

```
aaaatcatct gcccgctgaa gggcagcgtg gaaaagctgt acgataacat tgagtacgtg    600
cccaagaaaa gcccctacgt ggtgctgacc aaagaggaaa cgaagctgaa agagaagctg    660
ctgagcaagc tgatctacgg cctgctgatc tccccgaccg tgaatgagaa agagaacaac    720
ttcaaagagg gcgtcatcga gttcaccctg ccgccagtgg tgcataaggc caccgtgttc    780
tacttcatct gcgataacag caagaccgag gacgacaaca agaagggcaa ccgcggcatc    840
gtggaagtgt acgtggaacc ctacggcaac aagatcaatg gcaacaacga ggacaacgaa    900
aagctgcgca agcccaagca caagaagctg aagcagccag ccgatggcaa ccccgatccg    960
aacgccaatc caaacgtgga ccccaatgct aaccccaatg tggaccccga gaagaaagtg   1020
atccacggct gcaacttcag cagcaacgtg tcctccaagc acaccttcac cgatagcctg   1080
gatatcagcc tggtggatga tagcgcccac atctcctgca atgtgcacct gagcgagccc   1140
aagtacaatc acctcgtggg actgaactgc ccaggcgata tcatccccga ttgctttttc   1200
caagtgtacc agccagagag cgaggaactg gaacccagca acatcgtgta cctggatagc   1260
cagatcaaca tcggcgatat cgagtactac gaggatgccg aaggcgacga taagatcaag   1320
ctgttcctga tcgtgggcag catccccaag accaccagct ttacctgcat ctgcaagaag   1380
gacaagaaat ccgcctacat gaccgtgacc atcgatagtg cc                      1422
```

MULTIVALENT MALARIA TRANSMISSION-BLOCKING VACCINES

TECHNICAL FIELD OF THE INVENTION

The present invention relates to a method for recombinant production of a fusion protein comprising multiple malaria antigens for inducing immune responses comprising a combination of antibodies. In particular, the fusion proteins of the present invention comprise fragments of both Pfs230 and Pfs48/45 to lower the required threshold of functional antibodies and to reduce the risk of escape mutations. Thus, the fusion proteins of the present invention are suitable for use in a multivalent malaria vaccine.

BACKGROUND OF THE INVENTION

The transmission of *Plasmodium falciparum* from one person to another relies on the generation of male and female gametocytes in the human host that can be picked up and spread by a mosquito. The aim of a malaria transmission blocking vaccine (MTBV) is to effectively block malaria transmission at the population level thereby contributing to malaria elimination, i.e. by preventing an individual from becoming infected with *Plasmodium* parasites by mosquito bites of mosquitoes belonging to the *Anopheles* genus.

Several MTBV candidates have been identified by screening monoclonal antibodies generated against *P. falciparum* mosquito stages for transmission blocking activity. Three proteins, Pfs48/45, Pfs230, and Pfs25 are currently targeted as lead candidates for an MTBV. Of these, Pfs48/45 and Pfs230 are expressed in the gametocyte as it develops from stage III through V inside red blood cells (RBCs) in the human host. Shortly, after being taken up by a blood-feeding mosquito, the parasite emerges from the RBC as a gamete and after a few rounds of replication motile males fertilize female gametes to form zygotes. Pfs48/45 is expressed on the surface of both male and female gametes where it is bound to the plasma membrane through a GPI-anchor and forms a stable complex with Pfs230. Both Pfs48/45 and Pfs230 are important for male fertility.

Humans develop naturally acquired immunity against *P. falciparum* gametocytes and antibodies against Pfs230 and Pfs48/45 have been associated with transmission blocking activity in some but not all immune epidemiological studies. Pfs48/45- and Pfs230-specific antibodies has previously been shown to exhibit strong transmission blocking activity in the standard membrane feeding assay (SMFA), the gold standard for assessing transmission blockade ex vivo. Whether such antibodies act synergistically is not yet known.

Pfs48/45 and Pfs230 are members of the six-cysteine (6-Cys) s48/45 protein family and contain three and fourteen 6-Cys domains, respectively. Each 6-Cys domain contains up to six cysteine residues that are involved in intra-domain disulfide bond formation which results in conformational antibody epitopes. The C-terminal 6-Cys domain of Pfs48/45 contains the conformational epitope I, which is targeted by the most potent transmission blocking monoclonal antibody described to date, mAb45.1.

Pfs48/45 has been produced in recombinant form in different expression systems. However, the major challenges with recombinant Pfs48/45 are that it is very difficult to produce correctly folded protein. Proper folding of many cysteine rich proteins, including Pfs48/45, depends on correct formation of disulphide bridges. Thus, expression of recombinant Pfs48/45 fragments in *Lactococcus lactis* in absence of a fusion partner has previously been shown to be difficult (Theisen et. al., 2014).

Singh et al. (2017) later showed that a *Lactococcus lactis* expression system can be utilized for the production of the C-terminal 6-Cys domain of Pfs48/45 (6C) as a fusion protein (R0.6C) with the N-terminal GLURP-R0 region. The resulting fusion protein can be produced in high yields of properly folded monomeric protein which elicit high levels of transmission blocking antibodies in small rodents.

In the case of Pfs230, the C fragment spanning the N-terminal pro-domain and first three 6-Cys domains has been shown to elicit the most potent transmission blocking antibodies. MacDonald et al. (2016) produced in Pichia pastoris a construct termed "Pfs230D1" corresponding to amino acid residues 444 to 736. The protein was correctly folded and elicited transmission blocking antibodies in rodents. While clinical trials with Pfs230D1 are ongoing (ClinicalTrials.gov Identifier: NCT02334462) and R0.6C is in early clinical development phase, an effective malaria transmission blocking vaccine is still not available on the market.

A disadvantage of these vaccine candidates is that they are liable to escape mutants as they promote only an immune response to a single antigenic target. Thus, host immune responses may fail due to mutations in genotype and phenotype of the target. This will ultimately compromise overall vaccine efficacy as exemplified with the RTS,S malaria vaccine produced by GSK. To this end, it could be beneficial to target multiple antigens simultaneously to mitigate the obstacle with escape mutants and help reduce the spread of potential escape mutants in the population.

WO2013/050034 A1 describes the production of a cysteine rich fusion protein comprising proteins derived from *Plasmodium falciparum*. The fusion protein comprised a glutamate rich protein to enhance correct folding of the fusion protein. While GLURP does promote correct folding of the fusion protein, it does not contribute to the induction of a transmission blocking immune response. However, a fusion protein comprising fragments of Pfs48/45 and Pfs230 has not previously been produced in high yield without the use of a "helper protein", such as GLURP.

Hence, a simplified method for providing in high yield a fusion protein capable of eliciting an improved immune response would be advantageous, and in particular, the provision of a fusion protein to include in an enhanced multivalent malaria transmission blocking vaccine (MTBV) would be advantageous.

SUMMARY OF THE INVENTION

Thus, an object of the present invention relates to a method for recombinant production of potent Pfs48/45- and Pfs230-based immunogens.

Another object of the present invention is to provide a simplified method for producing in high yields fusion proteins based on fragments of Pfs48/45 and Pfs230.

In particular, it is an object of the present invention to utilize the produced fusion proteins in an improved multivalent malaria vaccine to solve the above mentioned problems of the prior art of susceptibility to escape mutant and insufficient immune response.

Thus, one aspect of the present invention relates to a method for recombinant production of a fusion protein comprising a fragment of Pfs230 and a fragment of Pfs48/45, wherein the fusion protein is produced in a recombinant expression system, optionally in the presence of one or more redox coupling agents.

Another aspect of the present invention relates to a fusion protein obtainable by the method according to the present invention.

Yet another aspect of the present invention is to provide a fusion protein comprising:

i) a fragment of Pfs230 comprising the antigenic domain Pro or an amino acid sequence having at least 90% sequence identity to Pro, and ii) a fragment of Pfs48/45 comprising one of the antigenic domains 6C and 10C, or an amino acid sequence having at least 90% sequence identity to 6C or 10C.

Still another aspect of the present invention is to provide a multivalent vaccine or immunogenic composition comprising the fusion protein according to the present invention.

An even further aspect of the present invention relates to a fusion protein according to the present invention or a vaccine or immunogenic composition according to the present invention for use as a medicament.

Another aspect of the present invention relates to a fusion protein according to the present invention or a vaccine or immunogenic composition according to the present invention for use in the prevention, amelioration or treatment of malaria.

Yet another aspect of the present invention is to provide a nucleic acid encoding the fusion protein according to the present invention.

An additional aspect of the present invention is to provide a vector comprising the nucleic acid according to the present invention.

A further aspect of the present invention relates to use of a nucleic acid according to the present invention or a vector according to the present invention for preparation of a vaccine or immunogenic composition.

BRIEF DESCRIPTION OF THE FIGURES

(FIG. 1A) Schematic representation of Pfs230 constructs and Pfs230-Pfs48/45 fusion proteins. Each construct contain the SpyCatcher sequence at the N-terminus and a His-tag at the C-terminus. (FIG. 1B) Coomassie blue stained 4-12.5% polyacrylamide gel of conventionally purified Pfs230 constructs and immune-purified Pro-6C fusion protein. Protein was loaded in each lane with (+) or without (−) DTT (10 mM). The sizes (kDa) of the molecular mass markers are indicated. (FIG. 1C) Sandwich ELISA of purified Pro-6C fusion protein. The antigens were captured with mAb45.1 and detected with anti-His-HRP. Immune purified R0.6C were used as a reference. X-axis is shown on a logarithmic scale. (FIG. 1D) Agarose gel of the Pfs48/45-6C amplicon.

(FIG. 1**D) Functional activity of serial dilutions of pooled sera in the SMFA. Transmission reducing activity (TRA) is the reduction of oocyst numbers compared to a pre-immune serum control. Data points are best estimates of two independent experiments and error bars represent 95% confidence intervals.

(FIG. 3A) Schematic representation of the Pro+I-6C fusion protein. This protein contains the SpyCatcher sequence at the N-terminus and a His-tag at the C-terminus. (FIG. 3B) Sandwich ELISA of purified fusion proteins. Immune purified R0.6C was used as a reference. Size exclusion chromatography analysis of (FIG. 3C) Pro-6C and (FIG. 3D) Pro+I-6C. SE-HPLC was performed under native conditions in a phosphate buffer of pH 7.2 to determine the amount of monomer in the sample. The sizes (kDa) of the molecular mass markers are indicated.

(FIG. 4A) Reduced and non-reduced SDS-PAGE gel and western blot. The gels (left, 4A) are stained with coomassie blue, while the western blots (right, 4A) are developed with mAb45.1 as primary antibody. The following was loaded corresponding to the numbers; Lane 1: AP205 (VLP); lane 2: Pro-6C; lane 3: Pro-6C-VLP; lane 4: Pro+I-6C; Lane 5: Pro+I-6C-VLP. (FIG. 4B) Sandwich ELISA, using mAb 45.1 as the solid phase capture antibody. (FIG. 4C) Transmission electron microscopy images (negative stain) of the VLP-based vaccines after assembly. Both Pro-6C-VLPs and Pro+I-6C-VLPs appear non-aggregated, uniformly dispersed and have an estimated size of 30 nm. Scale bar 100 nm. (FIG. 4D) Dynamic light scattering (DLS) profile of the vaccine components Pro-6C (10.5 nm, polydispersity (PD) 10.7%), Pro+I-6C (10.8 nm, PD 20.7%), VLP (25.6 nm, PD 16.8%) and the purified vaccine products; Pro-6C-VLP (71.8 nm, PD 11.5%) and Pro+I-6C-VLP (73.7 nm, PD 15.8%).

(FIG. 5**D) Functional activities of serial diluted sera were assessed in the SMFA. Transmission reducing activity (TRA) is the reduction of oocyst load compared to a pre-immune serum control. Data points are best estimates of two independent experiments and error bars represent 95% confidence intervals. Note that 1/81 and 1/247 samples were tested in SMFA only once and therefore no confidence intervals are given.

(FIG. 6A) Panel of fusion protein constructs comprising Pfs230-Pro and Pfs48/45-6C connected by five different linker sequences denoted Flex2 (SEQ ID NO:42), CsTSR (SEQ ID NO:44), CsLNK (SEQ ID NO:46), Cs3 (SEQ ID NO:48) and Sol (SEQ ID NO:50), respectively. SDS-Page gels (FIG. 6B) and western blots (FIG. 6C) of secreted recombinant fusion protein constructs (1) Pro-6C, (2) Pro (Flex2)-6C, (3) Pro(CsTSR)-6C, (4) Pro(CsLNK)-6C, (5) Pro(Cs3)-6C, and (6) Pro(Sol)-6C. The SDS-PAGE gels are stained with Coomassie blue, while the western blots are developed with mAb45.1 as primary antibody.

6C, Pro(CsLNK)-6C, Pro(Cs3)-6C, Pro(Sol)-6C, or R0.6C were tested for antibody reactivity on ELISA plates coated with (FIG. 7A) Pfs48/45-6C or (FIG. 7B) Pfs230 Pro. Antibody titers are expressed as EC50 values. Horizontal lines represent median values. (FIG. 7C) Functional activity of pooled serum at 1/9 dilution was assessed in the SMFA as quantified by transmission reducing activity (TRA).

(FIG. 8A) Culture supernatant fusion proteins were separated on a 4-12% polyacrylamide gel with (+) and without (−) a reducing agent and stained with coomassie blue. Lane 1, BSA (0.5 and 1 ug); Lane 2, I-6C; Lane 3, Pro+I-6C; Lane 4, I-CSpep-6C; Lane 5, Pro+I-CSpep-6C; Lane 6, Pro+I-CSpep-10C. Fusion protein was loaded in each lane with (+) or without (−) DTT (10 mM). The sizes (kDa) of the molecular mass markers are indicated. (FIG. 8B) Analysis of ion-exchanged purified protein by SDS-PAGE. Coomassie blue-stained 4-12.5% polyacrylamide gel; 1. I-6C-Ctag, 2. I-CSpep-6C-Ctag, 3. Pro+I-6C-Ctag, 4. Pro+I-CSpep-6C-Ctag, 5. Pro+I-CSpep-10C-Ctag. Moreover is shown an immune blot analysis of the gel of (B) using mAb45.1 (FIG. 8C) and mAb15C5 (anti-domain I) (FIG. 8D) antibodies.

(FIG. 9A) Culture supernatant fusion proteins were separated on a 4-12% polyacrylamide gel with (+) and without (−) a reducing agent and stained with coomassie blue. Lane 1, Pro+I-CSpep-6C wildtype; Lane 2, Pro+I-CSpep-6C mutant (single amino acid mutation was in the 6C sequence by replacing G397L). A Dot blot analysis for purified proteins shown in the panel (9A) with a serial dilution using mAb45.1 (FIG. 9B) and mAb15C5 (FIG. 9C) antibodies.

Figure 1A:
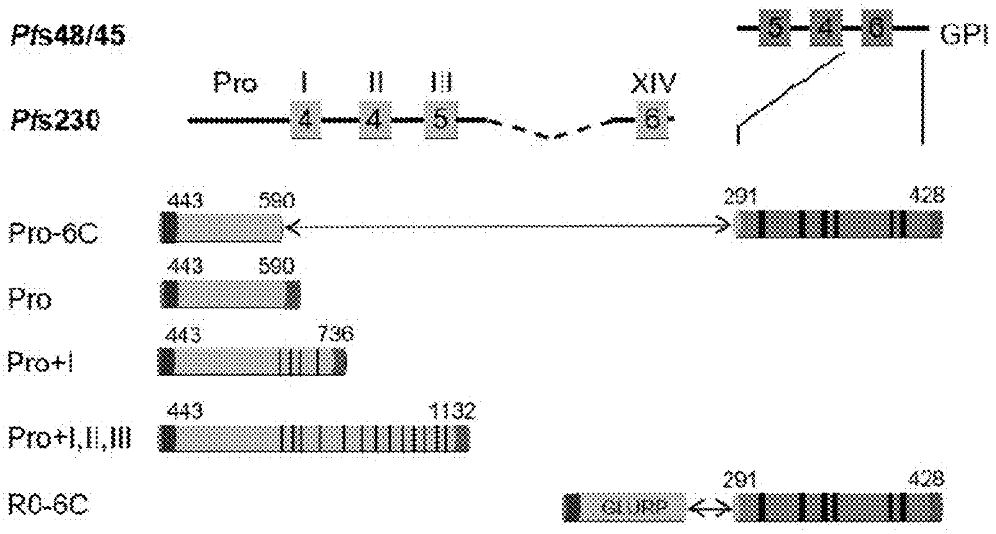
FIGS. 1A-1D shows production of recombinant Pfs230 and Pfs48/45.

The present invention will now be described in more detail in the following.

DETAILED DESCRIPTION OF THE INVENTION

Definitions

Prior to discussing the present invention in further details, the following terms and conventions will first be defined:

Fusion Protein

In the present context, the term "fusion protein" refers to a recombinant fusion protein encoded by a nucleotide sequence, which is obtained by genetically joining nucleotide sequences derived from different regions of one gene and/or by joining nucleotide sequences derived from two or more separate genes.

In the present context, these nucleotide sequences are derived from Pfs230 and Pfs48/45 of *P. falciparum*. As these nucleotide sequence may comprise only parts of Pfs230 and Pfs48/45, the resulting amino acid (polypeptide) sequences are also referred to as fragments of Pfs230 and Pfs48/45. Preferably, the fragments of Pfs230 and Pfs48/45 comprise exclusively sequences capable of inducing a desired immune response, such sequences are also identified herein as antigenic domains.

The fusion proteins may comprise further functional components enabling e.g. purification and/or coupling to additional entities. Examples of functional components include, but are not limited to, purification tags, linker sections, imaging tags and coupling moieties. Thus, fusion proteins may comprise His-tags, C-tags, and SpyCatcher sequences.

Antigenic Domain

In the present context, the term "antigenic domain" refers a polypeptide region of the fusion protein, which is capable of inducing a desired immune response, e.g. suitable for use in a malaria transmission blocking vaccine (MTBV).

Pfs230

In the present context, the term "Pfs230" refers to the protein Pfs230 expressed during the *P. falciparum* transmission stage in humans. Pfs230 comprises several antigenic domains, including, but not limited to, Pro, domain I, domain II, and domain III. Thus, a fragment of Pfs230 may comprise one or more of these antigenic domains.

The above-mentioned antigenic domains of Pfs230 can be represented by the following amino acid and nucleic acid sequences:

- Pro has the amino acid sequence represented by SEQ ID NO:1 and is encoded by the nucleic acid sequence represented by SEQ ID NO:2
- Doman I has the amino acid sequence represented by SEQ ID NO:3 and is encoded by the nucleic acid sequence represented by SEQ ID NO:4
- Domain II has the amino acid sequence represented by SEQ ID NO:5 and is encoded by the nucleic acid sequence represented by SEQ ID NO:6
- Domain III has the amino acid sequence represented by SEQ ID NO:7 and is encoded by the nucleic acid sequence represented by SEQ ID NO:8

Moreover, the combination of antigenic domains Pro and domain I (Pro+I) has the amino acid sequence represented by SEQ ID NO:9 and is encoded by the nucleic acid sequence represented by SEQ ID NO:10.

Amino acid sequences that comprises at least 90% sequence identity to SEQ ID NO:1, SEQ ID NO:3, SEQ ID NO: 5, SEQ ID NO:7, or SEQ ID NO:9, such as at least 95% sequence identity, such as at least 96% sequence identity, such as at least 97% sequence identity, such as at least 98% sequence identity, or such as at least 99% sequence identity, are also considered antigenic domains of Pfs230. These antigenic domains when referred to herein are immunogenic and induces an immune response of at least same magnitude and quality as any one of the antigenic domains with which it shares sequence similarity, i.e. SEQ ID NO:1, SEQ ID NO:3, SEQ ID NO: 5, SEQ ID NO:7, or SEQ ID NO:9.

Pfs48/45

In the present context, the term "Pfs48/45" refers to the protein Pfs48/45 expressed during the *P. falciparum* transmission stage in humans. Pfs48/45 comprises several antigenic domains, including, but not limited to, 6C and the larger domain 10C which comprises 6C. Thus, a fragment of Pfs230 may comprise either 6C or 10C.

The above-mentioned antigenic domains of Pfs48/45 can be represented by the following amino acid and nucleic acid sequences:

- 6C has the amino acid sequence represented by SEQ ID NO:11 and is encoded by the nucleic acid sequence represented by SEQ ID NO:12
- 10C has the amino acid sequence represented by SEQ ID NO:13 and is encoded by the nucleic acid sequence represented by SEQ ID NO:14

Amino acid sequences that comprises at least 90% sequence identity to SEQ ID NO:11, or SEQ ID NO:13, such as at least 95% sequence identity, such as at least 96% sequence identity, such as at least 97% sequence identity, such as at least 98% sequence identity, or such as at least 99% sequence identity, are also considered antigenic domains of Pfs48/45. These antigenic domains when referred to herein are immunogenic and induces an immune response of at least same magnitude and quality as any one of the antigenic domains with which it shares sequence similarity, i.e. SEQ ID NO:11, or SEQ ID NO:13.

Redox Coupling Agent

In the present context, the term "redox coupling agent" refers to a compound which is capable reducing or oxidizing cysteines or cystines in proteins. Thus, a redox coupling agent induces correct folding of the fusion protein into a monomeric form protein with correctly formed disulphide bridges. Redox coupling agents include, but are not limited to, L-cysteine/cystine, gluthathione (GSH/GSSG), cysteamine/cystamine, TCEP, DTT and other small sulfhydryl containing compounds. The method as described herein may include addition of more than a single redox coupling agent.

Recombinant

In the present context, the term "recombinant" refers to a protein which is derived from a recombinant expression system (e.g., bacteria, insect or mammalian).

Recombinant Expression System

In the present context, the term "recombinant expression system" refers to a cell-based expression system based on the combination of an expression vector, its cloned DNA, and the host for the vector that provide a context to allow foreign gene function in a host cell to produce proteins at a high level. Recombinant expression system include, but are not limited to, bacterial and insect expression systems.

Lactic Acid Bacterium

In the present context, the term "lactic acid bacterium" refers to a gram-positive, microaerophilic or anaerobic bacterium which ferments sugars with the production of acids including lactic acid as the predominantly produced acid, acetic acid and propionic acid. Thus, lactic acid bacteria include, but are not limited to, *Lactococcus* spp., *Streptococcus* spp., *Lactobaccillus* spp., *Leuconostoc* spp., *pediococcus* spp., *Brevibacterium* spp. and *Propionibacterium* spp.

Additionally, lactic acid producing bacteria belonging to the group of the strict anaerobic bacteria, bifidobacteria, i.e. *Bifidobacterium* spp., which are frequently used as food starter cultures alone or in combination with lactic acid bacteria, are generally included in the group of lactic acid bacteria. A presently preferred host cell species is *Lactococcus lactis*.

SpyTag and SpyCatcher

In the present context, the terms "SpyTag" and "SpyCatcher" refers to a pair of peptides that react irreversible with each other, thereby allowing coupling of proteins to other entities. For vaccines, the SpyTag/SpyCatcher pair may be used to couple antigens to e.g. a virus-like particle (VLP), to resemble a particle that appear as a virus, thereby causing an enhanced immune response. Thus, the fusion proteins as described herein may comprise a SpyCatcher sequence enabling coupling to a VLP comprising the SpyTag.

The SpyCatcher sequence is defined by the amino acid sequence represented by SEQ ID NO:19 and encoded by the nucleic acid sequence represented by SEQ ID NO:20. The SpyTag sequence is defined by the amino acid sequence represented by SEQ ID NO:23 and encoded by the nucleic acid sequence represented by SEQ ID NO:24.

His-Tag

In the present context, the term "His-tag" refers to an amino acid sequence consisting of at least six consecutive histidine residues. The His-tag may be positioned either at the N-terminal or C-terminal end of a fusion protein as described herein, preferably at the C-terminal end. A His-tag enables purification of recombinantly expressed proteins, such as the fusion protein herein, via affinity purification as known in the art.

In the present context, if the recombinant expression system is lactic acid bacterium, such as *L. lactis*, then a His-tag is preferably positioned at the C-terminal of the fusion proteins.

C-Tag

In the present context, the term "C-tag" refers to a short amino acid sequence consisting of the amino acid residues EPEA (glutamic acid-proline-glutamic acid-alanine). The C-tag may be fused directly to the C-terminus of a protein or attached via a linker between the C-terminus and the EPEA sequence. A C-tag is a peptide tag which may be used to selectively purify recombinantly expressed proteins, such as the fusion protein herein, via affinity purification as known in the art.

In the present context, if the recombinant expression system is an insect expression system, such as Schneider 2 (S2) cells, then a C-tag is preferably positioned at the C-terminal of the fusion proteins.

Helper Protein

In the present context, the term "helper protein" refers to a protein which facilitates correct production of another protein, such as a fusion protein. A helper protein may facilitate correct folding or any other process necessary to produce a normally functioning protein. Preferably, a helper protein is a protein that facilitates proper folding of the fusion protein.

In the present context, a helper protein does not induce a desired immune response, such as an immune response suitable for use in a malaria transmission blocking vaccine (MTBV).

Glutamate Rich Protein

In the present context, the term "glutamate rich protein" refers to a protein with a high amount of glutamic acid residues, such as at least 16% glutamic acid residues.

Furthermore, in the present context, a glutamate rich protein is a protein that does not contribute to the immunological effect of the fusion protein, i.e. it does not induce a transmission blocking response. Therefore, the glutamate rich protein preferably belongs to a different stage than that of Pfs230 and Pfs48/45, such as the asexual blood stage. Thus, it is not an antigenic domain as defined above, but may instead be characterized as a helper protein as defined above.

An example of a glutamate rich protein is the glutamate rich protein (GLURP) of *Plasmodium falciparum*. GLURP is defined by the amino acid sequence represented by SEQ ID NO:21. GLURP is encoded by the nucleic acid sequence represented by SEQ ID NO:22.

Co-Expression

In the present context, the term "co-expression" refers to simultaneous expression of two or more nucleic acid sequences in a recombinant expression system. Fusion proteins as described herein are produced by co-expression of two or more nucleic acid sequences introduced into a recombinant expression system using a vector, such as a plasmid.

Specifically, fusion proteins are produced by co-expression of antigenic domains. The fusion proteins are produced without co-expression of a glutamate rich protein, such as GLURP.

Virus-Like Particle (VLP)

In the present context, the term "virus-like particle (VLP)" refers to a particle which appears as a virus, but is non-infectious because it contains no viral genetic material.

VLPs may be used as part of a vaccine to provide stronger immune response due to high density display of viral surface proteins.

Thus, VLPs include, but are not limited to, envelope and capsid proteins. A preferred VLP is the major AP205 coat protein.

Linker

In the present context, the term "linker" refers to a short peptide sequence that is situated between two protein domains (or amino acid sequences). A linker is often comprised of flexible residues, e.g. glycine and serine, so that the adjacent protein domains are free to move relative to one another. Linkers may comprise peptide motif repeats, such as two or more different peptide motif repeats.

Peptide Motif Repeats

In the present context, the term "peptide motif repeat" refers to a short amino acid sequence, which is present in a linker in more than one copy. The distinct short amino acid sequence of the peptide motif repeat may be positioned (i) consecutively, (ii) alternately with amino acid sequences different from the peptide motif repeat, or (iii) separated by amino acids sequences different from the peptide motif repeat in the linker. Peptide motif repeats may comprise at least two identical short amino acid sequences, such as at least three identical short amino acid sequences, such as at least four identical short amino acid sequences, such as at least five identical short amino acid sequences. Thus, a linker with e.g. at least three peptide motif repeats comprises at least three copies of said identical short amino acid sequences.

Circumsporozoite Protein (CSP)

In the present context, the term "Circumsporozoite protein (CSP)" refers to a protein secreted by *Plasmodium falciparum* at the sporozoite stage of the life cycle. The amino acid sequence of CSP comprises an immunodominant central repeat region and is represented by SEQ ID NO:25. CSP is encoded by the nucleic acid sequence represented by SEQ ID NO:26. CSP is a highly immunogenic protein that induces strong immune responses, e.g. when used as part of a malaria vaccine.

The fusion proteins as described herein provides an antigenic target different from that of CSP and may therefore advantageously be used in combination with CSP in a multivalent malaria vaccine. The fusion proteins may be used in combination with the native CSP protein or a fragment of the CSP protein. Preferred fragment of CSP include, but are not limited to, CSPep containing region 1 (amino acids 78-120 of SEQ ID NO:25) and CSP3/19 containing region 1, 3 NVDP and 19 NANP (amino acids 27-328 of SEQ ID NO:25). NVDP and NANP refers to the amino acid repeats in the central repeat region of CSP.

Merozoite Surface Protein 3 (MSP3)

In the present context, the term "Merozoite Surface Protein 3 (MSP3)" refers to a soluble surface protein of *Plasmodium falciparum* that is present on the merozoite surface as a protein complex. The amino acid sequence of MSP3 is represented by SEQ ID NO:27. MSP3 is encoded by the nucleic acid sequence represented by SEQ ID NO:28. MSP3 is a known antigenic target of antibody response to *Plasmodium falciparum* and is being investigated as constituents in malaria vaccines under development.

The fusion proteins as described herein provides an antigenic target different from that of MSP3 and may therefore advantageously be used in combination with MSP3 in a multivalent malaria vaccine. The fusion proteins may be used in combination with the native MSP3 protein or a fragment of the MSP3 protein.

Vaccine or Immunogenic Composition

In the present context, the terms "vaccine" and "immunogenic composition" refers to a preparation capable of producing protection or immunity to a disease by stimulating the production of antibodies. Thus, a vaccine or immunogenic composition comprises components that are antigenic of nature, thereby efficiently facilitating the production of antibodies. The antigenic component(s) may be optimized to enhance the amount and quality of the produced antibodies upon administration of the vaccine or immunogenic composition to a subject. In the present context, a vaccine or immunogenic composition comprises the fusion protein as described herein.

Escape Mutation

In the present context, the term "escape mutation" refers to the ability of a microorganism, such as *Plasmodium falciparum*, to defend itself from host immune responses by making mutations in its genotype and phenotype. Organisms with a high rate of mutations, e.g., human immunodeficiency virus, rely on mutational escape as one mechanism to avoid destruction by host cells.

Multivalent Vaccine

In the present context, the term "multivalent vaccine" refers to a vaccine designed to immunize against two or more antigens of the same microorganism, such as *Plasmodium falciparum*. Herein, the antigens are from fragments of Pfs230 and Pfs48/45.

The term "multivalent vaccine" may also be known as "polyvalent vaccine".

Pharmaceutical Acceptable

In the present context, the term "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans.

Excipients

In the present context, the term "excipient" refers to a diluent, adjuvant, carrier, or vehicle with which the composition of the invention is administered.

Carrier

In the present context, the term "carrier" refers to any and all solvents, dispersion media, vehicles, coatings, diluents, antibacterial and antifungal agents, isotonic and absorption delaying agents, buffers, carrier solutions, suspensions, colloids, polymers, such as polystyrene or polysaccharide, and the like. The use of such media and agents for pharmaceutical active substances is well known in the art. Suitable pharmaceutical carriers are described in "Remington's Pharmaceutical Sciences" by E. W. Martin.

Adjuvants

In the present context, the term "adjuvant" refers to a compound or mixture that enhances the immune response to an antigen. An adjuvant can serve as a tissue depot that slowly releases the antigen and as a lymphoid system activator, which non-specifically enhances the immune response. Often, a primary challenge with an antigen alone, in the absence of an adjuvant, will fail to elicit a humoral or cellular immune response. Adjuvants include, but are not limited to, dimethyldioctadecylammonium bromide (DDA), Quil A, poly I:C, aluminium hydroxide, Freund's incomplete adjuvant, IFN-γ, IL-2, IL-12, monophosphoryl lipid A (MPL), Treholose Dimycolate (TDM), Trehalose Dibehenate (TDB), muramyl dipeptide (MDP), monomycoloyl glycerol (MMG), saponin, surface active substances such as lysolecithin, pluronic polyols, polyanions, peptides, oil or hydrocarbon emulsions, keyhole limpet hemocyanins, dinitrophenol. A preferred adjuvant is Alhydrogel®. Preferably, the adjuvant is pharmaceutically acceptable.

Vectors

In the present context, the term “vector” refers to an expression vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

Sequence Identity

In the present context, the term “sequence identity” is here defined as the sequence identity between genes or proteins at the nucleotide, base or amino acid level, respectively. Specifically, a DNA and a RNA sequence are considered identical if the transcript of the DNA sequence can be transcribed to the identical RNA sequence.

Thus, in the present context “sequence identity” is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment, the two sequences are the same length.

In another embodiment, the two sequences are of different length and gaps are seen as different positions. One may manually align the sequences and count the number of identical amino acids. Alternatively, alignment of two sequences for the determination of percent identity may be accomplished using a mathematical algorithm. Such an algorithm is incorporated into the NBLAST and XBLAST programs of (Altschul et al. 1990). BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention.

To obtain gapped alignments for comparison purposes, Gapped BLAST may be utilized. Alternatively, PSI-Blast may be used to perform an iterated search, which detects distant relationships between molecules. When utilising the NBLAST, XBLAST, and Gapped BLAST programs, the default parameters of the respective programs may be used. See http://www.ncbi.nlm.nih.gov. Alternatively, sequence identity may be calculated after the sequences have been aligned e.g. by the BLAST program in the EMBL database (www.ncbi.nlm.gov/cgi-bin/BLAST). Generally, the default settings with respect to e.g. “scoring matrix” and “gap penalty” may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted. An embodiment of the present invention thus relates to sequences of the present invention that has some degree of sequence variation.

Fusion Proteins Comprising a Fragment of Pfs230 and a Fragment of Pfs48/45 and Method for Their Production Malaria is an infectious disease transferred to humans through mosquitoes. The disease itself is caused by singled-celled parasites belonging to the *plasmodium* genus. The parasite causing the most severe cases of malaria is *Plasmodium falciparum*. Malaria can be divided into two overall phases; asexual proliferation in the human host, and sexual proliferation in the mosquito. When the mosquito bites, it introduces the parasites from the mosquito's saliva into a person's blood, from where it travels to the liver to mature and reproduce asexually. After circulation (and further asexual reproduction) in the blood stream of the human host, the parasite may be taken up by a new vector mosquito, in which the parasite reproduce sexually. A new mosquito bite will then restart the life cycle of the parasite. Malaria vaccination strategies targeting different stages of the parasite's life cycle have been proposed. Thus, vaccine candidates attempting to prevent liver infection or targeting the blood-stage have previously been tested with varying results.

A third group of vaccines are the malaria transmission blocking vaccines (MTBVs), which aim at combating the parasite when situated in the mosquito. Consequently, this strategy revolves around vaccination with a protein necessary for sexual formation in the mosquito. As the mosquito bites a vaccinated individual it will take up antibodies against the protein, which will eventually prevent sexual reproduction in the mosquito and stop the spread of infectious parasites.

Three proteins, Pfs48/45, Pfs230, and Pfs25 are currently targeted as lead candidates for an MTBV. Vaccine constructs based on Pfs230 or Pfs48/45 are rich in cysteine and proper disulfide bond formation is critical for functional antibody responses. Solutions for proper folding of Pfs230 or Pfs48/45 have been demonstrated and revolves around coupling to the blood-stage protein GLURP. However, GLURP does not contribute to the MTBV as the antigen is expressed at a different stage of the life cycle of the parasite.

Therefore, it would be desirable to substitute the inert helper protein GLURP with a second sexual stage antigen to enhance the immune response induced by the vaccine. However, successful construction and production of fusion proteins depend on the maintenance of conformational integrity of immunologically relevant regions of the individual domains.

Herein is presented a method for production of fusion proteins comprising a fragment of Pfs230 and a fragment of Pfs48/45, i.e. leading vaccine candidates against the transmission stages of *P. falciparum*. The fusion proteins elicited high levels of functional antibodies in rodents and surprisingly outperformed the corresponding individual protein fragments. The latter observation is non-trivial as other experiments in which rodents were immunized with Pfs25 administered together with either Pfs28 or Pfs230C did not elicit higher levels of functional antibodies than the corresponding single antigen vaccines.

Thus, an aspect of the present invention relates to a method for recombinant production of a fusion protein comprising a fragment of Pfs230 and a fragment of Pfs48/45, wherein the fusion protein is produced in a recombinant expression system, optionally in the presence of one or more redox coupling agents.

As described above, disulfide bridge formation is crucial for correct folding of the fusion protein. It was found that some fragments of Pfs230 very efficiently facilitated proper folding of the fusion proteins. Indeed, the relatively N-terminal Pfs230 Pro domain enhanced protein expression of correctly folded Pfs48/45. Therefore, an embodiment of the present invention relates to the method as described herein, wherein the fragment of Pfs230 comprises the antigenic domain Pro or an amino acid sequence having at least 90% sequence identity to Pro. A further embodiment of the present invention relates to the method as described herein, wherein the antigenic domain Pro is represented by SEQ ID NO:1.

It is to be understood that amino acid sequences recited herein, which have a certain percentage of sequence identity to a recited antigenic domain, are immunogenic and induces an immune response of at least the same magnitude and quality as the antigenic domain with which it shares sequence similarity, i.e. it is suitable for use in a MTBV.

The fusion proteins described herein may also comprise additional domains derived from Pfs230 to enhance immunogenicity. Pfs230 is a large protein (>300 kDa) protein comprising the Pro domain and 14 cysteine motif (CM) domains, wherein each CM domain contains an even number of cysteine residues (2, 4 or 6). The large amount of cysteine residues makes it difficult to produce correctly folded proteins spanning many of the CM domains. Consequently, most focus has been on the most N-terminal CM domains. Thus, an embodiment of the present invention relates to the method as described herein, wherein the fragment of Pfs230 further comprises one or more antigenic domains selected from the group consisting of domains I, II, III, and combinations thereof, or amino acid sequences having at least 90% sequence identity to any one of domains I, II, and III. Another embodiment of the present invention relates to the method as described herein, wherein the antigenic domains I, II, and III are represented by SEQ ID NO:3, SEQ ID NO:5, and SEQ ID NO:7, respectively.

One specific combination of Pfs230 antigenic domains appeared in fusion proteins which consistently induced high levels of functional Pfs230-specific antibodies. Thus, a preferred embodiment of the present invention relates to the method as described herein, wherein the fragment of Pfs230 comprises the antigenic domains Pro and domain I, or amino acid sequences having at least 90% sequence identity to Pro and domain I. Another embodiment of the present invention relates to the method as described herein, wherein the fragment of Pfs230 comprising the antigenic domains Pro and domain I is represented by SEQ ID NO:9.

Full length Pfs48/45 is a cysteine rich protein of 448 amino acids and is organized into three domains (I, II and III). Especially, domains II and III has been subject to many investigations in relation to vaccine candidates and been shown to elicit high titer transmission blocking antibodies. Domain II is comprises 4 cysteine residues, whereas domain III comprises 6 cysteine residues. Domain III on its own is known as the 6C fragment, whereas domains II and III together is known as the 10C fragment. Thus, an embodiment of the present invention relates to the method as described herein, wherein the fragment of Pfs48/45 comprises one of the antigenic domains 6C and 10C, or an amino acid sequence having at least 90% sequence identity to 6C or 10C. Another embodiment of the present invention relates to the method as described herein, wherein the antigenic domains 6C and 10C are represented by SEQ ID NO:11 and SEQ ID NO:13, respectively.

Fragment 10C comprises 10 cysteine residues compared to 6 cysteine residues of fragment 6C. Thus, it is expected that correct folding of 10C is more difficult than correct folding of 6C, due to the increased amount of disulfide bridges. To improve correct folding, the Pfs48/45 fragment may therefore preferably be 6C. Thus, an embodiment of the present invention relates to the method as described herein, wherein the fragment of Pfs48/45 comprises the antigenic domain 6C or an amino acid sequence having at least 90% sequence identity to 6C.

A couple of preferred combinations of antigenic domains has been identified, both comprising the Pro domain and 6C. Therefore, an embodiment of the present invention relates to the method as described herein, wherein the fusion protein comprises:

i) the antigenic domains Pro and 6C (Pro-6C, SEQ ID NO:15), or
ii) the antigenic domains Pro, domain I and 6C (Pro+I-6C, SEQ ID NO:17), or
iii) an amino acid sequence having at least 90% sequence identity to SEQ ID NO:15 or SEQ ID NO:17.

Another embodiment of the present invention relates to the method as described herein, wherein the fusion protein comprises:

i) the antigenic domains Pro (SEQ ID NO:1) and 6C (SEQ ID NO:11), or
ii) the antigenic domains Pro (SEQ ID NO:1), domain I (SEQ ID NO:3) and 6C (SEQ ID NO:11).

A further embodiment of the present invention relates to the method as described herein, wherein the fusion protein comprises:

i) Pro-6C (SEQ ID NO:15), or
ii) Pro+I-6C (SEQ ID NO:17), or
iii) an amino acid sequence having at least 90% sequence identity to SEQ ID NO:15 or SEQ ID NO:17.

A preferred embodiment of the present invention relates to the method as described herein, wherein the fusion protein comprises the antigenic domains Pro, domain I and 6C (Pro+I-6C, SEQ ID NO:17) or an amino acid sequences having at least 90% sequence identity to SEQ ID NO:17. Another embodiment of the present invention relates to the method as described herein, wherein the fusion protein comprises Pro+I-6C (SEQ ID NO:17) or an amino acid sequences having at least 90% sequence identity to SEQ ID NO:17.

Other combinations of antigenic domains are contemplated as well. Thus, the fusion protein may be produced without the Pro domain. Therefore, an embodiment of the present invention relates to the method as described herein, wherein the fusion protein comprises:

i) one or more antigenic domains selected from the group consisting of domains I, II, III, and
ii) one of the antigenic domains 6C and 10C.

A further embodiment of the present invention relates to the method as described herein, wherein the fusion protein comprises the antigenic domain I (SEQ ID NO:3) and 6C (SEQ ID NO:11). This fusion protein is known as I+6C. An embodiment of the present invention relates to the method as described herein, wherein the fusion protein comprises I+6C or an amino acid sequences having at least 90% sequence identity to I+6C.

The Pfs230 and Pfs48/45 fragments may be arranged in any order in the fusion protein, but is preferably arranged with the Pfs230 fragment at the N-terminal end of the fusion protein. Therefore, an embodiment of the present invention relates to the method as described herein, wherein the fragment of Pfs230 is positioned at the N-terminal end of the fusion protein and the fragment of Pfs48/45 is positioned at the C-terminal end of the fusion protein.

The fusion proteins may comprise a linker for connecting the Pfs230 and Pfs48/45 fragments. Linkers may offer advantages for the production of fusion proteins, such as improving correct folding and biological activity, increasing expression yield, and achieving desirable pharmacokinetic profiles. Thus, an embodiment of the present invention relates to the method as described herein, wherein the fragment of Pfs230 and the fragment of Pfs48/45 are separated by a first linker. Another embodiment of the present invention relates to the method as described herein, wherein the first linker consists of between 10 and 60 amino acid residues.

Besides the basic role in linking the functional domains together, a linker may be used for releasing a free functional domain in vivo. Thus, three overall categories are flexible linkers, rigid linkers, and in vivo cleavable linkers. A flexible linker typically comprises a majority of flexible amino acid residues, such as glycine and serine, so that the adjacent protein domains are free to move relative to one another. Thus, an embodiment of the present invention relates to the method as described herein, wherein the first linker is a flexible linker.

Herein, several advantageous linkers have been identified, all of which increase the fusion protein yield. Therefore, an embodiment of the present invention relates to the method as described herein, wherein said first linker comprises an amino acid sequence selected from the group consisting of SEQ ID NO:42, SEQ ID NO:44, SEQ ID NO:46, SEQ ID NO:48 and SEQ ID NO:50 or an amino acid sequences having at least 90% sequence identity to any one of SEQ ID NO:42, SEQ ID NO:44, SEQ ID NO:46, SEQ ID NO:48 and SEQ ID NO:50.

In some variants of the fusion proteins, the linkers comprise peptide motif repeats. These are short repetitive amino acid sequences, such as GGGGS, NANP and NVDP, that are present in the linker in more than one copy. Thus, an embodiment of the present invention relates to the method as described herein, wherein the linker comprises at least three peptide motif repeats, such as at least four peptide motif repeats, such as at least five peptide motif repeats, such as at least six peptide motif repeats. Another embodiment of the present invention relates to the method as described herein, wherein said first linker comprises a plurality of NANP and/or NVDP peptide motif repeats. A further embodiment of the present invention relates to the method as described herein, wherein said first linker comprises a plurality of NANP and NVDP peptide motif repeats, such as at least three NANP and NVDP peptide motif repeats. Yet another embodiment of the present invention relates to the method as described herein, wherein said first linker comprises SEQ ID NO:48 or an amino acid sequence having at least 90% sequence identity to SEQ ID NO:48.

An even further embodiment of the present invention relates to the method as described herein, wherein the fusion protein comprises SEQ ID NO:58 or an amino acid sequence having at least 90% sequence identity to SEQ ID NO:58.

Another embodiment of the present invention relates to the method as described herein, wherein the fusion protein comprises an amino acid sequence selected from the group consisting of SEQ ID NO:52 (Pro(Flex2)-6C), SEQ ID NO:54 (Pro(CsTSR)-6C), SEQ ID NO:56 (Pro(CsLNK)-6C), SEQ ID NO:58 (Pro(Cs3)-6C), SEQ ID NO:60 (Pro (Sol)-6C), SEQ ID NO:64 (I-CSpep-6C), SEQ ID NO:66 (Pro+I-CSpep-10C), SEQ ID NO:68 (Pro+I-CSpep-6C) and SEQ ID NO:70 (Pro+I-CSpep-6C G397L), and or an amino acid sequence having at least 90% sequence identity to any one of said sequences.

The efficiency of vaccines may be enhanced by presentation of antigens as part of virus-like-particles (VLPs). To enable coupling to VLPs, the fusion proteins may be produced with a coupling handle. One such coupling handle is termed SpyCatcher and is a peptide sequence that irreversibly react with a corresponding coupling tag termed SpyTag. Therefore, an embodiment of the present invention relates to the method as described herein, wherein the fusion protein comprises a SpyCatcher sequence represented by SEQ ID NO:19. Another embodiment of the present invention relates to the method as described herein, wherein the SpyCatcher sequence is positioned at the N-terminal end of the fusion protein.

The fusion proteins may be purified by any standard protein purification technique known in the art. Preferred options for purification of the fusion proteins include, but are not limited to, His-tag and C-tag affinity purification. Therefore, an embodiment of the present invention relates to the method as described herein, wherein the fusion protein comprises a His-tag or C-tag. Another embodiment of the present invention relates to the method as described herein, wherein the His-tag or C-tag is positioned at the C-terminal end of the fusion protein.

Depending on the recombinant expression system utilized, either use of a His-tag or a C-tag may be favoured. Thus, if the fusion proteins are expressed in a bacterial expression system, purification by His-tag affinity is preferred. If the fusion proteins are expressed in an insect expression system, purification by C-tag affinity is preferred.

Recombinant expression of cysteine rich proteins and fragments thereof is a very unpredictable discipline, because it from organism to organism is difficult to predict whether correct disulfide bridge formation can be obtained. Careful selection of recombinant expression system is therefore required. Therefore, an embodiment of the present invention relates to the method as described herein, wherein the recombinant expression system is a bacterial or insect expression system. A further embodiment of the present invention relates to the method as described herein, wherein the bacterial expression system is a lactic acid bacterial expression system. For production of the fusion proteins described herein good results has been obtained by using *Lactococcus lactis* as the lactic acid bacterial expression system, this despite *L. lactis* lacking any sophisticated ER machinery to assist disulphide bond formation. Favourable traits of *L. lactis* include its status as a safe microorganism, its ability to grow in synthetic medium, no toxic by-products and possibility recover fusion proteins as secreted proteins. Thus, another and preferred embodiment of the present invention relates to the method as described herein, wherein the lactic acid bacterium is *Lactococcus lactis*.

Another possibility is to utilize an insect expression system. It has been found that especially expression systems based on the *Drosophila* genus is suitable to express the fusion proteins described herein. Therefore, an embodiment of the present invention relates to the method as described herein, wherein the insect expression system is a *Drosophila* expression system. A preferred embodiment of the present invention relates to the method as described herein, wherein the *Drosophila* expression system is Schneider 2 (S2) cells.

Following the transformation of the recombinant expression system host species, such as bacterial or insect cells, the transformed host species is cultivated under conditions where the fusion protein is expressed. The culture medium used to cultivate recombinant host species cells can be any conventional medium which is suitable for the purpose e.g. with respect to its nutrient composition and pH. For example, the host cells may be cultivated under anaerobic conditions in an industrial production scale. In the present context, large scale production or industrial production scale indicates that the volume of culture medium in the fermentation vessel is at least 1 L, such as at least 5 L, e.g. at least 10 L. It is also envisaged that the volume can be larger such as at least 100 L including at least 250 L.

The choice of specific fermentation conditions such as fermentation time and temperature depends on the requirements of the selected recombinant expression system host cell. Generally, the fermentation time is in the range of 10 to 30 hours such as in the range of 20-30 hours.

Efficient production of the fusion proteins may be further optimized by stabilizing the formation of monomeric fusion protein and enhancing the folding of the protein by modifying the redox conditions of the medium and the downstream processing buffer. To this end, redox coupling agents, such as reduced and oxidized forms of a sulfhydryl containing compound, may be added to the fermentation medium and/or washing buffer. Thus, an embodiment of the present invention relates to the method as described herein, wherein the redox coupling agents are selected from the group consisting of L-cysteine/cystine, gluthathione (GSH/GSSG), cysteamine/cystamine, DTT, TCEP and other small sulfhydryl containing compounds, and combinations thereof. A preferred embodiment of the present invention relates to the method as described herein, wherein the redox coupling agents are L-cysteine/cystine or cysteamine/cystamine. A further embodiment of the present invention relates to the method as described herein, wherein correct folding of the fusion protein is enhanced by the presence of reduced and oxidized forms of the redox coupling agents. Yet another embodiment of the present invention relates to the method as describer herein, wherein reduced/oxidized forms of the redox coupling agents are L-cysteine/L-cystine or cysteamine/cystamine.

Production of the fusion proteins may be further facilitated by adjusting the amount of redox coupling agents and the ratio between reduced and oxidized forms. Therefore, an embodiment of the present invention relates to the method as described herein, wherein the molar ratio of reduced to oxidized forms of the redox coupling agents are in the range of 25:1 to 1:2, such as 20:1 to 1:1, preferably 15:1 to 2:1. Another embodiment of the present invention relates to the method as described herein, wherein the redox coupling agents are present at a combined concentration of about 1-20 mM, such as about 2-15 mM, such as about 3-10 mM, preferably about 5 mM.

The method for recombinant production of the fusion protein involves the introduction of nucleic acid material of interest, herein the fragments of Pfs230 and Pfs48/45 comprising the antigenic domains, into the recombinant expression system. This is done by incorporation of the nucleic acid material into a suitable expression vector. Therefore, an embodiment of the present invention relates to the method as described herein, wherein said method comprises the following steps:

i) providing a vector comprising nucleic acid sequences encoding said fragment of Pfs230 and said fragment of Pfs48/45,
ii) introduction of said vector into said recombinant expression system,
iii) optionally, contacting said recombinant expression system with said one or more redox coupling agents, and
iv) production of said fusion protein under conditions suitable for recombinant expression.

Nucleic acids encoding fragments of Pfs230 and Pfs48/45 include nucleic acid sequences represented by SEQ ID NO: 2 (Pro domain), SEQ ID NO:4 (domain I), SEQ ID NO:6 (domain II), SEQ ID NO:8 (domain III), SEQ ID NO:10 (Pro+I), SEQ ID NO:12 (6C), SEQ ID NO:14 (10C), SEQ ID NO:63 (I-6C), SEQ ID NO:16 (Pro-6C) and SEQ ID NO:18 (Pro+I-6C).

The vector may be any of those known in the art, but a preferred option is plasmids. Thus, an embodiment of the present invention relates to the method as described herein, wherein said vector is a plasmid. Another embodiment of the present invention relates to the method as described herein, wherein said plasmid consists of nucleic acid sequences encoding a fragment of Pfs230 and a fragment of Pfs48/45, and optionally nucleic acid sequences encoding one or more selected from the group consisting of a first linker, a SpyCatcher sequence, a His-tag, a C-tag, and combinations thereof. A nucleic acid sequence encoding the SpyCatcher sequence is represented by SEQ ID NO:20.

Nucleic acids encoding linkers include, but are not limited to, nucleic acid sequences represented by SEQ ID NO: 43 (Flex2 linker), SEQ ID NO:45 (CsTSR linker), SEQ ID NO:47 (CsLNK linker), SEQ ID NO:49 (Cs3 linker), and SEQ ID NO:51 (Sol linker).

Nucleic acids encoding fusion proteins comprising a linker include, but are not limited to, nucleic acid sequences represented by SEQ ID NO:53 (Pro(Flex2)-6C), SEQ ID NO:55 (Pro(CsTSR)-6C), SEQ ID NO:57 (Pro(CsLNK)-6C), SEQ ID NO:59 (Pro(Cs3)-6C), SEQ ID NO:61 (Pro (Sol)-6C), SEQ ID NO:65 (I-CSpep-6C), SEQ ID NO:67 (Pro+I-CSpep-10C), SEQ ID NO:69 (Pro+I-CSpep-6C) and SEQ ID NO:71 (Pro+I-CSpep-6C G397L).

Following recombinant expression, the fusion protein is purified. Depending on whether or not the coding nucleic acid sequence is associated with a signal sequence, which affects the secretion of the fusion protein across the cell membrane and into the culture medium, the step of purification includes either the isolation of the fusion protein from the host cell (no signal sequence) or that it is isolated directly from the culture medium. These steps can be carried out using any conventional method of down-stream processing.

Purification of the fusion may be performed using any conventional method for such purposes, including, but not limited to, cross-flow filtration, salting out, immobilized metal-ion affinity chromatography, immune-affinity chromatography, hydrophobic interaction chromatography and/or ion exchange chromatography. Preferably, the fusion proteins are during purification subject to affinity chromatography.

It was surprisingly found that the fusion proteins could be produced without the assistance of a helper protein, thereby enabling the production of fusion proteins comprising only antigenic domains that aid to induce a beneficial immune response, such as an immune response suitable for use in a malaria transmission blocking vaccine (MTBV). Thus, an embodiment of the present invention relates to the method as described herein, wherein said fusion protein is produced in the absence of a helper protein. Another embodiment of the present invention relates to the method as described herein, wherein the vector does not comprise a helper protein.

Previous attempts to produce recombinant proteins comprising cysteine rich fragments of Pfs230 and Pfs48/45 has included a glutamate rich protein, such as GLURP, to assist correct folding of the recombinant protein. Herein, GLURP has not been used for production of the fusion proteins. Therefore, an embodiment of the present invention relates to the method as described herein, wherein said fusion protein does not comprise a glutamate rich protein. Another embodiment of the present invention relates to the method as described herein, wherein said fusion protein is produced without co-expression of a glutamate rich protein. A further embodiment of the present invention relates to the method as described herein, wherein the vector does not comprise a glutamate rich protein. An even further embodiment of the present invention relates to the method as described herein, wherein said glutamate rich protein is GLURP or part of GLURP. Yet another embodiment of the present invention relates to the method as described herein, wherein GLURP is represented by SEQ ID NO:21. A further embodiment of the present invention relates to the method as described herein, wherein the vector does not comprise a GLURP.

The fusion proteins are surprisingly produced in high yields despite the presence of multiple disulfide bridges complicating the expression of the fusion protein. Thus, an embodiment of the present invention relates to the method as described herein, wherein said fusion protein is produced in a yield of at least 2 mg/mL, such as 3 mg/L, such as 4 mg/L, such as 5 mg/L, such as at least 10 mg/L, such as at least 15 mg/L, such as at least 20 mg/L.

The method as disclosed herein enables, for the first time, production of fusion proteins comprising only leading vaccine candidates against the transmission stages of *P. falciparum*. Indeed, the fusion proteins elicited high levels of functional antibodies in rodents and surprisingly outperformed the corresponding individual protein fragments. Therefore an aspect of the present invention relates to the provision of a fusion protein obtainable by the method as described herein.

Another aspect of the present invention relates to the provision a fusion protein comprising:

i) a fragment of Pfs230 comprising the antigenic domain Pro or an amino acid sequence having at least 90% sequence identity to Pro, and
ii) a fragment of Pfs48/45 comprising one of the antigenic domains 6C and 10C, or an amino acid sequence having at least 90% sequence identity to 6C or 10C.

It is to be understood that amino acid sequences recited herein, which have a certain percentage of sequence identity to a recited antigenic domain, are immunogenic and induces an immune response of at least same magnitude and quality as the antigenic domain with which it shares sequence similarity, i.e. it is suitable for use in a MTBV.

An embodiment of the present invention relates to the provision a fusion protein consisting of:

i) a fragment of Pfs230 comprising the antigenic domain Pro or an amino acid sequence having at least 90% sequence identity to Pro, and
ii) a fragment of Pfs48/45 comprising one of the antigenic domains 6C and 10C, or an amino acid sequence having at least 90% sequence identity to 6C or 10C, and
iii) optionally, one or more selected from the group consisting of a first linker, a SpyCatcher sequence, a His-tag, a C-tag, and combinations thereof.

The fusion proteins may comprise additional antigenic domains, including additional antigenic domains originating from Pfs230. Therefore, an embodiment of the present invention relates to provision of the fusion protein as described herein, wherein the fragment of Pfs230 further comprises one or more antigenic domains selected from the group consisting of domains I, II, III, and combinations thereof, or amino acid sequences having at least 90% sequence identity to any one of domains I, II, and III. A preferred embodiment of the present invention relates to provision of the fusion protein as described herein wherein the fragment of Pfs230 comprises the antigenic domains Pro and domain I, or amino acid sequences having at least 90% sequence identity to Pro and domain I.

An embodiment of the present invention relates to the provision of the fusion protein as described herein, wherein the fragment of Pfs48/45 comprises the antigenic domain 6C or an amino acid sequence having at least 90% sequence identity to 6C.

A couple of preferred combinations of antigenic domains has been identified, both comprising the Pro domain and 6C. Therefore, a preferred embodiment of the present invention relates to provision of the fusion protein as described herein, wherein the fusion protein comprises:

i) the antigenic domains Pro and 6C (Pro-6C), or
ii) the antigenic domains Pro, domain I and 6C (Pro+I-6C), or
iii) an amino acid sequence having at least 90% sequence identity to Pro-6C or Pro+I-6C.

Another embodiment of the present invention relates to provision of the fusion protein as described herein, wherein the fusion protein consists of:

i) the antigenic domains Pro and 6C (Pro-6C) or an amino acid sequence having at least 90% sequence identity to Pro-6C, or
ii) the antigenic domains Pro, domain I and 6C (Pro+I-6C) or an amino acid sequence having at least 90% sequence identity to Pro+I-6C, and
iii) optionally, one or more selected from the group consisting of a first linker, a SpyCatcher sequence, a His-tag, a C-tag, and combinations thereof.

A further preferred embodiment of the present invention relates to provision of the fusion protein as described herein, wherein the fusion protein comprises the antigenic domains Pro, domain I and 6C (Pro+I-6C) or an amino acid sequences having at least 90% sequence identity to Pro+I-6C.

Fusion proteins not comprising the Pro domain are contemplated as well. Therefore, an additional aspect of the present invention relates to a fusion protein comprising:

i) one or more antigenic domains selected from the group consisting of domains I, II, III, and
ii) one of the antigenic domains 6C and 10C.

A further embodiment of the present invention relates to the fusion protein as described herein, wherein the fusion protein comprises the antigenic domain I (SEQ ID NO:3) and 6C (SEQ ID NO:11). This fusion protein is known as I+6C (SEQ ID NO:62). An embodiment of the present invention relates to the fusion protein as described herein, wherein the fusion protein comprises I+6C (SEQ ID NO:62)

or an amino acid sequences having at least 90% sequence identity to I+6C (SEQ ID NO:62).

The Pfs230 and Pfs48/45 fragments may be arranged in any order in the fusion protein, but is preferably arranged with the Pfs230 fragment at the N-terminal end of the fusion protein. Therefore, an embodiment of the present invention relates to provision of the fusion protein as described herein, wherein the fragment of Pfs230 is positioned at the N-terminal end of the fusion protein and the fragment of Pfs48/45 is positioned at the C-terminal end of the fusion protein.

Variants of the fusion proteins comprise a linker between the Pfs230 and Pfs48/45 fragments. Thus, an embodiment of the present invention relates to the fusion protein as described herein, wherein the fragment of Pfs230 and the fragment of Pfs48/45 are separated by a first linker. Another embodiment of the present invention relates to the fusion protein as described herein, wherein the first linker consists of between 10 and 60 amino acid residues. A further embodiment of the present invention relates to the fusion protein as described herein, wherein said first linker comprises an amino acid sequence selected from the group consisting of SEQ ID NO:42, SEQ ID NO:44, SEQ ID NO:46, SEQ ID NO:48 and SEQ ID NO:50 or an amino acid sequences having at least 90% sequence identity to any one of SEQ ID NO:42, SEQ ID NO:44, SEQ ID NO:46, SEQ ID NO:48 and SEQ ID NO:50.

Other variants of the fusion protein comprises a linker with peptide motif repeats. Thus, an embodiment of the present invention relates to the fusion protein as described herein, wherein the linker comprises at least three peptide motif repeats, such as at least four peptide motif repeats, such as at least five peptide motif repeats, such as at least six peptide motif repeats. Another embodiment of the present invention relates to the fusion protein as described herein, wherein said first linker comprises a plurality of NANP and/or NVDP peptide motif repeats. A further embodiment of the present invention relates to the fusion protein as described herein, wherein said first linker comprises a plurality of NANP and NVDP peptide motif repeats, such as at least three NANP and NVDP peptide motif repeats. Yet another embodiment of the present invention relates to the fusion protein as described herein, wherein said first linker comprises SEQ ID NO:48 or an amino acid sequence having at least 90% sequence identity to SEQ ID NO:48.

An even further embodiment of the present invention relates to the fusion protein as described herein, wherein the fusion protein comprises SEQ ID NO:58 or an amino acid sequence having at least 90% sequence identity to SEQ ID NO:58.

The concept of vaccination may rightfully be regarded as one of the most successful and beneficial medical discoveries. If designed properly, a vaccine holds the ability to completely abolish all negative effects of a disease by preventing the initial occurrence or onset of the disease. Good vaccines are characterized in their ability to elicit strong and long-lasting cellular immune responses. An effective technique to obtain this goal is by preparation of vaccines that appear as foreign particles to the immune system. This can be accomplished by coupling the antigen of interest, herein the fusion protein, to a virus-like particle (VLP). VLPs comprises viral surface proteins to appear as a virus, but does not contain any viral genetic material, making them a safer alternative to live-attenuated virus carriers.

VPLs may be coupled to the fusion protein through any suitable protein coupling reagent/technique. One specific example of protein coupling is by the SpyTag/SpyCatcher system. Thus, an embodiment of the present invention relates to provision of the fusion protein as described herein, wherein the fusion protein comprises a SpyCatcher sequence. Another embodiment of the present invention relates to provision of the fusion protein as described herein, wherein the SpyCatcher sequence is positioned at the N-terminal end of the fusion protein. A further embodiment of the present invention relates to provision of the fusion protein as described herein, wherein the fusion protein is coupled to a virus-like particle (VLP). An even further embodiment of the present invention relates to provision of the fusion protein as described herein, wherein said VLP comprises a SpyTag. Yet another embodiment of the present invention relates to provision of the fusion protein as described herein, wherein said SpyTag is attached to said VLP by a second linker. VLPs include, but are not limited to, envelope and capsid proteins. A preferred VLP is the major AP205 coat protein. Thus, an embodiment of the present invention relates to provision of the fusion protein as described herein, wherein said VLP is the major AP205 coat protein.

Fusion proteins comprising only antigenic domains that aid to induce a beneficial immune response, such as an immune response suitable for use in a malaria transmission blocking vaccine (MTBV), are provided herein. Thus, an embodiment of the present invention relates to provision of the fusion protein as described herein, wherein said fusion protein does not comprise a helper protein. Another embodiment of the present invention relates to provision of the fusion protein as described herein, wherein said fusion protein does not comprise a glutamate rich protein. A further embodiment of the present invention relates to provision of the fusion protein as described herein, wherein said glutamate rich protein is GLURP or part of GLURP.

Vaccines function by presenting disease-related antigens to an individual in a controlled manner, thereby providing the individual with active acquired immunity to that particular disease. The efficiency of a vaccine depends largely on the choice of antigen(s) and the ability of the antigen(s) to elicit strong and long-lasting cellular immune responses. The fusion proteins described herein comprise at least two distinct antigenic domains and therefore elicit immune response to more than a single antigen. Thus, the fusion proteins described herein are potent antigens that may be used in the preparation of an efficient vaccine. Therefore, an aspect of the present invention relates to provision of a multivalent vaccine or immunogenic composition comprising the fusion protein as described herein.

In order to ensure optimum performance of such a vaccine composition, it is preferred that it comprises at least one pharmaceutically acceptable carrier, adjuvant, excipient or diluent. Thus, an embodiment of the present invention relates to provision of the multivalent vaccine or immunogenic composition as described herein, further comprising one or more selected from the group consisting of pharmaceutical acceptable carriers, adjuvants, excipients and diluents.

Furthermore, the fusion protein of the invention may be coupled to a carbohydrate or a lipid moiety, or modified in other ways, e.g. by acetylation. When produced in a microorganism the fusion protein of the invention will normally not be acetylated if no special measures are taken. The acetylation may be advantageous as acetylated polypeptides may be more stable in cell, blood or body and tissue fluids. Furthermore, the acetylation may confer the polypeptide with a structure and confirmation which mimics the structure and confirmation of the native *P. falciparum* antigen.

The vaccine or immunogenic composition described herein targets the sexual stage antigens Pfs230 and Pfs48/45 comprised in the fusion protein. However, it is possible to combine the fusion protein with additional antigenic targets that could potentially belong to other stages of the life cycle of *Plasmodium falciparum*, such as the liver stage or blood stage. Thus, an embodiment of the present invention relates to provision of the multivalent vaccine or immunogenic composition as described herein, further comprising one or more additional antigenic agents. Another embodiment of the present invention relates to provision of the multivalent vaccine or immunogenic composition as described herein, wherein the one or more additional antigenic agents belong to the liver stage and/or blood stage of the life cycle of *Plasmodium falciparum*. Preferred additional antigenic agents include, but are not limited to, Circumsporozoite protein (CSP) and Merozoite Surface Protein 3 (MSP3). Therefore, an embodiment of the present invention relates to provision of the multivalent vaccine or immunogenic composition as described herein, wherein the antigenic agents are selected from the group consisting of Circumsporozoite protein (CSP) and Merozoite Surface Protein 3 (MSP3), and fragments thereof, preferably CSP or fragments thereof.

The vaccines as described herein may be administered in a manner compatible with the dosage formulation, and in such amount so as to be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 μg to 1000 μg, such as in the range from about 1 μg to 300 μg, and especially in the range from about 10 μg to 50 μg. Suitable regimens for initial administration and booster shots are also variable, but are typified by an initial administration followed by subsequent inoculations or other administrations.

The manner of application may be varied. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

Vaccines as described herein may be administered by any suitable route, including, but not limited to, parenterally or by injection, such as subcutaneously or intramuscularly.

In many instances, it will be necessary to have multiple administrations of the vaccine. Especially, vaccines can be administered to prevent an infection with malaria and/or to treat established malarial infection. When administered to prevent an infection, the vaccine is given prophylactically, before definitive clinical signs or symptoms of an infection are present.

Another aspect of the present invention relates to the provision of a fusion protein as described herein or a vaccine or immunogenic composition as described herein for use as a medicament.

A further aspect of the present invention relates to the provision of a fusion protein as described herein or a vaccine or immunogenic composition as described herein for use in the prevention, amelioration or treatment of malaria.

Provided herein are also nucleic acid sequences encoding the individual antigenic domains and fusion proteins as well as vectors comprising the nucleic acid sequences for introduction into and expression in a recombinant expression system. Therefore, an aspect of the present invention relates to the provision of a nucleic acid encoding the fusion protein as described herein.

Another aspect of the present invention relates to the provision of a vector comprising the nucleic acid as described herein.

The vector may be any vector suitable for introduction into and expression in the recombinant expression system of choice including, but not limited to, plasmids, viral vectors and cosmids. Thus, an embodiment of the present invention relates to provision of the vector as described herein, wherein the vector is selected from the group consisting of plasmids, viral vectors and cosmids, preferably plasmids.

A further aspect of the present invention relates to use of a nucleic acid as described herein or a vector as described herein for preparation of a vaccine or immunogenic composition.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1: Protocols and Methods

Preparation of Constructs

Three different truncated forms of Pfs230 from N-terminus, i.e. Pro (pro domain AA 443 to 590), Pro+I (pro domain and domain I, AA 443 to 736) and Pro+I,II,III (pro domain through domain III, AA 443 to 1132) were amplified by PCR from *P. falciparum* 3D7 DNA (GenBank accession number L08135) and cloned into the BglII restriction site of pSS5 plasmid containing N-terminus Spycatcher. $Pfs48/45_{291-428}$ (6C) was amplified from an expression vector encoding R0.6C using the forward primer 5'-CCATGGATCCGAAAAAAAAGTCATACACGGATGTAACTTC-3' (SEQ ID NO:39) and the reverse primer 5'-CCATAGATCTTGCTGAATCTATAGTAACTGTCATATAAGC-3' (SEQ ID NO:40). The amplified PCR product was digested with BamHI and Bg/II (underlined) and cloned in frame into plasmids containing the Pro or Pro+I inserts to generate Pro-6C and Pro+I-6C fusion constructs, respectively. All the constructs were verified by DNA sequencing and transformed into *L. lactis* MG1363 by electroporation for expression of recombinant proteins with 6× His tags.

Alternatively, the Pfs48/45-6C region of the SpyCatcher-6C construct (Singh et al. 2017) was amplified with the primers 5'-CCATGGATCCGAAAAAAAAGTCATACACGGATGTAACTTC-3' (SEQ ID NO:39) and 5'-CCATAGATCTTGCTGAATCTATAGTAACTGTCATATAAGC-3' (SEQ ID NO:40). A single PCR fragment of 414 bp was obtained (FIG. 1D), corresponding well to the predicted size of the Pfs48/45-6C DNA fragment.

Other PCR primers for preparation of fusion proteins include:

Pro forward (SEQ ID NO:29) and reverse (SEQ ID NO:30) primers

Domain I forward (SEQ ID NO:31) and reverse (SEQ ID NO:32) primers

Domain II forward (SEQ ID NO:33) and reverse (SEQ ID NO:34) primers

Domain III forward (SEQ ID NO:35) and reverse (SEQ ID NO:36) primers 10C forward (SEQ ID NO:37) and reverse (SEQ ID NO:38) primers Fermentation and Protein Purification Fermentation of *L. lactis* MG1363, containing Pfs230 or Pfs230-Pfs48/45 fusion constructs were carried out as follows. Fermentation of *L. lactis* MG1363 containing Pfs230 or Pfs230-Pfs48/45 fusion constructs was performed in Lactic Acid Bacterium (LAB) medium supplemented with 5% glucose, 5 µg/ml erythromycin, and 5 mM cysteine and 0.5 mM cystine in a 1 L lab scale bioreactor at 30° C. with gentle stirring (150 rpm).

Cell-free culture-filtrates were concentrated five-fold and buffer exchanged into Tris buffer (50 mM Tris, 50 mM NaCl pH 8.0 supplemented with 10 mM Imidazole) using a Quix Stand Benchtop system (Hollow fiber cartridge with cutoff at 10,000 or 30,000 Da, surface area 650 $cm^2$, GE Healthcare, Sweden) followed by filtration through a Durapore filter (PVDF, 0.22 µm, Millipore) and applied to a 5 ml HisTrap HP column (GE Healthcare, Sweden). Bound protein was eluted with 500 mM Imidazole in Tris buffer pH 8.0 (50 mM Tris, 50 mM NaCl) at a flow rate of 4 ml/min. Fractions containing the desired protein were further applied to a 5 ml HiTrap Q HP column (GE Healthcare, Sweden) for purification of monomeric proteins. Bound protein was eluted through step gradient elution in Tris buffer pH 8.0 (50 mM Tris, 1 mM EDTA, 1 M NaCl) and fractions containing monomers were concentrated by a VIVA spin column with a 10 or 30 kDa cutoff (Vivascience, Germany), and kept in 50 mM Tris, 250 mM NaCl and 1 mM EDTA, pH 8.0 at −80° C. until use.

Immune purification for Pro-6C and Pro+I-6C was done as follows. Monomeric Pro-6C and Pro+I-6C was purified on a 5 ml HiTrap NHS-activated HP column containing rat mAb 45.1 (epitope I) as described previously (Theisen et. al., 2014).

Fractions containing the desired protein were pooled and then concentrated and buffer exchanged against 50 mM Tris, 100 mM NaCl, and 1 mM EDTA, pH 8.0 and kept at −80° C. until use. Fractions were analysed by SDS-PAGE and immune blotting with mAb45.1 against Pfs48/45 conformational epitope I. Protein concentrations were measured using a BCA kit (Thermo Fisher Scientific, USA).

Protein Characterization

Analysis of purified protein was performed by size exclusion high-performance liquid chromatography (SE-HPLC). 5 µl of protein was loaded on an Agilent advance Bio SEC 300 Å, 2.7 µm, 4.6×300 mm SEC column (Agilent Technologies, GB) and eluted with a 0.1 ml/min flow of elution buffer (phosphate buffer) at room temperature. Protein standards (Sigma Aldrich) were also run using the same conditions mentioned above for sizing of the purified recombinant proteins. The amount of free cysteine residues was measured using Ellman's Reagent (Thermo Fisher Scientific, USA) following the manufacturer's instructions. A standard curve was constructed using known concentrations of free cysteine (Sigma-Aldrich, USA). Folding was determined in a mAb45.1 sandwich ELISA.

Production of Virus-Like Particles (VLPs)

SpyTag was genetically fused to the N-terminus of AP205. The SpyTag peptide sequence (AHIVMVDAYKPTKGGS, SEQ ID NO:23) was fused to the gene sequence encoding the major AP205 coat protein (Gene ID: 956335) using a flexible linker (GSGTAGGGSGS, SEQ ID NO:41) between the two sequences. The SpyTag-AP205 VLPs were expressed in Escherichia coli One Shot® BL21 Star™ (DE3) cells (Thermo Fisher Scientific, USA) and purified by ultracentrifugation using an Optiprep™ (Sigma-Aldrich, USA) gradient. For conjugation to VLPs, purified soluble Pro-6C or Pro+I-6C proteins were incubated at a molar ratio of 1:1 (VLP/antigen) in a 1×PBS buffer for 2 hours at room temperature. Unbound protein was removed by dialysis against PBS using 1,000 MWCO dialysis tubing (Spectrum Labs, USA). Densitometric analysis of SDS-PAGE gels was used to estimate protein concentrations.

Dynamic Light Scattering

Uncoupled VLP, soluble proteins and proteins conjugated to VLP were adjusted to 0.5-1 mg/ml in PBS and spun at 15,000 g for 10 min. 70 µl sample was loaded into a disposable Eppendorf Uvette cuvette (Sigma-Aldrich, USA) and measured at 25° C. on a DynoPro NanoStar (WYATT Technology, USA) equipped with a 658 nm laser. Each sample was measured 20 times and intensity-average size and percentage polydispersity (PD) was estimated using Dynamic software (Version 7.5.0).

Electron Microscopy

Pro-6C or Pro+I-6C coupled to VLP (with concentrations between 0.4-0.5 mg/ml based on antigen content) were incubated on carbon-coated and glow-discharged grids and negatively stained with 2% phosphotungstic acid (pH 7.4). The particles were analysed on a CM 100 BioTWIN electron microscope with an accelerating voltage of 80 kV. Images were acquired using an Olympus Veleta camera and particle size was estimated using ITEM software.

Animals and Immunogenicity Studies

In the first experiment, groups (n=5) of CD-1 mice 5-7 weeks of age (Janvier Labs, Denmark) were immunized 3 times at 3-week interval by the intramuscular injection of equimolar amounts of immune-purified Pro-6C and the individual Pfs230 and Pfs48/45 recombinant protein constructs formulated with Alhydrogel® (Brenntag, Denmark) to a final concentration of 2 mg/ml Aluminum. Each dose contained 128 pmoles of soluble protein (equivalent to 2 µg 6C). Serum was collected on days 14, 35 and 56. In the second experiment, groups (n=8) of CD-1 mice were immunized with 64 pmoles (equivalent to 1 µg 6C) Pro-6C or Pro+I-6C (soluble or conjugated to VLP) as described above for the first experiment. All animals were treated in accordance with the regulations and guidelines of the European and National authorities.

Enzyme-Linked Immunosorbent Assay (ELISA) for Antibody Response Measurement

Gametocyte extract ELISA was performed with cultured sexual stage of Pf NF54 parasites. Sexual-stage antigens were solubilised in 1% sodium desoxycholate, 10 mM Tris pH 8.0, 150 mM NaCl and 1 mM phenylmethylsulfonyl fluoride. After 10 min incubation at room temperature, cell debris was removed by centrifuging at 15800 g for 10 min and the supernatant containing gametocyte extract was stored until further analysis. Microtitre plates were coated overnight with the gametocyte extract, blocked with 5% milk in PBS and reacted with serial dilutions of sera in PBS-0.05% Tween 20 (PBST) for 4 h at room temperature. The secondary antibody was goat-anti mouse IgG (Novex A16072) diluted 1:3000. After 2 h incubation bound secondary antibody was quantitated with tetramethyl benzidine (TMB) substrate solution for 20 min. The color reaction was stopped with 0.2 N $H_2SO_4$ and the optical density was read at 450 nm in a Microplate Reader (Labtec BV, Germany). The plates were washed extensively with PBST—0.5 M NaCl between each incubation step.

For antigen-specific ELISA, 96-well plates (Nunc MaxiSorp) were coated with 0.5 μg/well of Pfs48/45-6C, Pro+I, or Pro+I,II,II as appropriate. Antigen-specific antibodies were detected using HRP-conjugated polyclonal goat anti-mouse IgG (Novex A16072, diluted 1:3000). Antibody midpoint titer (EC50) was calculated using sigmoidal curve fitting. Statistical analysis was conducted using GraphPad Prism 7 (GraphPad Software, USA). Data were analyzed by a nonparametric test by comparing the medians of two groups using the Mann-Whitney test.

Standard Membrane Feeding Assay (SMFA)

The biological activity of specific antisera was assessed in the SMFA. Briefly, 30 μl of mouse serum was mixed with 90 μl of naïve human serum and 150 μl of in vitro gametocyte cultures of the *P. falciparum* NF54 or *P. falciparum* NF54 (NF54-HGL) parasites expressing luciferase. The mixture was fed to *Anopheles stephensi* mosquitoes through a membrane feeding apparatus. Pre-immune sera served as the controls. Fully engorged mosquitoes were separated and held at 26° C. Seven days later, midguts of 20 mosquitoes were examined for oocysts. Non-heat inactivated mice sera, supplemented with active human complement, was added to the cultured material prior to feeding to mosquitoes. The percentage transmission reducing activity (TRA) was calculated by normalizing against oocyst counts or relative light units as appropriate in two negative control feeders. Samples were tested in two independent SMFA experiments. The best estimate and 95% confidence intervals from two separate feeds were calculated using a negative binomial model. Analyses were performed using R studio (v. 3.2.4, The R Foundation, Boston, USA).

Example 2: Expression of a Multivalent Pfs230-Pfs48/45 Fusion Protein in *L. lactis*—the Pro-6C Construct To test whether a multivalent vaccine targeting Pfs48/45 and Pfs230 is immunogenic, a fusion protein construct containing the Pro domain of Pfs230 fused to the 6C fragment of Pfs48/45 were generated (FIG. 1A). Additionally, constructs that either contained Pfs48/45 or Pfs230 fragments were generated (FIG. 1A).

Figure 1B:
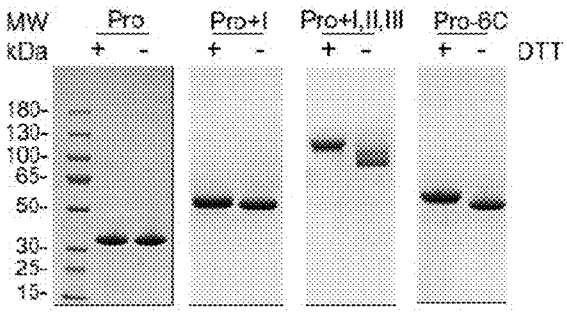

*L. lactis* MG1363 harboring these constructs were grown in a 1 L bioreactor and the respective recombinant proteins were purified from the clarified supernatant through the C-terminal His-tag by immobilized metal affinity chromatography and ion exchange chromatography (FIG. 1B). Pro-6C was further immune-purified on a mAb 45.1-column to enrich for properly folded protein species (FIG. 1B).

Figure 1C:
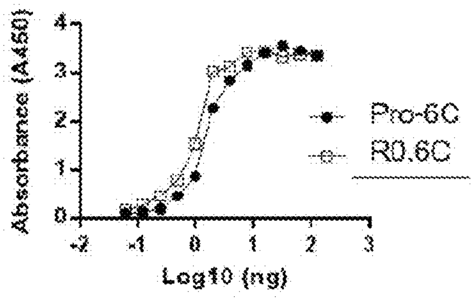
Figure 1D:
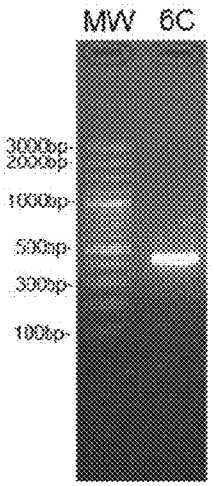

The yield of immune-purified Pro-6C was 15 mg, similar to that of R0.6C. Conformational mAb 45.1 against the Pfs48/45 epitope I reacted with Pro-6C and this binding was equivalent to that of immune-purified R0.6C suggesting that they exhibit similar cysteine-connectivity (FIG. 1C).

Conclusion: The present example demonstrates that correctly folded Pro-6C of high purity can be produced in high yields.

Example 3: Immunogenicity of Soluble Pfs48/45 and Pfs230 Protein Constructs

One concern when generating multivalent vaccines is that one of the components is immunodominant and that responses against the other component are therefore compromised. To test the immunogenicity of the fusion proteins, serum extracted from immunized mice were tested for antibody generation in an ELISA setup. Groups of mice were immunized 3 times at 3-week interval with equimolar amounts of Pro-6C and individual Pfs230 and Pfs48/45 recombinant protein constructs formulated on Alhydrogel®. A suboptimal antigen dose were used to detect differences in immunogenic properties between protein constructs.

Figure 2A:
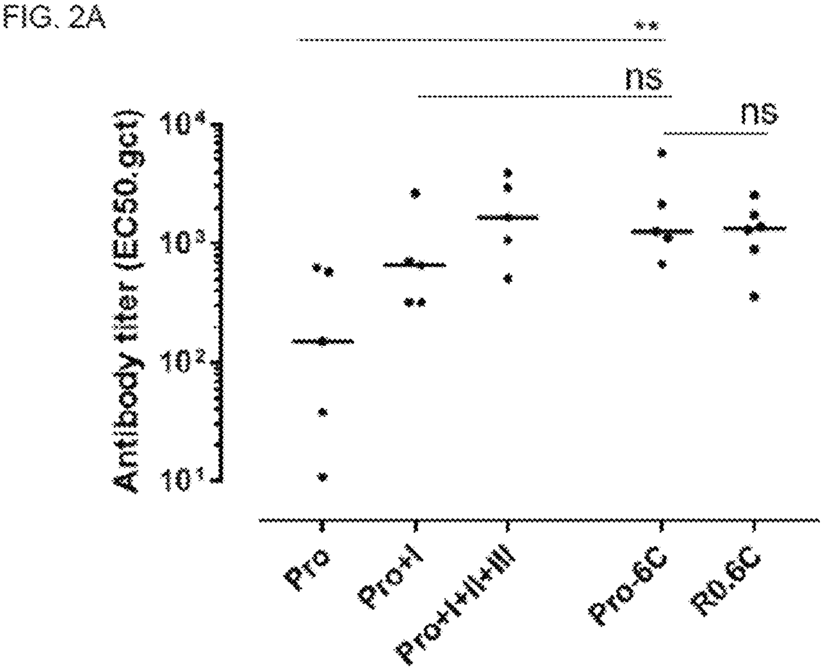
FIGS. 2A-2D shows immunogenicity of Pro-6C and individual fragments. Groups of mice (n=6) were immunized with immune purified Pro-6C in a comparative study with individual Pro, Pro+I, Pro+I,II,III and R0.6C constructs. Day 56 serum was tested for antibody reactivity on ELISA plates coated with (FIG. 1A.) gametocyte extract, (FIG. 1B) Pfs48/45-6C or (FIG. 1C) Pfs230 Pro+I,II,III. Antibody titers are expressed as EC50 values. Horizontal lines represent median values. The asterisks represent statistical significance determined by Mann-Whitney test ($p<0.01$, ns not significant).
Figure 2B:
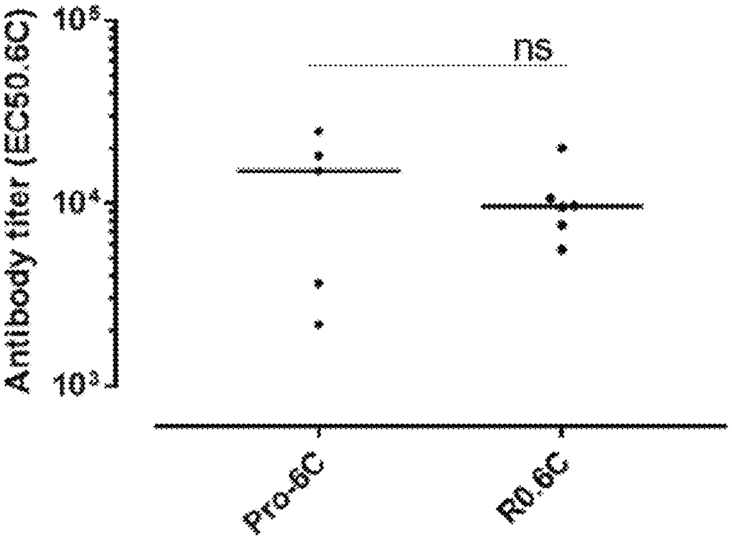
Figure 2C:
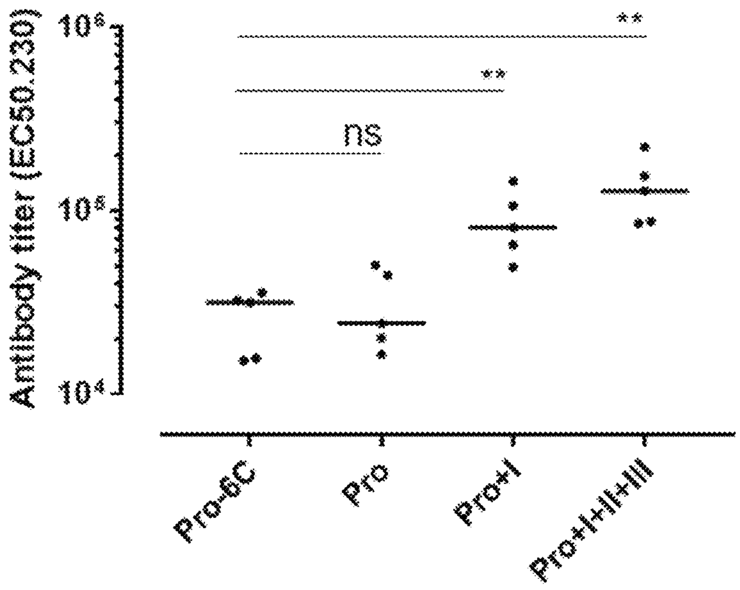

The fusion protein Pro-6C elicited significantly higher levels of gametocyte-specific antibodies than those obtained with the individual Pro domain and levels comparable to those obtained with Pro+I, and R0.6C (FIG. 2A). Furthermore, levels of specific antibodies against the Pro and 6C domains were similar in mice immunized with Pro-6C compared to mice immunized with the individual Pro and 6C (R0.6C) antigens, suggesting that these domains do not exhibit antigenic competition (FIG. 2B,C). Levels of Pfs230-specific antibodies increased with Pfs230 fragment length (FIG. 2C).

Figure 2D:
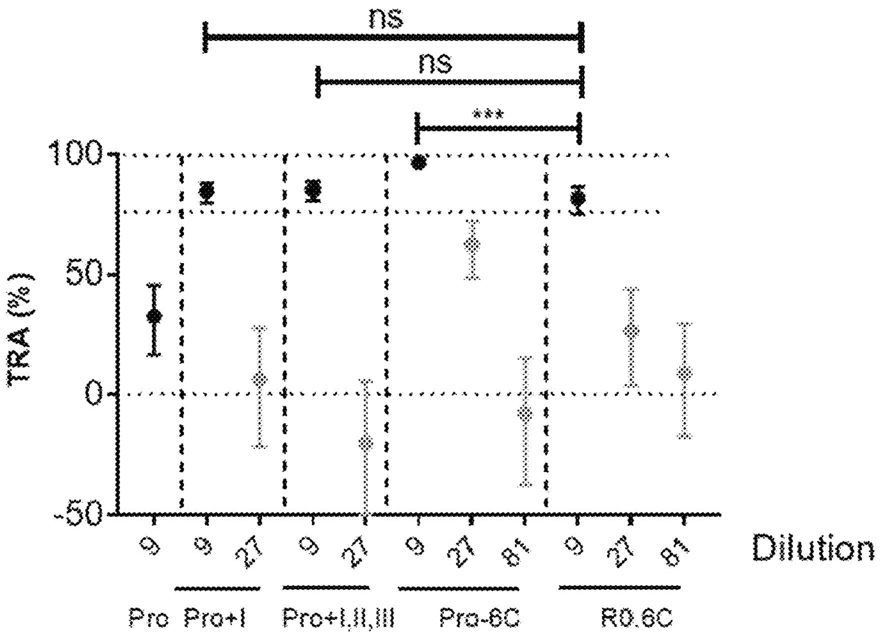

The functional activity of vaccine-induced antibodies was determined by testing pooled antisera from each group in serial dilutions in the SMFA. All proteins except the Pro domain, elicited a transmission blocking response of >80% at a 1/9 dilution. Interestingly, Pro-6C induced higher levels of functional antibodies than the other recombinant proteins, including R0.6C ($p<0.001$) (FIG. 2D).

Conclusion: The present example demonstrates that specific antibody responses against the individual antigenic domains are not affected when the antigenic domains are presented as part of fusion proteins.

Figure 3A:
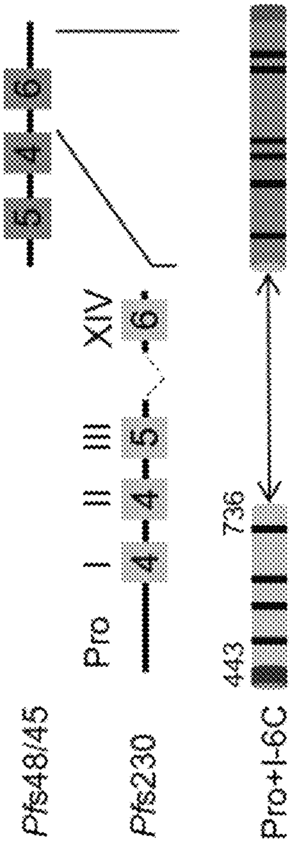
FIGS. 3A-3D shows design and characterization of a multi-domain Pfs230-Pfs48/45 fusion protein.

Example 4: Generation of Soluble Fusion Protein Constructs—the Pro+I-6C Construct To further enhance the potency of Pro-6C, a construct including the first 6-Cys domain of Pfs230 (Pro+I-6C) was produced (FIG. 3A). The Pro+I-6C fusion protein was purified following the same workflow developed for Pro-6C. The yield of immune-purified Pro+I-6C was 5 mg/mL.

Figure 3B:
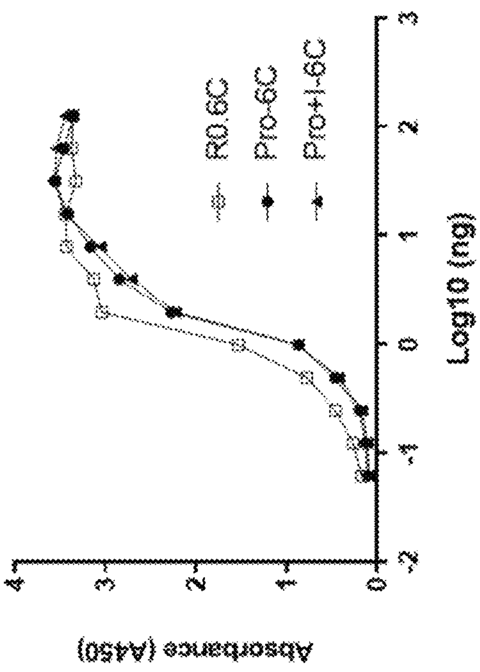
Figure 3C:
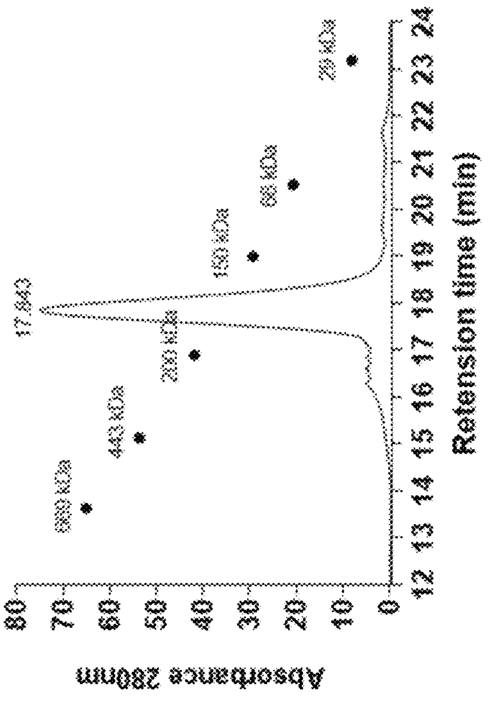
Figure 3D:
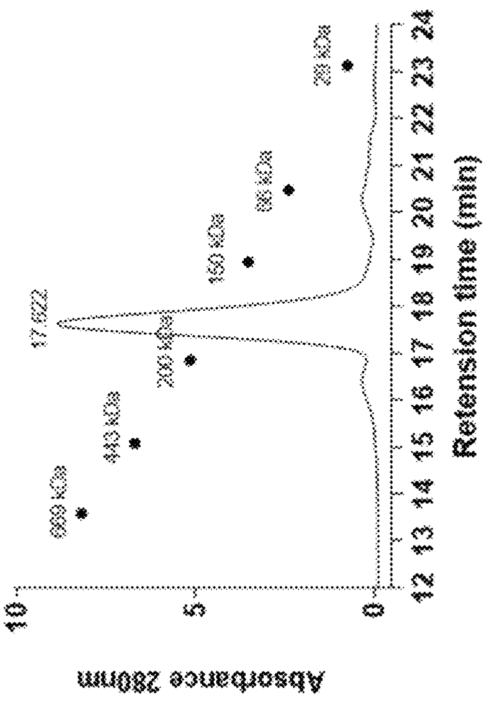

The folding of both fusion proteins was similar as determined in the mAb45.1 sandwich ELISA (FIG. 3B). Disulfide-bonding was confirmed by demonstrating very low levels of free thiol groups (<1%) under native conditions. Immune purified Pro-6C and Pro+I-6C eluted as single peaks by analytical size exclusion chromatography demonstrating that they form homogeneous solutions of monomeric protein species (FIG. 3C-D).

Conclusion: The present example demonstrates that correctly folded Pro+I-6C of high purity can be produced in high yields.

Example 5: Generation of VLP-Based Fusion Protein Constructs

Coupling of Pro-6C and Pro+I-6C to virus-like particles (VLPs) were tested to increase immunogenicity. Both Pro-6C and Pro+I-6C contained a SpyCatcher domain allowing covalent coupling to SpyTag-decorated AP205 VLPs.

Figure 4A:
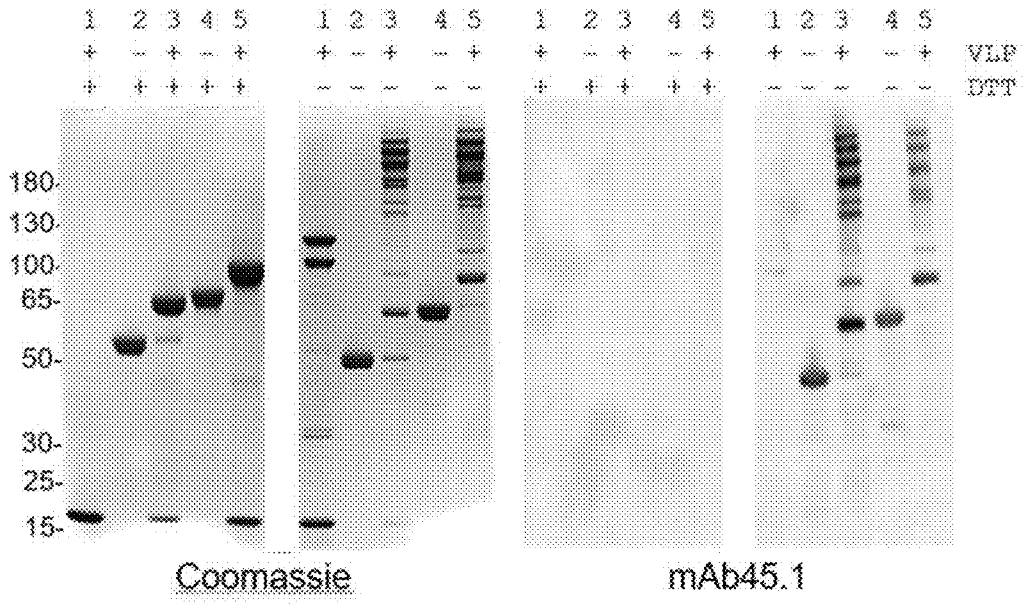
FIGS. 4A-4D shows characterization of virus-like particle-based vaccines. SpyCatcher tagged Pro-6C and Pro+I-6C were mixed with SpyTag-AP205 resulting in a unidirectional display of the fusion proteins on the VLP surface.
Figure 4B:
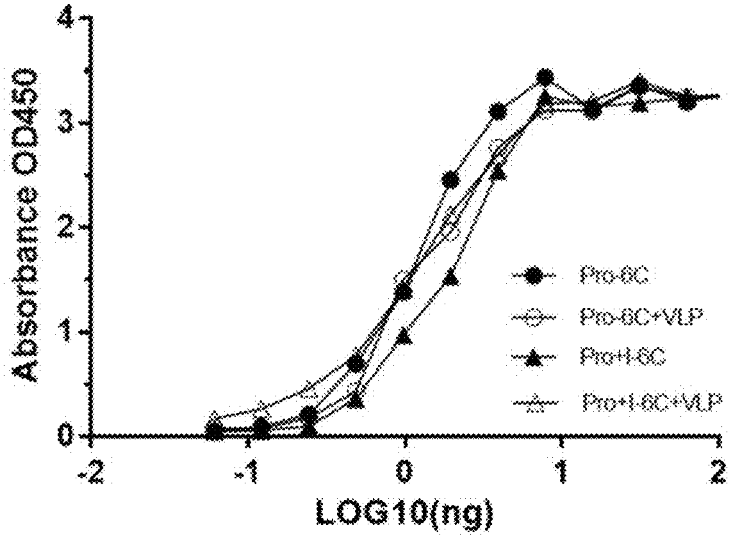
Figure 4C:
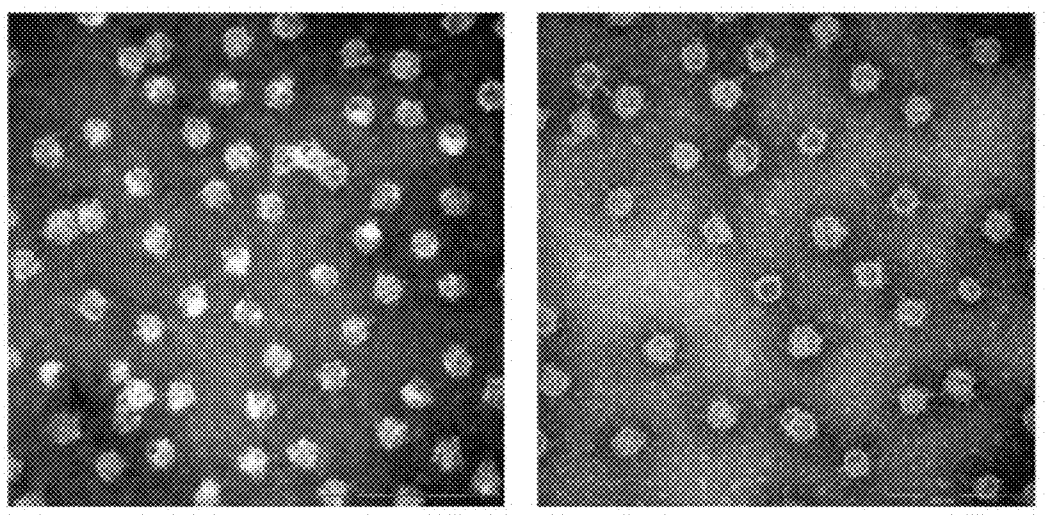
Figure 4D:
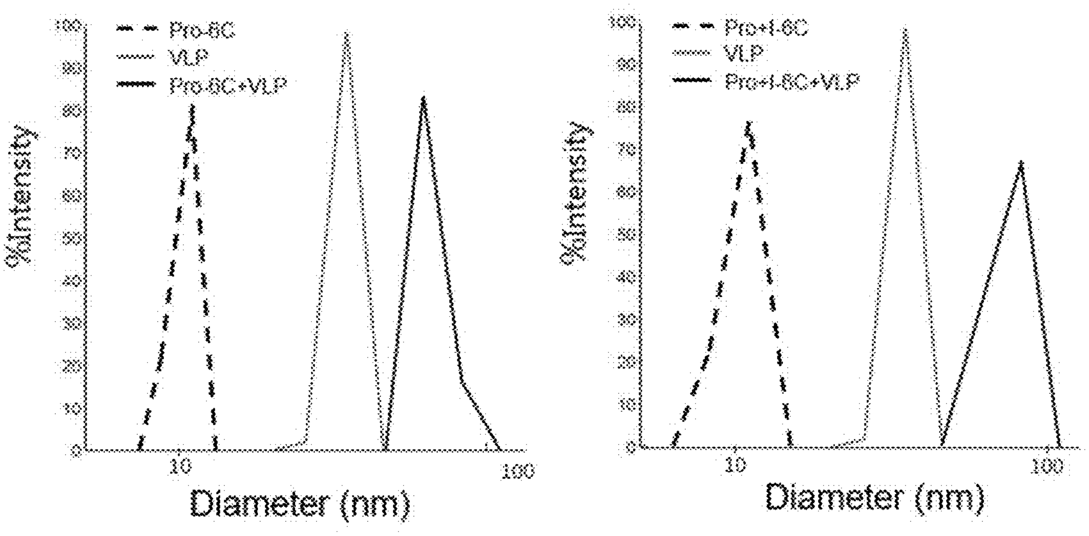

Spy-Catcher Pro-6C and Pro+I-6C coupled to SpyTag VLPs efficiently (FIG. 4A) and properly folded Pfs48/45 epitope I was retained during conjugation, as shown by western blot and mAb45.1 sandwich ELISA (FIG. 4A-B). Both VLPs formed homogenous populations of non-aggregated antigen-VLP complexes as demonstrated by transmission electron microscopy (FIG. 4C). Furthermore, dynamic light scattering (DLS) experiments demonstrated a low percentage of polydispersity (<16%) and an average size of 71.8 nm and 73.7 nm for the VLP-particles displaying Pro-6C and Pro+1-6C, respectively (FIG. 4D).

Conclusion: The present example demonstrates that fusion proteins coupled to VLPs retained correct folding and could be obtained in highly monodisperse populations.

Example 6: Immunogenicity of Soluble and VLP-Based Fusion Protein Constructs The immunogenicity of the Pro-6C-VLP and the Pro+I-6C-VLP vaccine formulations were compared to that of soluble Pro-6C and Pro+I-6C. Groups of CD-1 mice (n=8) were immunized 3 times at 3-week intervals with equimolar amounts of antigen adjuvanted on Alhydrogel®. Control groups were immunized with soluble fusion proteins in the same adjuvant.

Figure 5A:
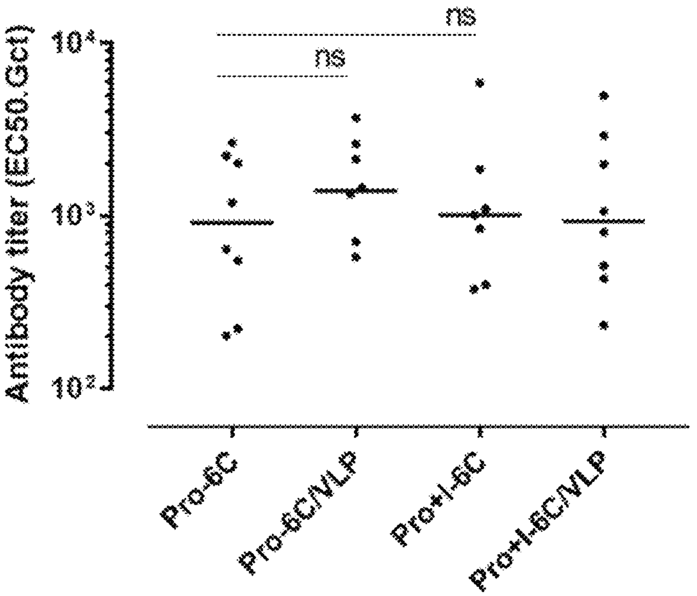
FIGS. 5A-5D shows VLP-delivery of Pro-6C and Pro+I-6C. Groups of mice (n=8) were immunized with soluble Pro-6C and Pro+I-6C or bound to AP205. Day 56 serum was tested for antibody reactivity on ELISA plates coated with (FIG. 5A) gametocyte extract, (FIG. 5B) Pfs48/45-6C or (FIG. 5C) Pfs230 Pro+I,II,III. Antibody titers are expressed as EC50 values. Horizontal lines represent median values. The asterisks represent statistical significance determined by Mann-Whitney test ($p<0.01$, ns not significant).
Figure 5B:
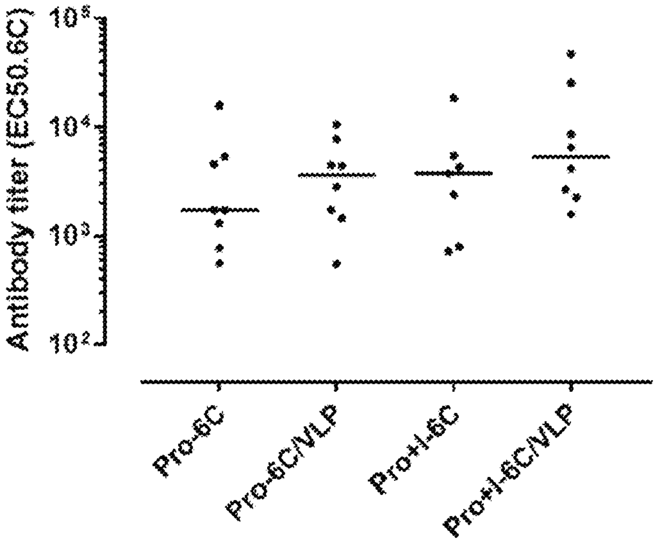
Figure 5C:
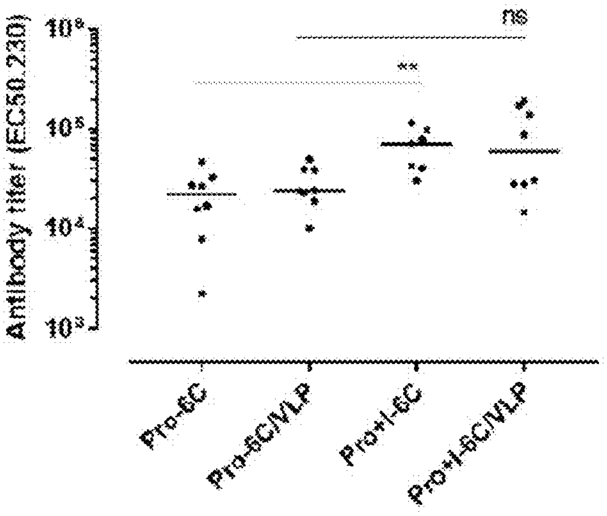

VLP display did not provide an increase in gametocyte-, Pfs48/45-, or Pfs230-specific antibodies (FIG. 5A-C). Soluble Pro+I-6C elicited significantly (P=0.0079) higher levels of Pfs230-specific responses than soluble Pro-6C (FIG. 5C) although this increase was not associated with higher levels of gametocyte-specific antibodies (FIG. 5A).

Figure 5D:
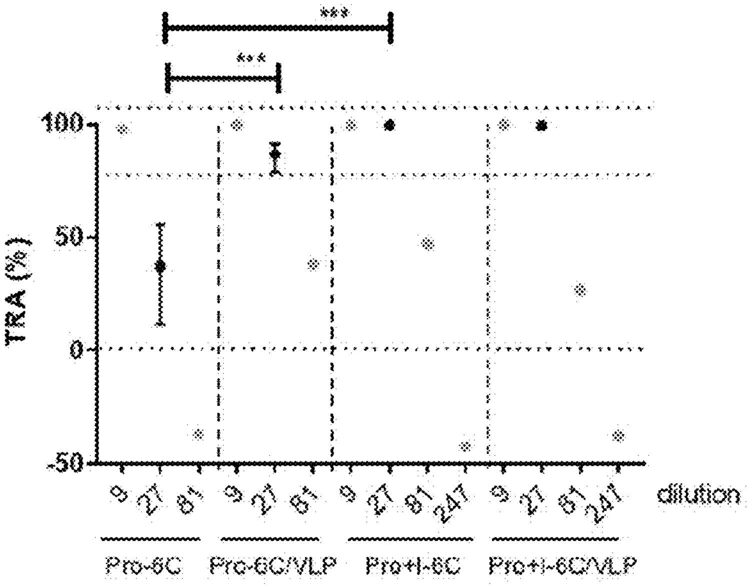

The functional activity of pooled anti-sera from each group was tested at serial dilutions in the SMFA. Antibodies against soluble Pro+I-6C promoted higher SMFA activity than antibodies against Pro-6C at a 1/27 dilution ($p<0.001$) (FIG. 5D), in line with the SMFA results obtained with the single domain constructs (FIG. 2D). VLP-display of Pro-6C enhanced ($p<0.001$) the production of functional antibodies as demonstrated in the SMFA, while there was no such effect on the immunogenicity of Pro+I-6C (FIG. 5D).

Conclusion: The present example demonstrates that fusion proteins coupled to VLPs retain immunogenicity and in some cases enhance production of functional antibodies. Furthermore, the example demonstrates that the functional activity in the SMFA is not only dependent on quantity but also the quality of antibodies, e.g. the Pro+I-6C fusion protein provides a better presentation of antibody epitopes.

Example 7: Pfs230-Pfs48/45 Fusion Proteins with Internal Linker

Figure 6A:
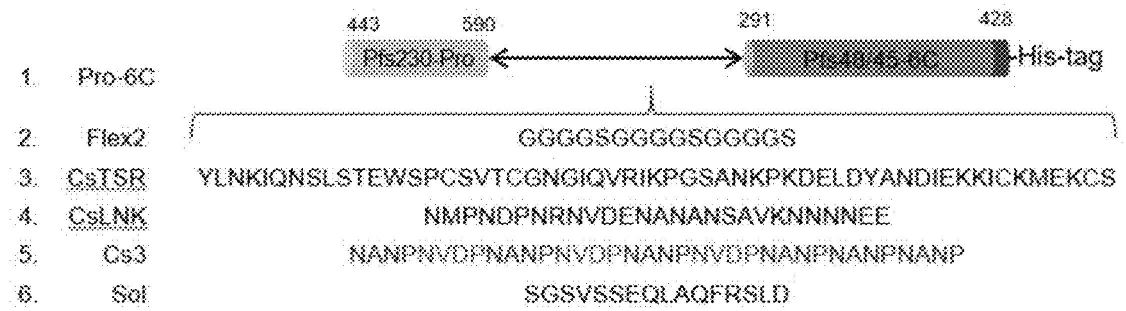
FIGS. 6A-6C shows a schematic of fusion protein constructs comprising a linker and verification of their production.

The effect of a linker connecting the Pfs230 fragment and Pfs48/45 fragment was investigated. Therefore, a panel of linker sequences were inserted between the two domains and the resulting constructs were produced in the *L. lactis* expression system (FIG. 6A). The linkers tested were of different length and structural properties and were based on both non-natural peptides and naturally occurring peptides from the multi-domain *P. falciparum* CS protein. The following fusion proteins were produced; Pro(Flex2)-6C (SEQ ID NO:52), Pro(CsTSR)-6C (SEQ ID NO:54), Pro (CsLNK)-6C (SEQ ID NO:56), Pro(Cs3)-6C (SEQ ID NO:58), Pro(Sol)-6C (SEQ ID NO:60), and Pro-6C (SEQ ID NO:15) as reference.

Figure 6B:
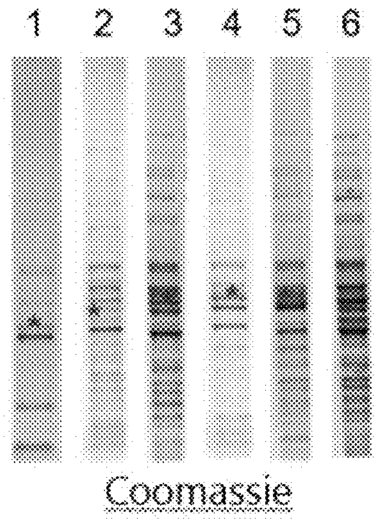
Figure 6C:
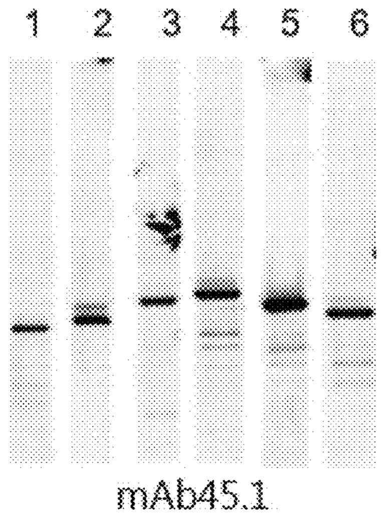

Each construct was transformed into *L. lactis* MG1363 and the selected clones were grown overnight in 5 ml of LAB medium at 30° C. without shaking. For comparison, the Pro-6C fusion protein lacking a linker sequence was assessed in parallel. Firstly, all recombinant clones produced a secreted recombinant protein as detected by SDS-PAGE (FIG. 6B), with some of the constructs producing higher amounts of recombinant protein than Pro-6C without a linker. Secondly, all recombinant fusion proteins comprising a linker reacted with the transmission blocking (TB) mAb45.1, which binds to the conformational epitope in the Pfs48/45-6C domain (FIG. 6C). Some of the fusion proteins comprising a linker bound mAb45.1 stronger than Pro-6C did indicating that the introduction of a linker may promote correct the folding of the Pfs48/45-6C domain.

To determine the expression yields, all constructs were grown in 0.5 L stirred bioreactor for 15 h at 30° C. Supernatants were concentrated and exchanged to 20 mM HEPES, 50 mM NaCl pH 8.0 supplemented with 15 mM imidazole. The fusion proteins with linkers were captured on a His-Trap HP column and bound protein was eluted with an imidazole gradient. Fractions containing high quantities of target protein as determined by SDS-PAGE analysis were pooled and applied to an ion-exchange chromatography column to separate monomeric and multimeric protein species. Fractions containing high amounts of monomeric protein were pooled and kept for further analysis. The overall yield and folding of each recombinant protein relative to immune purified reference material is listed in Table 1.

TABLE 1

| Construct | Protein (mg/L) | Fold increase | % of folding |
|---|---|---|---|
| Pro-6C | 4.0 | 1 | 90 |
| Pro(Flex2)-6C | 5.0 | 1.3 | 100 |
| Pro(CsTSR)-6C | 5.0 | 1.3 | 72 |
| Pro(CsLNK)-6C | 5.5 | 1.4 | 75 |
| Pro(Cs3)-6C | 8.0 | 2 | 100 |
| Pro(Sol)-6C | 5.5 | 1.4 | 90 |

Conclusion: The present example demonstrates that the addition of a linker sequence increased the overall yield of Pro-6C. Cs3, in particular, exhibited approx. 2-fold increased yield and was most correctly folded.

Example 8: Biological Activity of Pfs230-Pfs48/45 Fusion Proteins with Internal Linker It is well established that the folding of recombinant Pfs48/45 affects its ability to elicit TB antibodies. Therefore, the immunogenicity of all fusion proteins comprising a linker was investigated.

Figure 7A:
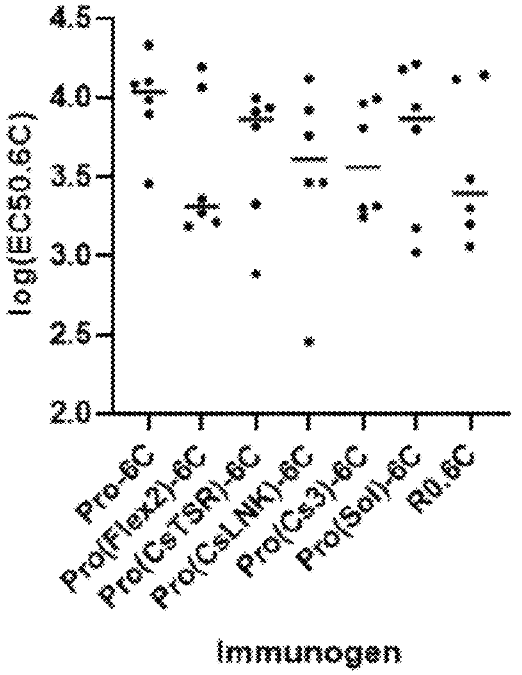
FIGS. 7A-7C shows immunogenicity of fusion protein constructs comprising a linker and their ability to facilitate production of transmission blocking antibodies. Sera from mice immunized with Pro-6C, Pro(Flex2)-6C, Pro(CsTSR)-
Figure 7B:
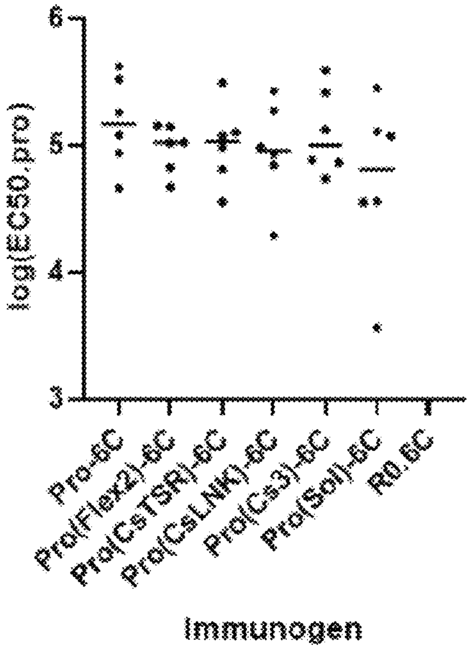
Figure 7C:
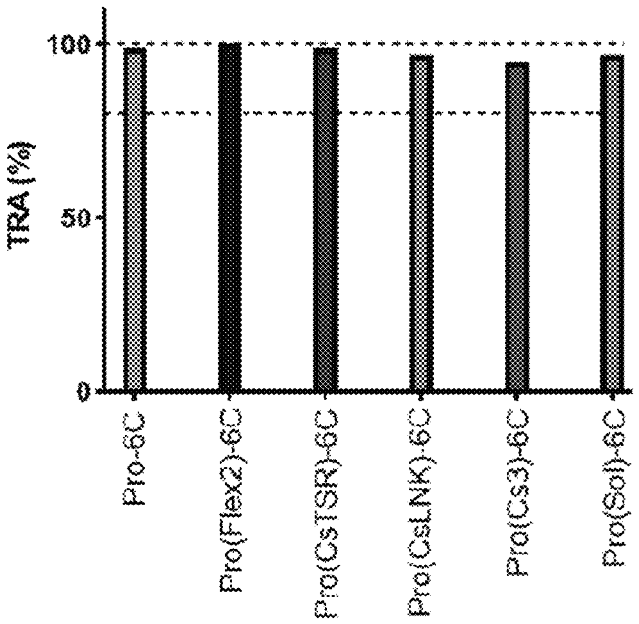

Groups of out-bred CD-1 mice were immunized 3 times at 3-week intervals (n=6). Two weeks after the last injection, mice were bled, and specific antibodies were assessed by ELISA on plates coated with either Pfs48/45-6C (FIG. 7A) or Pfs230-Pro (FIG. 7B). All the constructs elicited domain-specific antibodies at levels comparable to those obtained with Pro-6C (FIGS. 7A and 7B). The R0.6C construct was included as a control, demonstrating only immunogenicity against Pfs48/45-6C as expected. Lastly, antisera were tested for functional activity in the SMFA. Antisera against all constructs, <80% TRA at 1/9 dilution demonstrating that the linkers did not modify the immunogenicity of the Pfs230-Pro and Pfs48/45-6C domains (FIG. 7C).

Conclusion: All fusion proteins comprising a linker connecting the Pfs230 fragment and Pfs48/45 fragment elicited high levels of functional antibodies in mice.

Example 9: Expression of Fusion Proteins in S2 Cells

Figure 8A:
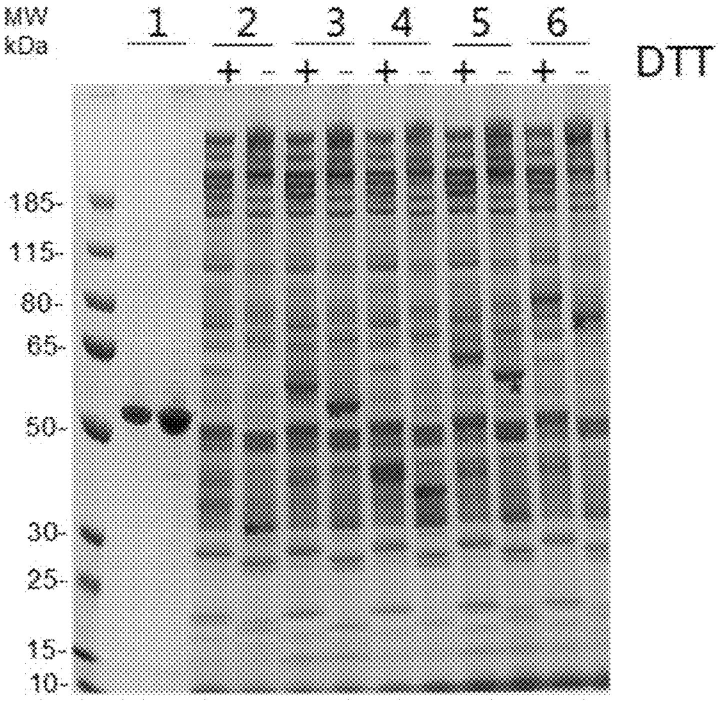
FIGS. 8A-8D shows expression of recombinant fusion proteins in S2 cells and subsequent characterization.

Five Pfs230 and Pfs48/45 based chimeric constructs were synthesized with a C-terminal C-tag (Geneart, Germany) and cloned into pExpressS2-1 digested with EcoRI and NotI. All constructs were verified by DNA sequencing and transfected into S2 cells using standard procedures. The cell lines were expanded for 3 weeks at 30° C. S2 cells were harvested by centrifugation and culture-supernatants were concentrated five-fold, buffer exchanged into Tris-HCl buffer (20 mM Tris-HCl, 21 mM NaCl, pH 7.0) using a Quix Stand Benchtop system (GE Healthcare, Sweden) and sterilized by filtration through a Durapore filter (PVDF, 0.22 μm, Millipore). Polyclonal cell lines containing each construct produced a recombinant protein of the expected MWs (FIG. 8A). The following fusion proteins were produced; I-6C (SEQ ID NO:62), Pro+I-6C (SEQ ID NO:17), I-CSpep-6C (SEQ ID NO:64), Pro+I-CSpep-6C (SEQ ID NO:68), and Pro+I-CSpep-10C (SEQ ID NO:66).

Figure 8B:
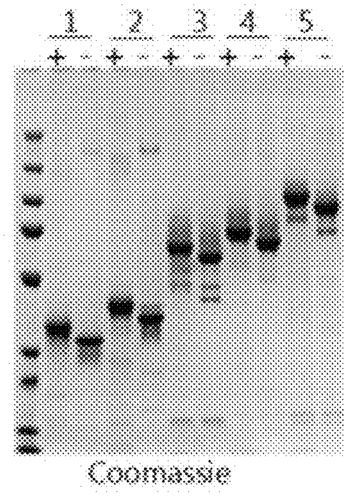
Figure 8C:
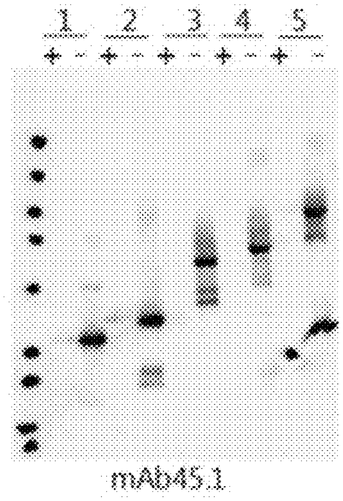
Figure 8D:
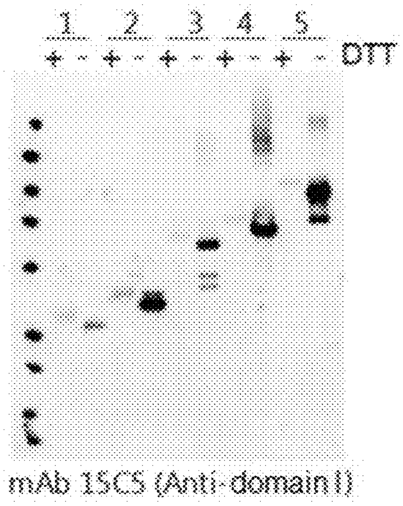

The recombinant fusion proteins were purified by applying culture supernatants to a 5 ml CaptureSelect C-tagXL Affinity (Thermofisher, USA). Bound fusion protein was eluted with 2 M MgCl2 pH 7.0 in Tris-HCl buffer pH 7.0 (20 mM TrisHCl, 21 mM NaCl) at a flow rate of 2.5 ml/min and fractions containing the desired fusion protein were pooled and applied to a 5 ml HiTrap Q HP column (GE Healthcare, Sweden). Bound fusion protein was eluted by a gradient elution in Tris-HCl buffer pH 8.0 (20 mM Tris-HCl, 1 mM EDTA, 1 M NaCl) and fractions containing monomers were concentrated and buffer exchanged to 20 mM Tris-HCl, 250 mM NaCl and 1 mM EDTA, pH 8.0. Purified fusion protein was analyzed by SDS-PAGE analysis and immune blotting with mAb45.1 against Pfs48/45 conformational epitope I and mAb 15C5 against Pfs230 conformational epitope D1 (herein denoted "domain I" or simply "I") (FIG. 8B-D). Purified protein contained a predominance of monomers, which were recognized by mAb45.1 and mAb15C5 suggesting they contain correctly folded protein species. Yields are given in Table 2.

TABLE 2

| Construct | Protein (mg/L) |
|---|---|
| I-6C | 2.0 |
| I-CSpep-6C | 2.5 |
| Pro + I-6C | 4.0 |
| Pro + I-CSpep-6C | 5.0 |

TABLE 2-continued

| Construct | Protein (mg/L) |
|---|---|
| Pro + I-CSpep-10C | 3.0 |
| Pro + I-CSpep-6C MT | 5.5 |

Conclusion: The S2 expression system can be used for the production of Pfs230-Pfs48/45 fusion proteins.

Example 10: G397L Mutation in the Pro+I-CSpep-6C Fusion Protein

The effect of a single point mutation, G397L, on the expression of the Pro+I-CSpep-6C fusion protein was investigated in S2 cells. The mutation replaced Leucine with Glycine (G397L) at position 397 in the C-terminus of the Pfs48/45-6C sequence.

Figure 9A:
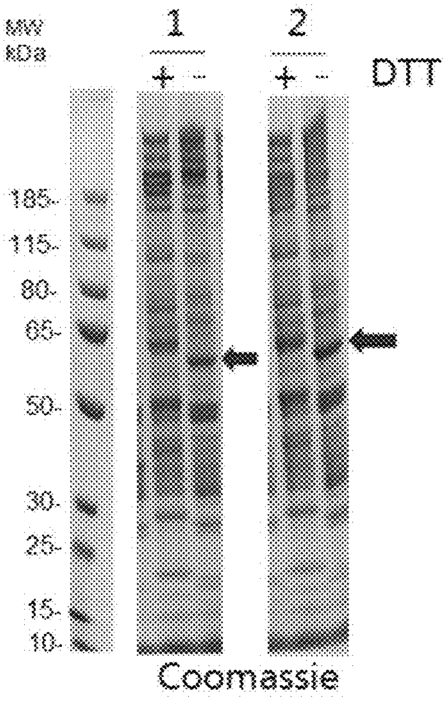
FIGS. 9A-9C shows expression of Pro+I-CSpep-6C with G397L mutation in S2 cells.
Figure 9B:
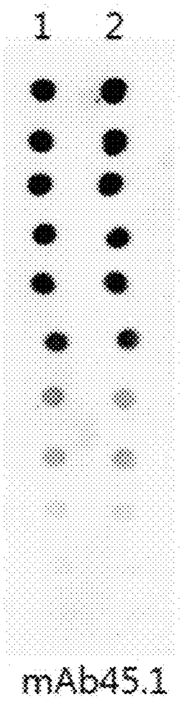
Figure 9C:
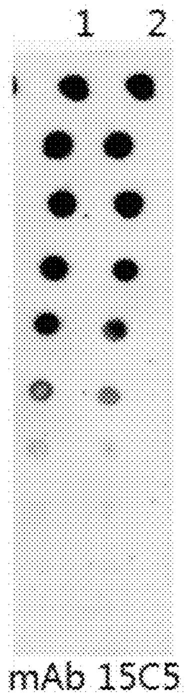

Two constructs, Pro+I-CSpep-6C (wildtype, SEQ ID NO:68) and Pro+I-CSpep-6C G397L (mutant, SEQ ID NO:70) were produced in S2 cells as described in Example 9. This single point mutation did not affect protein expression (FIG. 9A). The folding of the respective recombinant fusion proteins was assessed by immune blotting with mAb45.1 against Pfs48/45 (FIG. 9B) and mAb 15C5 against Pfs230 conformational epitope D1 (herein denoted "domain I" or simply "I") (FIG. 9C). Both the wildtype and the mutant fusion protein were recognized equally well by the two mAbs. The yields of the purified recombinant fusion protein was 5 and 5.5 mg/L for the wildtype and mutant fusion proteins, respectively.

Conclusion: The G397L mutation did not affect overall expression yield or the folding of the respective Pfs48/45- and Pfs230-domains.

REFERENCES

Theisen et al. (2014), Vaccine, 32, 2623-2630
Singh et al. (2017), Microbial cell factories, 16:97
MacDonald et al. (2016), J. Biol. Chem., 291, 19913-19922
WO2013/050034 A1
Singh et al. (2017), Vaccine, 35, 3726-373

The invention claimed is:

1. A method for recombinant production of a fusion protein comprising a fragment of Pfs230 and a fragment of Pfs48/45, wherein the fusion protein is produced in a recombinant expression system, in the presence of one or more redox coupling agents and the fragment of Pfs230 comprises the antigenic domain Pro (SEQ ID NO:1) or an amino acid sequence having at least 95% sequence identity to Pro (SEQ ID NO:1), and wherein the fragment of Pfs48/45 comprises one of the antigenic domains 6C (SEQ ID NO: 11) and 10C (SEQ ID NO:13), or an amino acid sequence having at least 95% sequence identity to 6C (SEQ ID NO: 11) or 10C (SEQ ID NO:13).

2. The method according to claim 1, wherein the fragment of Pfs230 further comprises one or more antigenic domains selected from the group consisting of domains I (SEQ ID NO:3), II (SEQ ID NO:5), III (SEQ ID NO:7), and combinations thereof, or amino acid sequences having at least 95% sequence identity to any one of domains I (SEQ ID NO: 3), II (SEQ ID NO:5), and III (SEQ ID NO:5).

3. The method according to claim 1, wherein the fusion protein comprises:

i) the antigenic domains Pro (SEQ ID NO:1) and 6C (SEQ ID NO:11), or ii) the antigenic domains Pro (SEQ ID NO:1), domain I (SEQ ID NO:3) and 6C (SEQ ID NO: 11).

4. The method according to claim 3, wherein the fusion protein comprises Pro+I-6C (SEQ ID NO:17) or an amino acid sequence having at least 95% sequence identity to SEQ ID NO:17.

5. The method according to claim 3, wherein the fragment of Pfs230 and the fragment of Pfs48/45 are separated by a first linker.

6. The method according to claim 3, wherein the fusion protein comprises a SpyCatcher sequence represented by SEQ ID NO:19.

7. The method according to claim 3, wherein the fusion protein comprises a His-tag or C-tag.

8. The method according to claim 1, wherein the recombinant expression system is a bacterial or insect expression system.

9. The method according to claim 8, wherein the insect expression system is a *Drosophila* expression system.

10. The method according to claim 1, wherein the redox coupling agents are selected from the group consisting of L-cysteine/cystine, gluthathione (GSH/GSSG), cysteamine/cystamine, DTT, TCEP and other small sulfhydryl containing compounds, and combinations thereof.

11. The method according to claim 1, wherein said method comprises the following steps:

i) providing a vector comprising nucleic acid sequences encoding said fragment of Pfs230 and said fragment of Pfs48/45, ii) introduction of said vector into said recombinant expression system, iii) contacting said recombinant expression system with said one or more redox coupling agents, and iv) production of said fusion protein under conditions suitable for recombinant expression.

12. The method according to claim 1, wherein said fusion protein does not comprise a glutamate rich protein.

13. A fusion protein comprising:

i) a fragment of Pfs230 comprising the antigenic domain Pro (SEQ ID NO:1) or an amino acid sequence having at least 95% sequence identity to Pro, and ii) a fragment of Pfs48/45 comprising one of the antigenic domains 6C (SEQ ID NO:11) and 10C (SEQ ID NO:13), or an amino acid sequence having at least 95% sequence identity to 6C (SEQ ID NO:11) or 10C (SEQ ID NO:13).

14. The fusion protein to claim 13, wherein the fragment of Pfs230 further comprises one or more antigenic domains selected from the group consisting of domains I (SEQ ID NO:3), II (SEQ ID NO:5), III (SEQ ID NO:7), and combinations thereof, or amino acid sequences having at least 95% sequence identity to any one of domains I (SEQ ID NO: 3), II (SEQ ID NO:5), and III (SEQ ID NO:7).

15. The fusion protein according to claim 13, wherein the fragment of Pfs230 and the fragment of Pfs48/45 are separated by a first linker.

16. The fusion protein according to claim 15, wherein the fusion protein is coupled to a virus-like particle (VLP).

17. The fusion protein according to claim 13, wherein said fusion protein does not comprise a glutamate rich protein.

18. A method for the prevention, amelioration or treatment of malaria by administering a fusion protein according to claim 13 to a subject.

* * * * *